US006800249B2

(12) United States Patent
de la Torre-Bueno

(10) Patent No.: US 6,800,249 B2
(45) Date of Patent: Oct. 5, 2004

(54) AUTOMATED SLIDE STAINING APPARATUS

(75) Inventor: Jose de la Torre-Bueno, Encinitas, CA (US)

(73) Assignee: ChromaVision Medical Systems, Inc., San Juan Capistrano, CA (US)

( * ) Notice: Subject to any disclaimer, the term of this patent is extended or adjusted under 35 U.S.C. 154(b) by 0 days.

(21) Appl. No.: 10/461,733

(22) Filed: Jun. 12, 2003

(65) Prior Publication Data

US 2004/0009098 A1 Jan. 15, 2004

Related U.S. Application Data

(60) Provisional application No. 60/389,177, filed on Jun. 14, 2002.

(51) Int. Cl.[7] .............................................. G01N 35/00
(52) U.S. Cl. ........................ 422/63; 422/67; 422/82.05; 422/100; 436/43; 436/46; 436/164; 436/165; 436/180; 435/287.3; 382/128; 382/133
(58) Field of Search .......................... 436/43, 46, 164, 436/165, 180; 422/63, 65, 67, 82.05, 99, 100; 435/287.1, 287.3; 382/128, 133, 134; 700/266; 702/19, 21

(56) References Cited

U.S. PATENT DOCUMENTS

| 4,004,550 A | 1/1977 | White et al. |
| 4,089,989 A | 5/1978 | White et al. |
| 5,009,185 A | 4/1991 | Stokes et al. |
| 6,037,168 A | * 3/2000 | Brown ..................... 435/288.3 |
| 6,096,271 A | 8/2000 | Bogen et al. |
| 6,180,061 B1 | 1/2001 | Bogen et al. |
| 6,183,693 B1 | 2/2001 | Bogen et al. |
| 6,215,892 B1 | * 4/2001 | Douglass et al. ........... 382/128 |
| 6,349,264 B1 | 2/2002 | Rhett et al. |
| 6,352,861 B1 | 3/2002 | Copeland et al. |
| 6,358,473 B1 | 3/2002 | Coello et al. |
| 6,418,236 B1 | * 7/2002 | Ellis et al. .................. 382/128 |
| 6,468,764 B1 | 10/2002 | Gibbs et al. |
| 6,585,936 B1 | 7/2003 | Shah |
| 2003/0099573 A1 | * 5/2003 | Tseung et al. ................ 422/63 |

FOREIGN PATENT DOCUMENTS

| WO | 01/57785 | * 8/2001 |
| WO | 01/68259 | * 9/2001 |

* cited by examiner

Primary Examiner—Maureen M. Wallenhorst
(74) Attorney, Agent, or Firm—Fish & Richardson P.C.

(57) ABSTRACT

Disclosed is an automated staining apparatus (autostainer) capable of staining sample on a microscope slide. The autostainer is capable of limiting the amount of reagent used through a process including image acquisition and processing techniques, wherein an image of the slide is acquired and used to determine a region on the slide to be stained. Also disclosed are methods of using images acquired by the autostainer in sample processing. In addition, a system including the autostainer functionally linked to an imaging system is provided.

15 Claims, 28 Drawing Sheets

AUTOMATED SLIDE STAINING APPARATUS

CROSS REFERENCE TO RELATED APPLICATIONS

The present application claims priority under 35 U.S.C. §119 to U.S. Provisional Application Ser. No. 60/389,177, filed Jun. 14, 2002, the disclosure of which is incorporated herein by reference.

TECHNICAL FIELD

The invention relates generally to a slide staining apparatus and system. More particularly the invention relates to an automated system of staining slides comprising a biological sample.

BACKGROUND

In the field of medical diagnostics and research, the detection, identification, quantification, and characterization of cells of interest, such as cancer cells, through testing of biological samples is an important aspect of diagnosis and research. Typically, a biological sample such as bone marrow, lymph nodes, peripheral blood, cerebrospinal fluid, urine, effusions, fine needle aspirates, peripheral blood scrapings or other biological materials are prepared by staining a sample to identify cells of interest.

In Fluorescent In Situ Hybridization (FISH) a fluorescently labeled oligonucleotide probe is added to a tissue sample on a microscope slide under conditions that allow for the probe to enter the cell and enter the nucleus. If the labeled sequence is complementary to a sequence in a cell on the slide a fluorescent spot will be seen in the nucleus when the cell is visualized on a fluorescent microscope. FISH has the advantage that the individual cells containing the DNA sequences being tested can be visualized in the context of the tissue.

Immunostaining techniques utilizing non-fluorescent techniques are also commonly used. Such techniques can include the formation of colored precipitates and enzyme based reaction to label a sample. The result of the staining provides, for example, a precipitate at a location comprising a particular biological molecule, cell, or characteristic of interest.

Both non-fluorescent and fluorescent manual staining techniques are time consuming, result in variability among samples, and often utilize hazardous reagents. To overcome these problems automated systems have been designed to introduce cost savings, uniformity of slide preparation, and reduction of errors. Automated slide stainers are widely used in pathology to stain tissue samples that have been cut with a microtome and placed on glass slides. One common type of automated slide stainer consists of a set of racks for holding slides flat over a drain pan and a robotic arm which can travel in x, y and z over the slides. The arm carries a set of fluid dispensers. Some of these are connected to pumps that dispense a single fluid such as buffer. Others are connected to valves and can be used to dispense several fluids and some may have syringe pumps attached so they can draw and dispense fluids from vials prepositioned under the arm's range of motion. Descriptions of exemplary automatic slide stainers can be found in U.S. Pat. Nos. 6,352,861; 6,183,693; 6,349,264; and 6,180,061, the contents of which incorporated herein by reference in their entirety. There are several limiting factors to these designs including (1) that it is helpful to be able to control where the reagent is placed relative to the tissue sample, and (2) some fluids such as wash buffers are poured on the slide in excess and allowed to flow off the sides of the slide into the drain but others such as custom synthesized antibodies for IHC stains are very expensive. Typically just enough of these expensive reagents to cover the tissue sample is dripped onto the slide and held in place by surface tension.

SUMMARY

The invention provides a method for automated staining of a biological sample on a substrate. The method includes forming an image of the biological sample on the substrate; identifying a region to be stained comprising the biological sample; and dispersing a reagent on to the region to be stained. In one aspect of the invention, the method further comprises identifying a staining characteristic of the biological sample and dispensing the reagent on to the region to be stained based upon the staining characteristic. The automated stainer may use individual microscope slides as a substrate or may utilize carriers comprising multiple slides. Images acquired by the automated staining method can be high or low magnification images of the biological sample. In yet another aspect of the invention the method further comprises marking the region to be stained by surrounding the biological sample with a hydrophobic medium.

The invention also provide an apparatus comprising an imaging camera; a stage; at least one reagent container; at least one reagent dispenser device for dispensing a reagent from the at least one reagent container; a dispenser relocation device for moving the dispenser and/or stage relative to one another; and a computer. The imaging camera is in communication with the computer and is operable to image a slide on the stage and determine a processing parameter for the slide. The computer comprises an algorithm on a computer readable medium for instructing the computer to determine a location and an area comprising a biological sample on the slide, instructing the dispenser relocation device to relocate the dispenser to the area comprising the biological sample and dispensing a reagent from the reagent container in accordance with the processing parameter. In one aspect of the invention the apparatus further comprises a tracer device.

BRIEF DESCRIPTION OF THE DRAWINGS

The above and other features of the invention including various novel details of construction and combinations of parts will now be more particularly described with reference to the accompanying drawings. It will be understood that the particular apparatus embodying the invention is shown by way of illustration only and not as a limitation of the invention. The principles and features of this invention may be employed in varied and numerous embodiments without departing from the scope of the invention.

FIG. 8b is a bottom view of the slide carrier of FIG. 8a.

DETAILED DESCRIPTION

Figure 1A:
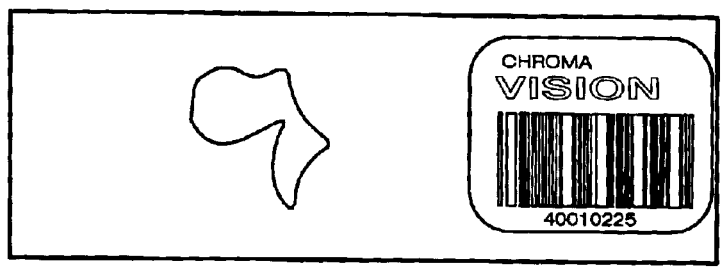
FIGS. 1A–1E depict slides containing a biological sample.
Figure 1B:
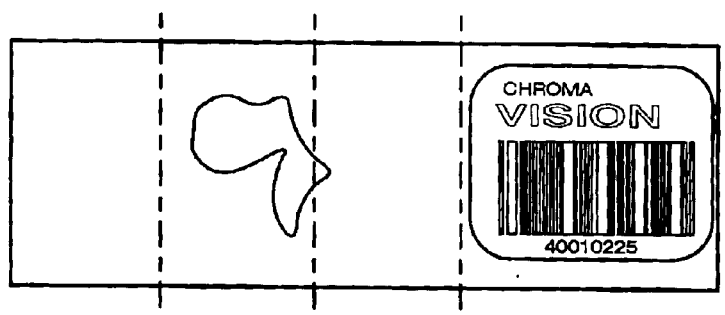
Figure 1C:
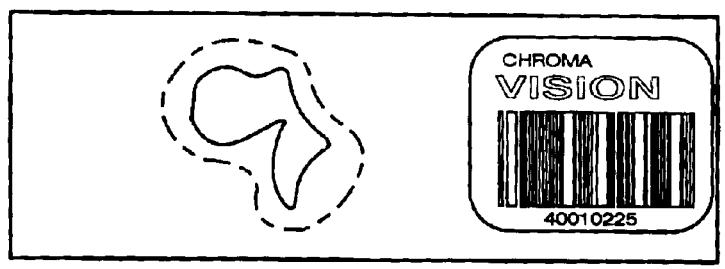
Figure 1D:
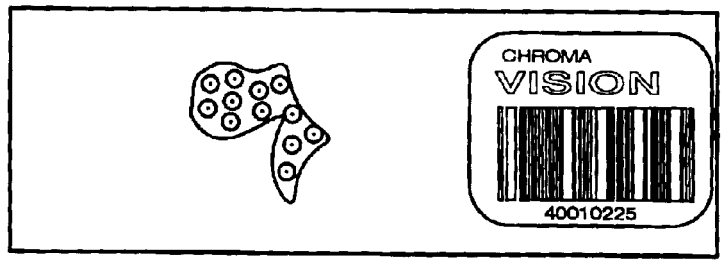
Figure 1E:
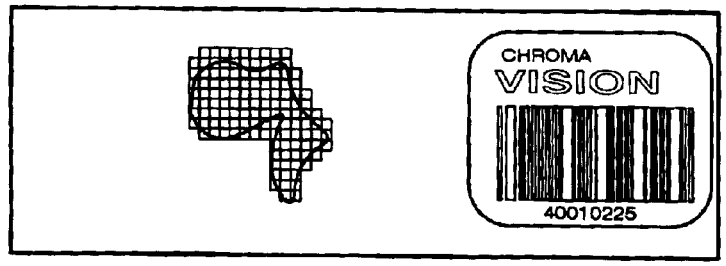

To achieve the greatest optimization of stain usage with an automated stainer, it is necessary to manually enter the location of the tissue sample on the slide into an automated stainer's database. The more detail contained in the location description, the more reagent may be saved by limiting the amount of reagent that needs to be dispensed. The reduction in dispensed reagent saves money and protects the environment from having to dispose of large quantities of, sometimes toxic, reagent material. However, adding detail to the description also makes the entry process more laborious and error prone. As shown in FIG. 1 a slide can be divided into a plurality of regions, for example, three regions. A biological sample on a slide will often fall within the boundary defining a region on the slide. Accordingly, as depicted in FIG. 1 a savings in reagent may be 33% relative to covering the whole slide. Current techniques to limit a reagent to just the region containing the biological sample are performed by technicians that manually draw a line around the biological sample with a grease pencil to ensure that the valuable reagent stays in place. This creates a surface tension barrier that holds the droplet of reagent over the tissue. It would, therefore, be desirable to quickly and accurately determine the actual boundaries of the tissue in order to calculate exactly the amount of reagent and dispensing area to stain the tissue.

Dispensers of reagents can be programmed to move in very small increments (approximately 0.2 mm to 1 mm or more) and can accurately dispense very small quantities. A video camera and light added to the XY arm of an automated stainer can be used to direct the movement of the dispenser. Since the camera and light can be prefocused at the distance from the XY arm to the slides they would not need to have any capacity for movement in the Z direction. However the capacity to move in the Z direction can be included where desired. It will be recognized by one of skill in the art that the location of the camera may be anywhere that provides for the capability of imaging a sample on the slide.

The camera can serve several functions. For example, the camera can be used to read a bar code, or other identifier, on a slide or slide rack. This bar code could either be a code or text string identifying what stain should be used on the slide, or it could be a unique code used to look up the desired stain in a pre-created database. In addition or alternatively, the camera can form an image of the unstained biological sample on the slide. This image could be processed by image analysis software and the exact size and position of the biological sample determined including any distinctive features defining an orientation of the biological sample. Given this information, a path for the dispenser and a flow rate can be calculated which would exactly cover the biological sample. In yet another aspect, the camera may provide, in addition to the features above, information regarding the exact outline of the tissue thus providing the ability of a tracer device to draw a bounding outline in a hydrophobic medium.

The image obtained for automated slide staining can have further uses. After staining a slide, the slide can be examined by an automated microscope with a motorized stage, which collects and stores images of the tissue. An example of such an automated microscope system is the ACIS™ available from Chroma Vision Medical Systems, Inc. (see, e.g., U.S. Pat. Nos. 6,215,892; 6,404,916; and 6,418,236, the contents of which are incorporated herein by reference in their entirety). Typically, automated imaging systems do an initial low-magnification scan of a slide to find the boundary of a biological sample so that the scan path to collect images of the tissue can be optimized. Where a low-magnification image is acquired by the automated microscope system, the process of acquiring these images takes image acquisition time. Another reason to do an initial scan is to choose focus points. Since the slide is flat, it is not necessary to re-focus for each image to be taken. An automated microscope system may choose a few (3–9 typically) points on the tissue and take a series of images at each point while scanning through the Z-axis. Using algorithms a focus plane in the Z-axis can be defined to provide an optimal focus. For example, given a set of optimal Z coordinates and a plurality of XY coordinate, a focus plane can be fit to the biological sample. However, in order to derive a focus plane, the system must know boundaries of the biological sample on the slide in order to choose a focus points within a biological sample.

Accordingly, the staining apparatus and methods described herein provide the opportunity to satisfy a low magnification image acquisition process and/or focus requirement during a staining process that can be utilized by an automated microscope system for later processing and imaging of a biological sample, thereby reducing processing time. For example, the hardware (e.g., the camera and computer system) used to collect images of a biological sample can be combined with an automated staining system as provided herein, wherein the images acquired during staining can be used by the automated microscope to increase processing speeds. The images acquired by the staining system provided herein are shared with the automated microscope system by making a data connection between the stainer and the automated microscope system. Images from the staining system can be stored on the staining system, on the automated microscope system, and/or on a third storage device that can be remotely located. The connection could be simply a standard network connection. The following steps would provide the required data sharing and usage.

1) A computer readable label with a unique barcode or OCR string of characters is affixed to each slide. Alternatively, the user places the samples on pre labeled slides.
2) The text or code of the label and the specific staining procedures are referenced in a database. This data would include the exact type of staining the automated stainer should do on the given slide and the type and detail of the scan the automated microscope should do. Note that it is not necessary for the label to actually name these tasks. All that is needed on the label is a unique code string that can be used as a key to search the database for the tasks to be done on a given slide.
3) A camera on the autostainer is used to read the label and process the staining characteristics or processing characteristics in a look-up database. The camera can also be used to make a low-resolution image of the tissue on the slide. The field of view of this image can include the edges of the slide so the position of the tissue on the slide can be calculated. The image would not need to include detail of the tissue, but just enough resolution to tell that tissue is present. In addition to using the image to optimize reagent placement as described above, the autostainer could write the image to the database labeled with the text of the slide's label.
4) Once the slides are stained and a coverslip(s) applied, the slides can be loaded into the automated microscope.
5) The automated microscope has a reader capable of reading the labels on the slides. As it loads each slide, it reads the label and use the text or code of the label to look up in a database the desired type of scan.
6) The automated microscope can also use the label to look up a stored image of the slide obtained, for example, during the staining procedure.
7) Instead of doing a preliminary scan of the slide to find the tissue, the automated microscope uses the stored image to design a scan pattern which would cover all the locations with tissue in the minimal amount of time.
8) In addition to determining where to scan using the stored image from the autostainer, the microscope could use this image to determine where to focus.

In one general aspect, the invention is an apparatus for automatically staining slides including a base, at least one dispenser in direct or indirect communication with the base, and a camera in direct or indirect communication with the base, dispenser, or both. The camera is used to obtain images of specimens on a slide. These images can then be used to direct the application of appropriate reagents, such as staining reagent(s) from the dispenser(s) to a particular specimen.

The apparatus can further include a tracer for outlining the specimen on the slide. The outline of the specimen can be used to contain the staining reagents. The outline can be of a hydrophobic material, where the reagent is a hydrophilic material. Once the specimen is outlined, a reagent can be applied to the specimen.

In certain embodiments of the invention, the base can be movable in relation to the dispenser, so that only certain portions of the slides having a specimen are stained. In other embodiments, the dispenser can be movable in relation to the base. In still other embodiments, both the dispenser and the base can move in relation to the each other.

In certain embodiments, the dispenser can be used to dispense liquids. These liquids can be staining reagents. A single dispensing unit can be used to dispense multiple reagents from different reservoirs. Alternatively, the apparatus may have multiple dispensing unit for dispensing different reagents.

In certain embodiments, the apparatus includes a bar code reader for identifying the slide. In one aspect of the invention, the camera reads the bar code or other identifying mark on the slide. The bar code can include an image identifier, information relating to the sample, or information relating to the staining of the slide.

In another general aspect, a computer can used the images acquired by the camera to locate the specimen. The obtained location can then be used to adjust the location of the dispenser or base in relation to each other so that the dispenser dispenses a reagent onto the desired sample/region on the slide. The image can be used to direct a tracer to outline the specimens on the slide. The image can also be used as the initial scan of an automated cell imaging system.

In yet another general aspect, a system for automated slide analysis includes an automated slide stainer with a camera as well as an automated microscope and computer system capable of automatically analyzing the slide.

Still another general aspect of the invention includes a method of automatically staining slides including the steps of scanning an image of a slide, using the image to determine a region of the slide to be stained, and dispensing a staining reagent to the region, thereby staining a slide.

The autostainer can also be used to stain tissue microarrays. For example, the autostainer can acquire and image to identify the locations of each sample in the array. The autostainer can then locate the dispenser over each sample and dispense a single drop of reagent on to each sample respectively. The samples can be stained with the same reagent or different reagents. In one aspect, the surface tension of the liquid reagent holds the drop on the desired sample. In another aspect, a grid is drawn, based upon the acquired image, in a hydrophobic medium each square in the grid comprising a separate sample. A reagent is then dispensed into each grid. The reagent is retained in the desired grid due to the hydrophobic-hydrophilic interactions of the hydrophobic medium/hydrophilic reagent.

The method can further include the step of using the image to determine an outline of the region to be stained prior to staining and tracing an outline around the region.

The method can further include the step of identifying the image to the specimen on the slide. This can be done by a bar code, magnetic strip, or other known identifiers.

In still another aspect, the methods is for the automatic processing of a slide including the steps of scanning an image of a slide, using the image to determine a region of the slide to be stained, staining the region on the slide, and using the image to process the slides in an automated microscope analysis system.

In certain embodiments, the methods can be used to direct the lens of an automated microscope to focus points in order to calculate optimal Z levels of the region of interest on the slide.

Figure 2:
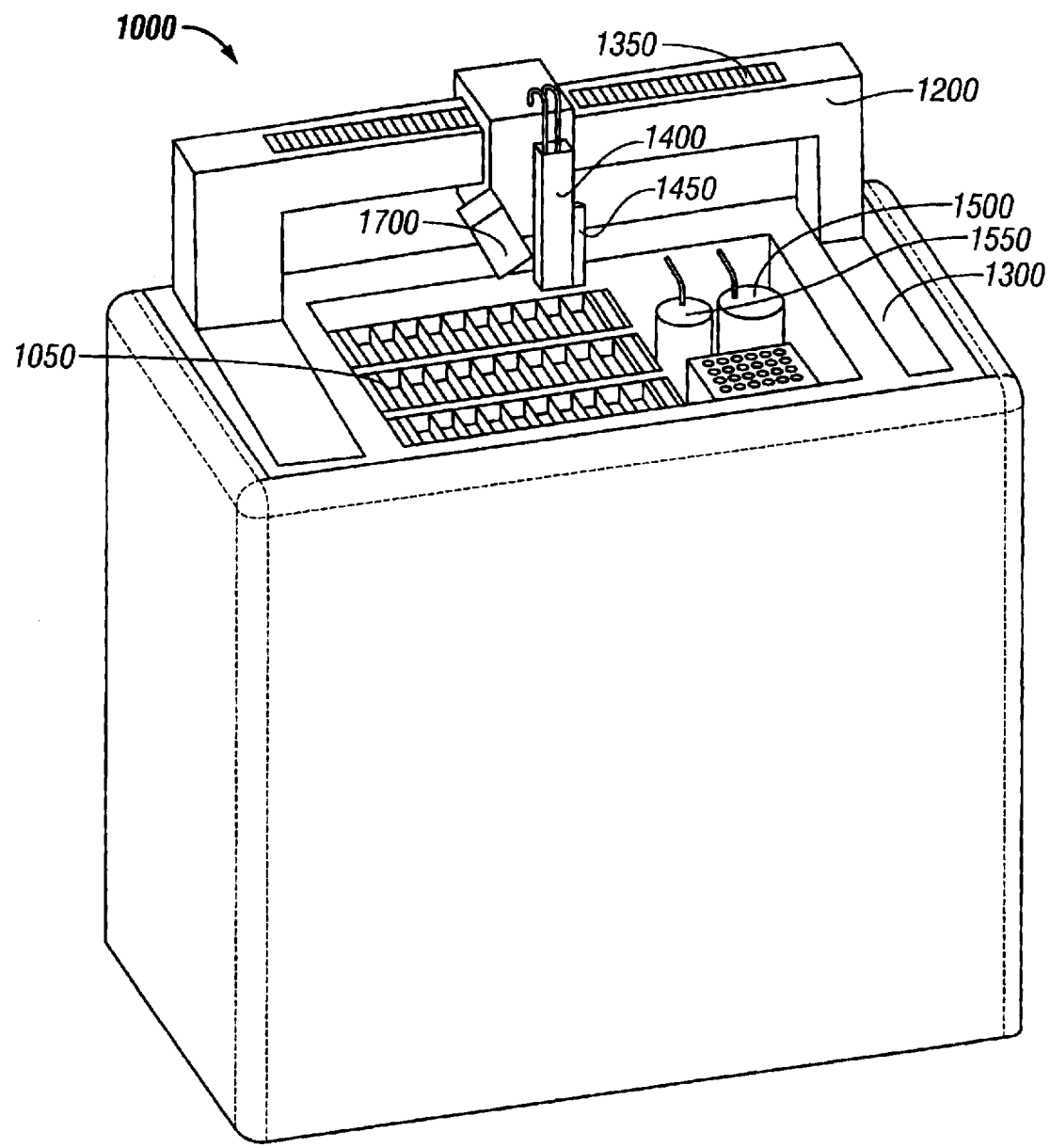
FIG. 2 shows an autostainer of the invention.

Referring to FIG. 2, the autostainer 1000 provided herein comprises a stage 1050 for supporting at least one slide (in certain aspects the stage supports a cassette capable of holding a plurality of slides). In yet another aspect, the stage 1050 is movable and can be associated with a slide carrier input hopper (see below). The stage optionally comprises at least one heating element 1100. For example, a plurality of heating elements may be present in the stage each capable of independent heating and temperature modulation. Alternatively, there can be a single heating element at a fixed location below the stage, wherein a slide is positionally located adjacent to the heating element thereby allowing the slide to be processed at a desired temperature.

The autostainer further comprises a positioning arm 1200. The positioning arm 1200 is movably located on an X-track 1300, which allows movement of the arm in an X-axis across the stage 1050. The positioning arm 1200 comprises a Y-track that allows for the positioning of a dispenser 1400 in a Y-axis. Accordingly, during operation the dispenser 1400 is capable of movement, relative to the stage, in both an X- and/or Y-axis, thereby allowing for the dispenser 1400 to be positionally located over a particular slide or position of the stage 1050. One of skill in the art will recognize that various modifications can be made to the overall design described herein without departing from the spirit of the invention. For example, the positioning arm may be movable in an X-Y and Z direction in the absence of "tracks" and can utilize various hinged and piviting members. In another alternative, the dispenser may be associated with the X-track rather than the Y-track as described above. Such variations are within the scope of the invention.

In some embodiments, the dispenser 1400 may further comprise a tracer 1450. The tracer 1450 comprises a hydrophobic medium (e.g., an oil or grease), wherein the tracer 1450 is capable of contacting the slide and tracing a line around a biological sample on the slide. Accordingly, the tracer 1450 is also capable of movement in the X- and/or Y-axis allowing for positioning the tracer 1450 near a biological sample on a slide and step-wise moving the tracer in an X- and/or Y-direction to trace a line of hydrophobic medium around the biological sample.

The autostainer also comprises at least one reagent reservoir 1500. The reagent reservoir contains reagents used in staining a biological sample. Where a wash step is required a wash medium, such as water, may be contained in a reagent reservoir for rinsing the dispenser 1400 between different reagents. The reagents contained in the reagent reservoirs are pumped through tubing 1550 and to dispenser 1400 using a pump 1600.

The positioning arm 1200 may further comprise a camera 1700. The camera 1700 can be any number of commercially available camera-types and include various optical sensing array systems such as a CCD camera. The camera 1700 is positioned such that it can acquire an image of the slide on a stage 1050 of autostainer 1000. Various lenses may be optionally included in order to obtain magnified views of a the slide. The camera 1700 is in electrical communication with a computer system (described more fully below), which is capable of analyzing images acquired by the camera to determine an appropriate staining procedure as well as to determine the size and amount of reagent to be dispensed. The image can be processed to identify a border of a tissue sample on the slide thereby determining a staining area. Once the border of the tissue is identified, this information can then be used to draw a hydrophobic outline around the tissue sample, or plurality of tissue samples. In another aspect of the invention, the image acquired by the autostainer camera is stored on computer readable medium for later use by, for example, an automated tissue analysis system as described below.

The biological mechanisms of many diseases have been clarified by microscopic examination of tissue samples. Histopathological examination has also permitted the development of effective medical treatments for a variety of illnesses. In standard anatomical pathology, a diagnosis is made on the basis of cell morphology and staining characteristics. Tumor samples, for example, can be examined to characterize the tumor type and suggest whether the patient will respond to a particular form of chemotherapy. Microscopic examination and classification of tissue samples stained by standard methods (such as hematoxylin and eosin) has improved cancer treatment significantly.

In manual scoring applications, the time it takes to collect an image is small relative to the time a user might spend in searching for the image on a slide. In fluorescent microscopy a fluorescent signal is used to identify a cell or candidate object of interest. However, while fluorescent signals can typically be seen with the naked eye when looking through a microscope, video cameras for imaging fluorescent slides, such as FISH slides, suffer from the disadvantage that an image will take from a fraction of a second to several seconds to locate and collect. In contrast, a microscope using transmitted light can collect a new image every 1/60th of a second. Thus, the time difference between imaging a fluorescent image and imaging an image in transmitted light for an entire slide will be significant. For example, a system could image all parts of a slide in 6 minutes in transmitted light, whereas it might take an hour or more to image under fluorescent conditions.

In addition, another problem with current automated fluorescent systems is the continued need for operator input to initially locate cell objects for analysis. Such continued dependence on manual input can lead to errors including cells or objects of interest being missed. Such errors can be critical especially in assays for so-called rare events, e.g., finding one tumor cell in a cell population of one million normal cells.

Additionally, manual methods can be extremely time consuming and can require a high degree of training to identify and/or quantify cells. This is not only true for tumor cell identification and detection, but also for other applications ranging from neutrophil alkaline phosphatase assays, reticulocyte counting and maturation assessment, and others. The associated manual labor leads to a high cost for these procedures in addition to the potential errors that can arise from long, tedious manual examinations.

In one aspect of the invention, an automated cell stainer and analysis system is provided. The invention provides an automated analysis system combined with an autostainer of the invention that quickly and accurately stains and scans biological material on a slide. For example, the autostainer can be used in conjunction with automated microscope systems to process biological samples. The autostainer can be linked to the autostainer in order to share processing parameter information and image information. A robotic arm can be used to move slides or slide cassettes between the autostainer (used for staining) and the microscope system's input hopper (see below). Such an automated process would allow for continued operation and processing of samples 24 hours a day, if so desired.

In another aspect of the invention, the system automates the analysis of fluorescent images on a slide quickly and accurately. Accordingly, the invention provides useful methods, apparatus, and systems for use in research and patient diagnostics to stain and locate cell objects for analysis having either or both of a non-fluorescent stain and a fluorescent indicator.

A biological sample and/or subsample comprises biological materials obtained from or derived from a living organism. Typically a biological sample will comprise proteins, polynucleotides, organic material, cells, tissue, and any combination of the foregoing. Such samples include, but are not limited to, hair, skin, tissue, cultured cells, cultured cell media, and biological fluids. A tissue is a mass of connected cells and/or extracellular matrix material (e.g., CNS tissue, neural tissue, eye tissue, placental tissue, mammary gland tissue, gastrointestinal tissue, musculoskeletal tissue, genitourinary tissue, and the like) derived from, for example, a human or other mammal and includes the connecting material and the liquid material in association with the cells and/or tissues. A biological fluid is a liquid material derived from, for example, a human or other mammal. Such biological fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

In one aspect of the invention, a biological sample may be divided into two or more additional samples (e.g., subsamples). Typically, in such an instance, the biological sample is a tissue, such as a tissue biopsy. The automated staining systems and analysis system disclosed herein is also capable of staining and analyzing tissue microarrays (e.g., a plurality of tissue samples on a single slide).

Typically, an individual sample used to prepare a subsample is embedded in embedding media such as paraffin or other waxes, gelatin, agar, polyethylene glycols, polyvinyl alcohol, celloidin, nitrocelluloses, methyl and butyl methacrylate resins or epoxy resins, which are polymerized after they infiltrate the specimen. Water soluble embedding media such as polyvinyl alcohol, carbowax (polyethylene glycols), gelatin, and agar, may be used directly on specimens. Water-insoluble embedding media such as paraffin and nitrocellulose require that specimens be dehydrated in several changes of solvent such as ethyl alcohol, acetone, or isopropyl alcohol and then be immersed in a solvent in which the embedding medium is soluble. In the case where the embedding medium is paraffin, suitable solvents for the paraffin are xylene, toluene, benzene, petroleum, ether, chloroform, carbon tetrachloride, carbon bisulfide, and cedar oil. Typically a tissue sample is immersed in two or three baths of the paraffin solvent after the tissue is dehydrated and before the tissue sample is embedded in paraffin. Embedding medium includes, for examples, any synthetic or natural matrix suitable for embedding a sample in preparation for tissue sectioning.

A tissue sample may be a conventionally fixed tissue sample, tissue samples fixed in special fixatives, or may be an unfixed sample (e.g., freeze-dried tissue samples). If a tissue sample is freeze-dried, it should be snap-frozen. Fixation of a tissue sample can be accomplished by cutting the tissue specimens to a thickness that is easily penetrated by fixing fluid. Examples of fixing fluids are aldehyde fixatives such as formaldehyde, formalin or formol, glyoxal, glutaraldehyde, hydroxyadipaldehyde, crotonaldehyde, methacrolein, acetaldehyde, pyruic aldehyde, malonaldehyde, malialdehyde, and succinaldehyde; chloral hydrate; diethylpyrocarbonate; alcohols such as methanol and ethanol; acetone; lead fixatives such as basic lead acetates and lead citrate; mercuric salts such as mercuric chloride; formaldehyde sublimates; sublimate dichromate fluids; chromates and chromic acid; and picric acid. Heat may also be used to fix tissue specimens by boiling the specimens in physiologic sodium chloride solution or distilled water for two to three minutes. Which ever fixation method is ultimately employed, the cellular structures of the tissue sample must be sufficiently hardened before they are embedded in a medium such as paraffin.

Using techniques such as those disclosed herein, a biological sample or a plurality of samples (e.g., from different subjects) comprising a tissue may be embedded, sectioned, and fixed. As discussed below, such subsamples can be examined under different staining or fluorescent conditions thereby rendering a wealth of information about the tissue biopsy.

In another aspect, the invention provides a method whereby a single biological sample may be assayed or examined in many different ways. Under such conditions a sample may be stained or labeled with a first agent using the automated staining system and examined by light microscopy with transmitted light and/or a combination of light microscopy and fluorescent microscopy. The sample can then but automatically stained or labeled with a second agent using the automated staining system and examined by light microscopy (e.g., transmitted light) and/or a combination of light microscopy and fluorescent microscopy.

The automated staining system of the invention maybe combined with automated microscope systems for analyzing biological samples. Accordingly, the invention provides methods of automated analysis of a biological sample comprising the automated staining systems of the invention. The biological sample and/or subsample can be contacted with a variety of agents useful in determining and analyzing cellular molecules and mechanisms. Such agents include, for example, polynucleotides, polypeptides, small molecules, and/or antibodies useful in in situ screening assays for detecting molecules that specifically bind to a marker present in a sample. Such assays can be used to detect, prognose, diagnose, or monitor various conditions, diseases, and disorders, or monitor the treatment thereof. An agent can be detectably labeled such that the agent is detectable when bound or hybridized to its target marker or ligand. Such means for detectably labeling any of the foregoing agents include an enzymatic, fluorescent, or radionuclide label. Other reporter means and labels are well known in the art. Reagents (such as those described above) are located in reservoir 1500 (see FIG. 2) and dispensed by dispenser 1400 onto the slide containing a sample.

A marker can be any cell component present in a sample that is identifiable by known microscopic, histologic, or molecular biology techniques. Markers can be used, for example, to distinguish neoplastic tissue from non-neoplastic tissue. Such markers can also be used to identify a molecular basis of a disease or disorder including a neoplastic disease or disorder. Such a marker can be, for example, a molecule present on a cell surface, an overexpressed target protein, a nucleic acid mutation or a morphological characteristic of a cell present in a sample. Stains and agents that detect such markers can be dispensed from and stored in the dispensor vials or containers of the automated staining system. The staining conditions for a particular reagent may differ. The automated staining system can be programmed to dispense a desired reagent, incubate the reagent with the sample for a required period of time and at a desired temperature, and then wash the reagent from the sample (if required).

An agent useful in the methods of the invention can be an antibody. Antibodies useful in the methods of the invention include intact polygonal or monoclonal antibodies, as well as fragments thereof, such as Fab and F(ab')2. For example, monoclonal antibodies are made from antigen containing fragments of a protein by methods well known to those skilled in the art (Kohler, et al., Nature, 256:495, 1975). Fluorescent molecules may be bound to an immunoglobulin either directly or indirectly by using an intermediate functional group. For example, the automated staining system of the invention can be programmed to dispense an antibody on to a biological sample on a slide and the incubate the antibody and the biological sample on the slide under appropriate conditions (e.g., under appropriate temperature and time period).

An agent useful in the methods of the invention can also be a nucleic acid molecule (e.g., an oligonucleotide or polynucleotide). For example, in situ nucleic acid hybridization techniques are well known in the art and can be used to identify an RNA or DNA marker present in a sample or subsample. Screening procedures that rely on nucleic acid hybridization make it possible to identify a marker from any sample, provided the appropriate oligonucleotide or polynucleotide agent is available. For example, oligonucleotide agents, which can correspond to a part of a sequence encoding a target polypeptide (e.g., a cancer marker comprising a polypeptide), can be synthesized chemically or designed through molecular biology techniques. The polynucleotide encoding the target polypeptide can be deduced from the genetic code, however, the degeneracy of the code must be taken into account. For such screening, hybridization is typically performed under in situ conditions known to those skilled in the art. The automated staining system of the invention can dispense an appropriate oligonucleotide or polynucleotide labeled with a reactive moiety on to a biological sample on a slide. The slide is then incubated under appropriate conditions and for a period of time sufficient to allow the labeled probe to interact with its complement nucleic acid molecule in the biological sample. Such conditions and periods of time are known to those of skill in the art and will depend upon such factors as the length and G/C content of the probe molecule as well as the type and preparation of the sample. Such information can be identified for the automated system in the text/bar-code label affixed to a particular slide containing the biological sample.

Figure 3:
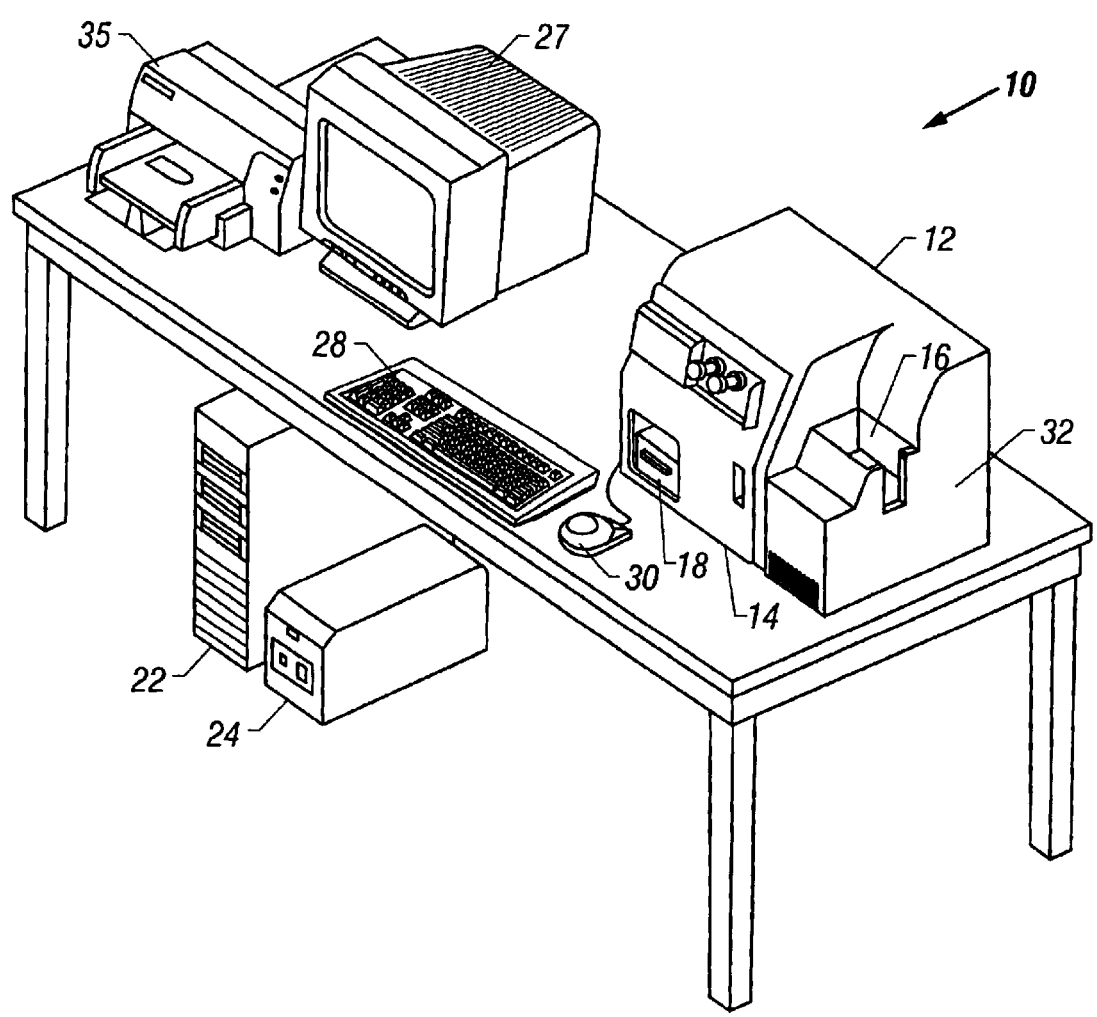
FIG. 3 is a perspective view of an exemplary apparatus for automated cell analysis embodying an imaging apparatus that may be used in combination with an autostainer of the invention.
Figure 4:
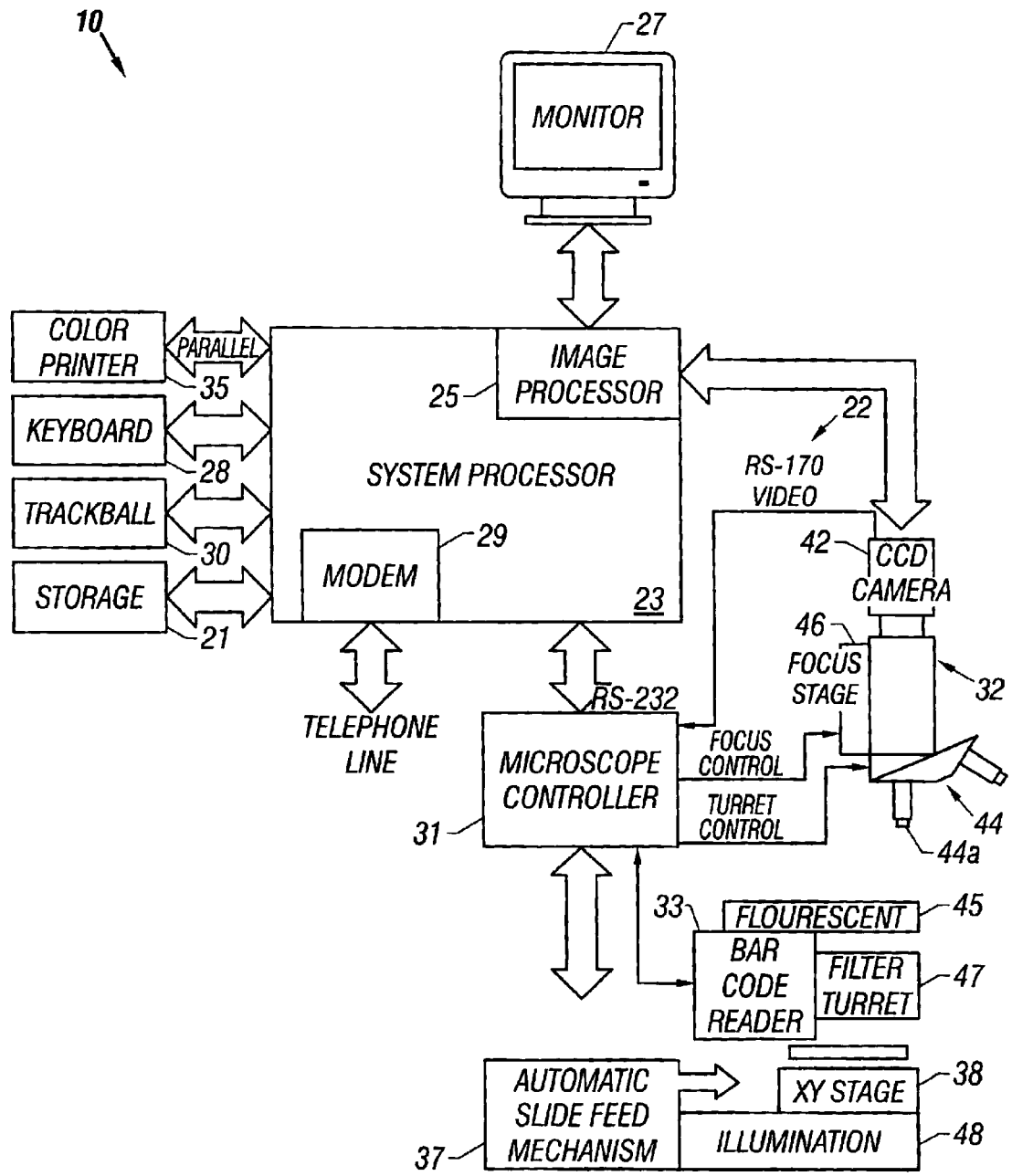
FIG. 4 is a block diagram of the apparatus shown in FIG. 3.

Referring now to FIGS. 3 and 4, an apparatus for automated cell analysis of biological samples is generally indicated by reference numeral 10 as shown in perspective view in FIG. 3 and in block diagram form in FIG. 4. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having at least one system processor 23, and a communications modem 29. The computer subsystem further includes a computer/image monitor 27 and other external peripherals including storage device 21, a pointing device, such as a track ball or mouse device 30, a user input device, such as a touch screen, keyboard, or voice recognition unit 28 and color printer 35. An external power supply 24 is also shown for power outage protection. The apparatus 10 further includes an optical sensing array 42, such as, for example, a CCD camera, for acquiring images. Microscope movements are under the control of system processor 23 through a number of microscope-subsystem functions described further in detail. An automatic slide feed mechanism in conjunction with X-Y stage 38 provide automatic slide handling in the apparatus 10. An illumination 48 comprising a bright field transmitted light source projects light onto a sample on the X-Y stage 38, which is subsequently imaged through the microscope subsystem 32 and acquired through optical sensing array 42 for processing by the system processor 23. A Z stage or focus stage 46 under control of the system processor 23 provides displacement of the microscope subsystem in the Z plane for focusing. The microscope subsystem 32 further includes a motorized objective turret 44 for selection of objectives.

The apparatus 10 may optionally include a fluorescent excitation light source 45 and may further include a plurality of fluorescent filters on a turret or wheel 47. Alternatively, a filter wheel may have an electronically tunable filter. In one aspect, fluorescent excitation light from fluorescent excitation light source 45 passes through fluorescent filter 47 and contacts a sample on the XY stage 38. Fluorescent light emitted from a fluorescent agent contained on a sample passes through objective 44a to optical sensing array 42. The fluorescent emission light forms an image that is digitized by an optical sensing array 42 and the digitized image is sent to an image processor 25 for subsequent processing.

The purpose of the apparatus 10 is for the automatic scanning of prepared microscope slides for the detection of candidate objects of interest such as normal and abnormal cells, e.g., tumor cells. In one aspect, the apparatus 10 is capable of detecting rare events, e.g., event in which there may be only one candidate object of interest per several hundred thousand objects, e.g., one to five candidate objects of interest per 2 square centimeter area of the slide. The apparatus 10 automatically locates and can count candidate objects of interest noting the coordinates or location of the candidate object of interest on a slide based upon color, size and shape characteristics. A number of stains can be used to stain candidate objects of interest and other objects (e.g., normal cells) different colors so that such cells can be distinguished from each other (as described herein).

Figure 10:
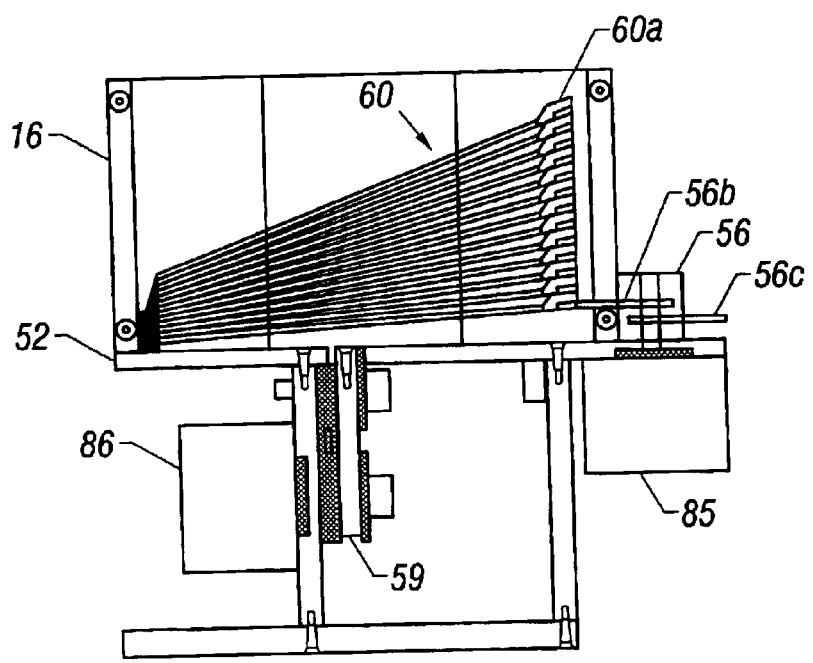
FIG. 10 is an end view of the input module of the automated slide handling subsystem.
Figure 10A:
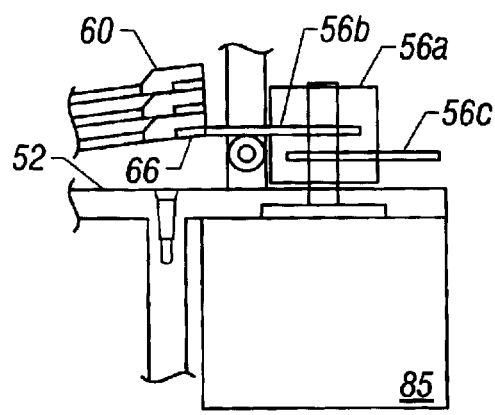
FIGS. 10a–10d illustrate the input operation of the automatic slide handling subsystem.
Figure 10B:
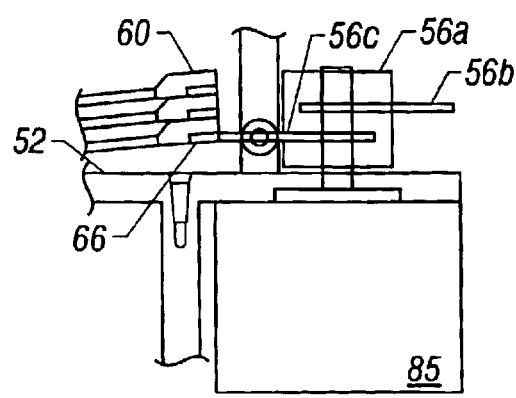

A biological sample may be prepared with a reagent to obtain a colored insoluble precipitate. As one step in the methods and systems of the invention an apparatus 10 is used to detect this precipitate as a candidate object of interest. During operation of the apparatus 10, a pathologist or laboratory technician mounts slides onto slide carriers. A slide carrier 60 is illustrated in FIG. 10 and will be described further below. Each slide carrier can be designed to hold a number of slides from about 1–50 or more (e.g., the holder depicted in FIG. 10 holds up to 4 slides). A number of slide carriers are then loaded into input hopper 16 (see FIG. 3). The operator can specify the size, shape and location of the area to be scanned or alternatively, the system can automatically locate an area. The operator then commands the system to begin automated scanning of the slides through a graphical user interface. Unattended scanning begins with the automatic loading of the first carrier and slide onto the precision motorized X-Y stage 38. In one aspect of the invention, a bar code label affixed to the slide or slide carrier is read by a bar code reader 33 during this loading operation. Where an image of the sample has been acquired by the autostainer the computer system uses the barcode to look up the image and any corresponding data stored about the sample (e.g., data such as a low magnification image, the processing parameters, the subject information, and the like). Each slide is then scanned a desired magnification, for example, 10×, to identify candidate cells or objects of interest based on their color, size and shape characteristics. The term "coordinate" or "address" is used to mean a particular location on a slide or sample. The coordinate or address can be identified by any number of means including, for example, X-Y coordinates, r-θ coordinates, polar, vector or other coordinate systems known in the art. In one aspect of the invention a slide is scanned under a first parameter comprising a desired magnification and using a bright field light source from illumination 48 (see FIG. 4) to identify a candidate cell or object of interest.

The methods, systems, and apparatus of the invention may obtain a low magnification image of a candidate cell or object of interest and then return to each candidate cell or object of interest based upon the previously stored coordinates to reimage and refocus at a higher magnification such as 40× or to reimage under fluorescent conditions. In one aspect of the invention, the low magnification image is acquired during the cell staining procedure using the camera associated with the automated staining system. The image acquired by the staining system may be stored and utilized by the image analysis software to identify the location, orientation, and/or the location of possible candidate objects of interest in the sample.

To avoid missing candidate cells or objects of interest, the system can process low magnification images by reconstructing the image from individual fields of view and then determine objects of interest. In this manner, objects of interest that overlap more than one objective field of view may be identified. This is particularly useful when analyzing slides that comprise an array of tissue samples. The apparatus comprises a storage device 21 that can be used to store an image of a candidate cell or object of interest for later review by a pathologist or to store identified coordinates for later use in processing the sample or a subsample. The storage device 21 can be a removable hard drive, DAT tape, local hard drive, optical disk, or may be an external storage system whereby the data is transmitted to a remote site for review or storage. In one aspect, stored images (from both fluorescent and bright field light) can be overlapped and viewed in a mosaic of images for further review (as discussed more fully herein).

Apparatus 10 can also be used for fluorescent imaging (e.g., in FISH techniques) of prepared microscope slides for the detection of candidate objects of interest such as normal and abnormal cells, e.g., tumor cells. The apparatus 10 automatically locates the coordinates of previously identified candidate cells or objects of interest based upon the techniques described above. In this aspect, the slide has been contacted with a fluorescent agent labeled with a fluorescent indicator. The fluorescent agent is an antibody, polypeptide, oligonucleotide, or polynucleotide labeled with a fluorescent indicator. A number of fluorescent indicators are known in the art and include DAPI, Cy3, Cy3.5, Cy5, Cy5.5, Cy7, umbelliferone, fluorescein, fluorescein isothiocyanate (FITC), rhodamine, dichlorotriazinylamine fluorescein, dansyl chloride or phycoerythrin. In another aspect of the invention a luminescent material may be used. Useful luminescent materials include luminol; examples of bioluminescent materials include luciferase, luciferin, and aequorin. The fluorescent and luminescent agents can be stored and dispensed from reservoir 1500 and dispenser 1400, respectively, or the autostainer.

A fluorescent indicator should have distinguishable excitation and emission spectra. Where two or more fluorescent indicators are used they should have differing excitation and emission spectra that differ, respectively, by some minimal value (typically about 15–30 nm). The degree of difference will typically be determined by the types of filters being used in the process. Typical excitation and emission spectra for DAPI, FITC, Cy3, Cy3.5, Cy5, Cy5.5, and Cy7 are provided below:

| Fluorescent indicator | Excitation Peak | Emission Peak |
| --- | --- | --- |
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

A biological sample is prepared with a fluorescently labeled agent or luminescently labeled agent to identify molecules of interest within the biological sample. In one aspect of the invention, the autostainer is used to dispense a fluorescently-labeled or luminescent-labeled agent onto a biological sample. The fluorescently and/or luminescently labeled agent are stored in the reservoir 1500. A bar code is read by a camera 1700 or a bar code reader and used to determine the staining parameter (e.g., what reagent to use). The camera 1700 optionally obtains an image of the slide in order to determine a region containing a sample to be contacted with a fluorescent or luminescent agent. The image is processed using the algorithms and imaging techniques described herein. In one aspect of the invention, a grease pen is then used to outline the region to be contacted with the agent. The outline is generated by contacting the slide with the grease pen and then moving the stage supporting the slide in X-Y directions under the grease pen. The outlining of the region will assist in limiting the amount of agent needed to be used to label the sample on the slide. A dispenser 1400 then dispenses the desired fluorescent and/or luminescent reagent onto the sample.

An imaging apparatus is then used to detect the fluorescence or luminescence of the molecule when exposed to a wavelength that excites a fluorescent indicator attached to the fluorescent agent or exposed to conditions that allow for luminescence. The automated system of the invention scans a biological sample contacted with a fluorescently agent under conditions such that a fluorescent indicator attached to the agent fluoresces, or scans a biological sample labeled with a luminescent agent under conditions that detects light emissions from a luminescent indicator. Examples of conditions include providing a fluorescent excitation light that contacts and excites the fluorescent indicator to fluoresce. As described in more detail herein such an imaging apparatus includes a fluorescent excitation light source and can also include a number of fluorescent excitation filters to provide different wavelengths of excitation light. A bar code label affixed to a slide or slide carrier is read by a bar code reader 33 during a loading operation on to the autostainer and/or imaging apparatus (e.g., the optical subsystem of an automated imaging system). The bar code provides the system with information including, for example, information about the staining and/or scanning parameters, including the type of stain, light source, or the excitation light wavelength to use. Each slide is then scanned at a desired magnification, for example, 10×, to identify candidate cells or objects of interest based on their color, size, and shape characteristics. Where the location of candidate cells or objects of interest have been previously identified, the location, coordinate, or address of the candidate cells or objects of interest (including corrected coordinates where more than one sub-sample is analyzed) are used to focus the system at those specific locations and obtain fluorescent or bioluminescent images. In one aspect of the invention, various wavelengths of light may be associated with a light source on the automated staining system. In this aspect of the invention, where a fluorescent agent is dispensed onto a biological sample on the slide, the automated staining system can obtain an image under fluorescent conditions. This image can then be used, for example, in determining whether the sample has been contacted for sufficient time with the fluorescent agent in order to determine if the sample has been properly stained/processed. In addition, this low-magnification image acquired during staining can then be made available to the imaging analysis software of the automated imaging apparatus in identifying the locations of a sample and/or candidate objects of interest that fluoresce under appropriate conditions.

The automated imaging apparatus can obtain a first image using a transmitted light source at either a low magnification or high magnification of a sample, candidate cell, or object of interest and then return to the coordinates (or corrected coordinates) associated with the sample, each candidate cell, or object of interest in the same sample or a related sub-sample to obtain a fluorescent image. In order to reduce the processing time, the autostainer is capable of providing an image of the sample at a low or high magnification, the image being acquired during cell staining. The image acquired by the autostainer may be a transmitted light image or a fluorescent image (depending upon the type of stain/reagent used). Accordingly, a first image would no longer need to be acquired by an automated imaging apparatus as the image acquired by the autostainer serves a similar purpose and can be electronically shared with the imaging apparatus.

The transmitted and/or fluorescent/luminescent images can be stored on a storage device 21 that can be used to store an image of a sample, candidate cell, or object of interest for later review by a pathologist. A storage device may be present on the autostainer and/or the imaging apparatus. The storage device 21 can be a removable hard drive, DAT tape, local hard drive, optical disk, or may be an external storage system whereby the data is transmitted to a remote site for review or storage. For example, the image from the autostainer may be transmitted to the imaging apparatus for storage on a storage device associated with the imaging apparatus. In one aspect, stored images (from both fluorescent and bright field light) can be overlapped and viewed in a mosaic of images for further review (as discussed more fully herein).

Where both a transmitted light source and fluorescent light source are present, the light sources for both processes must be managed. In one aspect, a transmitted light source and a fluorescent light source may be present on the autostainer as well as the imaging apparatus. Light source management can be handled by a processor associated with the autostainer and/or the imaging apparatus. For example, such light source management is performed using the system processor 23 through the Fluorescent controller 102 and illumination controller 106 (see, FIG. 5). During processing of images in transmitted light microscopy the fluorescent excitation light source is off or blocked such that excitation light from the fluorescent light source does not contact the sample. When fluorescent images are being obtained the transmitted light source is off or blocked such that the transmitted light does not pass through the sample while the sample is contacted by fluorescent excitation light from fluorescent excitation light source 45.

Figure 5:
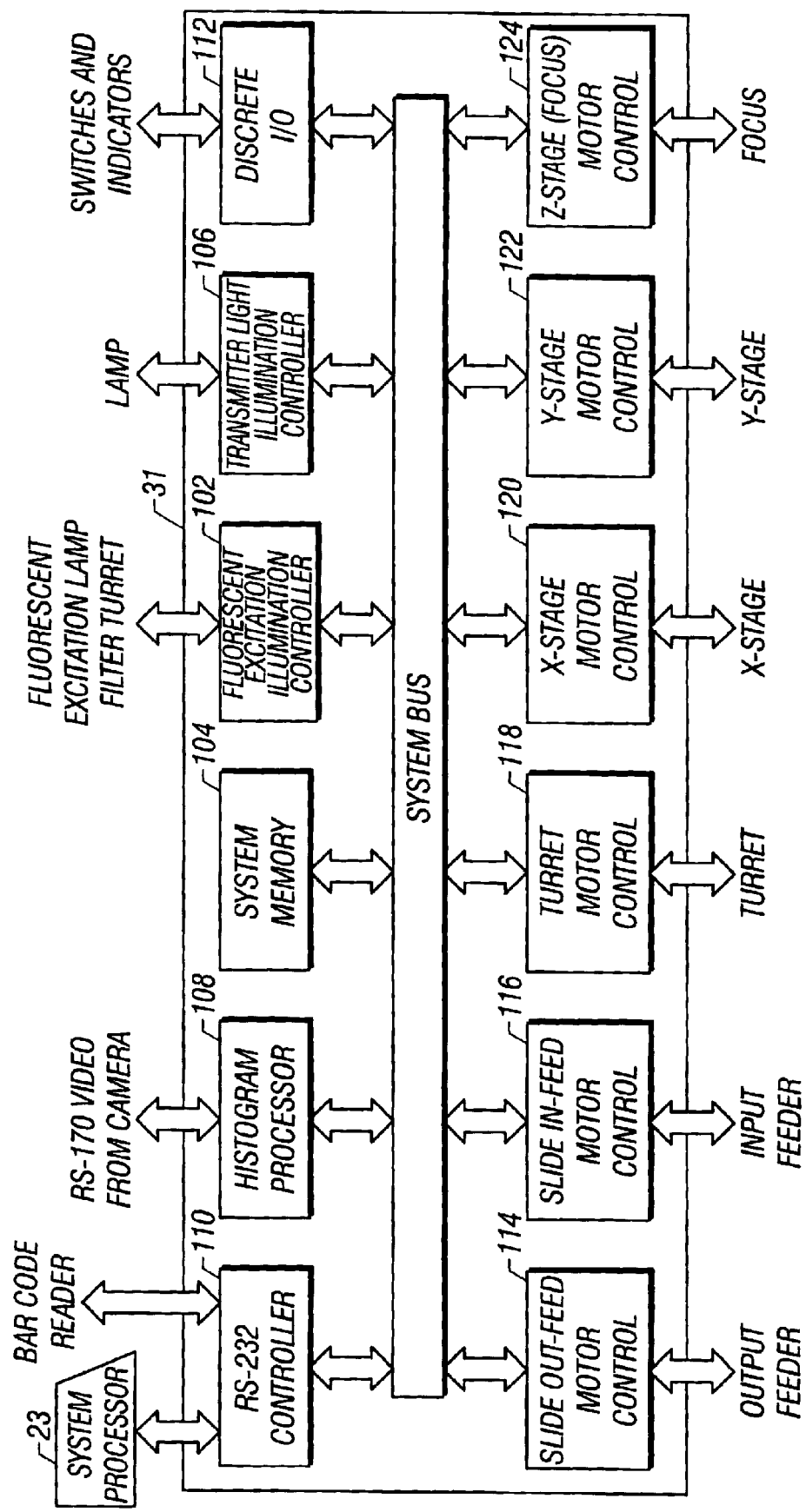
FIG. 5 is a block diagram of the system processor of FIG. 4.

Having described the overall operation of the imaging apparatus 10 from a high level, the further details of the imaging apparatus will now be described. Referring to FIG. 5, the microscope controller 31 is shown in more detail. The microscope controller 31 includes a number of subsystems. The apparatus system processor 23 controls these subsystems. The system processor 23 controls a set of motor—control subsystems 114 through 124, which control the input and output feeder, the motorized turret 44, the X-Y stage 38, and the Z stage 46 (FIG. 4). The system processor 23 further controls a transmitted light illumination controller 106 for control of substage illumination 48 bright field transmitted light source and controls a fluorescent excitation illumination controller 102 for control of fluorescent excitation light source 45 and/or filter turret 47. The transmitted light illumination controller 106 is used in conjunction with camera and image collection adjustments to compensate for the variations in light level in various samples. The light control software samples the output from the camera at intervals (such as between loading of slide carriers), and commands the transmitted light illumination controller 106 to adjust the light or image collection functions to the desired levels. In this way, light control is automatic and transparent to the user and adds no additional time to system operation. Similarly, fluorescent excitation illumination controller 102 is used in conjunction with the camera and image collection adjustments to compensate for the variations in fluorescence in various samples. The light control software samples the output from the camera at intervals (such as between loading of slide carriers and may include sampling during image collection), and commands the fluorescent excitation illumination controller 102 to adjust the fluorescent excitation light or image exposure time to a desired level. In addition, the fluorescent excitation illumination controller 102 may control the filter wheel or wavelength 47. The system processor 23 is a high performance processor of at least 200 MHz, for example, the system processor may comprise dual parallel, Intel, 1 GHZ devices. Advances in processors are being routinely made in the computer industry. Accordingly, the invention should not be limited by the type of processor or speed of the processor disclosed herein.

It is important to note that although the above description is in reference to the imaging apparatus 10, the processes and implementation are applicable to the autostainer as described above. For example, the same or similar processor can be used to manage the light source, the stage, and camera associated with the autostainer.

Figure 6:
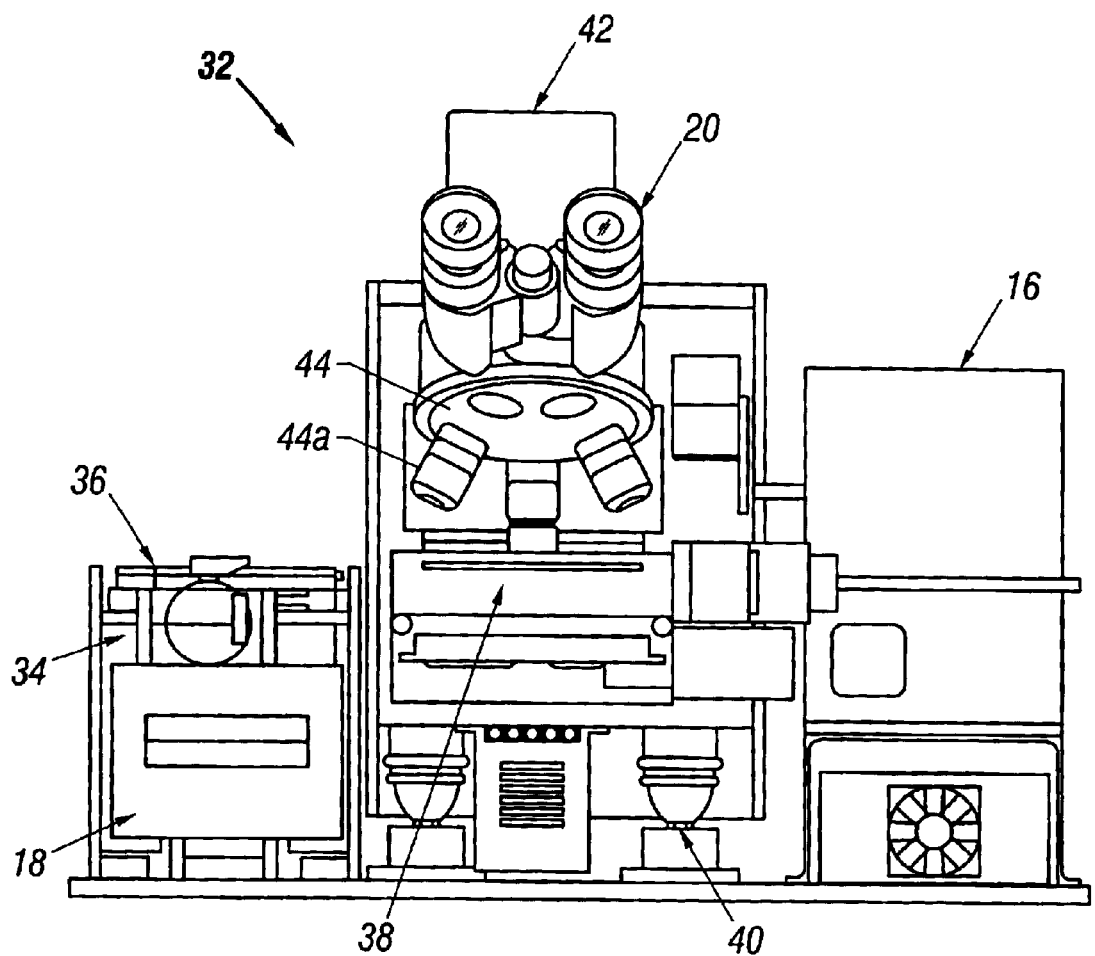
FIG. 6 is a plan view of the apparatus of FIG. 3 having the housing removed.
Figure 7:
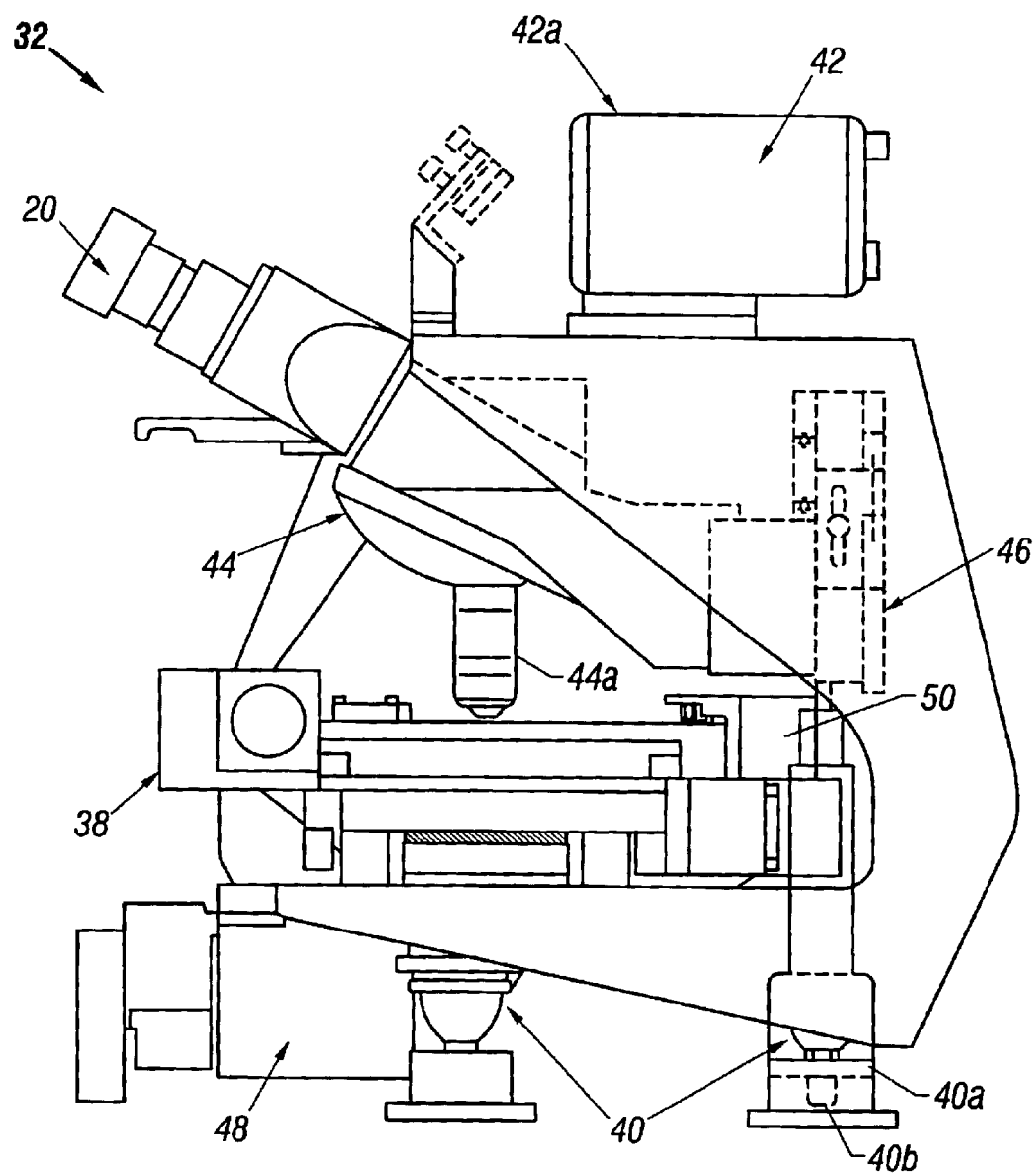
FIG. 7 is a side view of a microscope subsystem of the apparatus of FIG. 3.

Referring now to FIGS. 6 and 7, further detail of the imaging apparatus 10 is shown. FIG. 6 shows a plan view of the imaging apparatus 10 with the housing 12 removed. Shown is slide carrier unloading assembly 34 and unloading platform 36 which in conjunction with slide carrier output hopper 18 function to receive slide carriers which have been analyzed. Vibration isolation mounts 40, shown in further detail in FIG. 7, are provided to isolate the microscope subsystem 32 from mechanical shock and vibration that can occur in a typical laboratory environment. In addition to external sources of vibration, the high-speed operation of the X-Y stage 38 can induce vibration into the microscope subsystem 32. Such sources of vibration can be isolated from the electro-optical subsystems to avoid any undesirable effects on image quality. The isolation mounts 40 comprise a spring 40*a* and piston 40*b* (see FIG. 7) submerged in a high viscosity silicon gel which is enclosed in an elastomer membrane bonded to a casing to achieve damping factors on the order of about 17 to 20%. Other dampening devices are known in the art and may be substituted or combined with the dampening device provided herein. Occulars 20 are shown in FIGS. 6 and 7, however, their presence is an optional feature. The occulars 20 may be absent without departing from the advantages or functionality of the system.

Figure 8A:
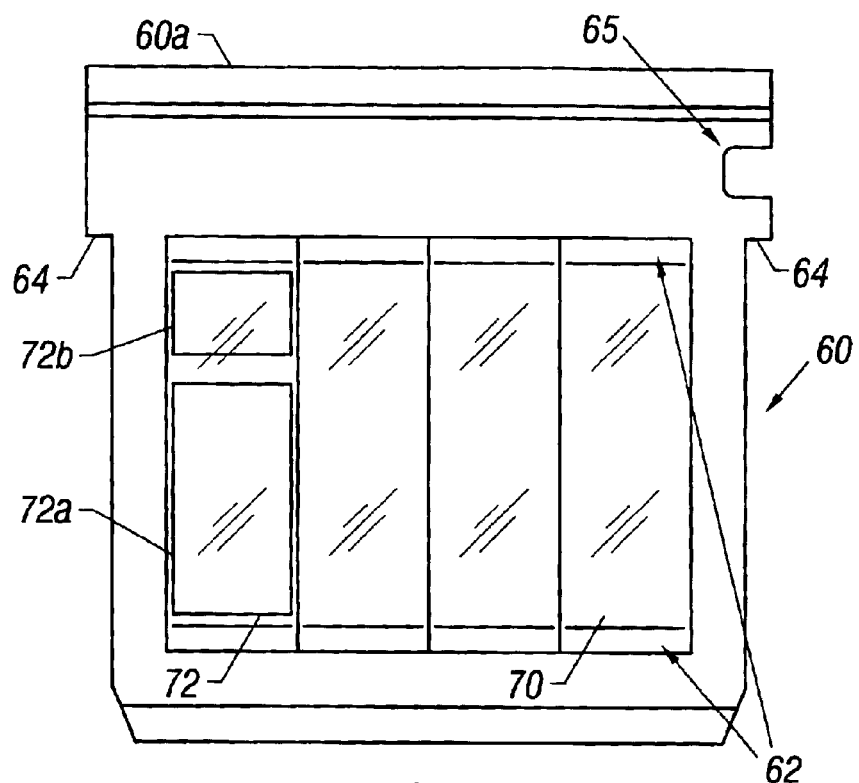
FIG. 8a is a top view of a slide carrier for use with the apparatus of FIG. 3.
Figure 8B:
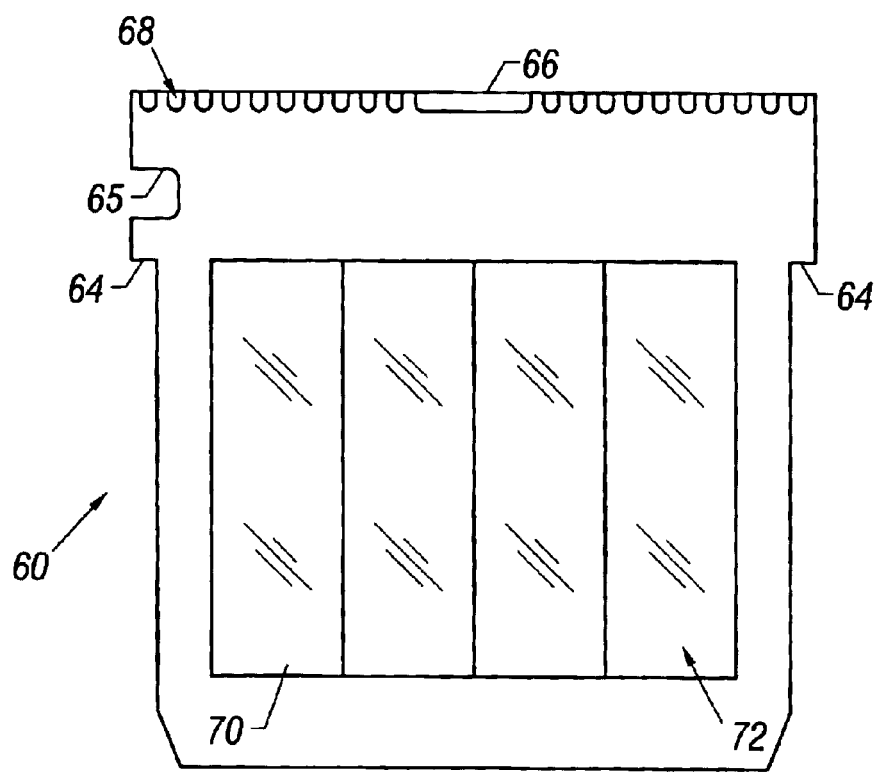

The automatic slide-handling feature of the invention will now be described. The automated slide handling subsystem operates the movement and management of a slide carrier. A slide carrier 60 is shown in FIGS. 8*a* and 8*b*, which provide a top view and a bottom view, respectively. The slide carrier 60 can include a number of slides 70 (e.g., at least four slides but may number from 1–50 or more). The carrier 60 includes ears 64 for hanging the carrier in the output hopper 18. An undercut 66 and pitch rack 68 are formed at the top edge of the slide carrier 60 for mechanical handling of the slide carrier. A keyway cutout 65 is formed in one side of the carrier 60 to facilitate carrier alignment. A prepared slide 72 mounted on the slide carrier 60 includes a sample area 72*a* and a bar code label area 72*b*.

The slide carrier 60 or a single slide may be processed for staining by the autostainer. In one aspect of the invention, an autostainer input hopper holds a plurality of slides or slide carriers that can be automatically fed to the autostainer stage. The slide carrier 60 is manually or automatically placed on the autostainer stage 1050. The stage 1050 is movable and can be associated with the slide carrier input hopper 16. The autostainer positioning arm 1200, then positions the arm using X-track 1300, which allows movement in an X-axis across the stage, and Y-track that allows for the positioning of a dispenser in an Y-axis. Accordingly, the dispenser 1400 is capable of movement, relative to the stage, in both an X- and/or Y-axis, thereby allowing for the dispenser 1400 to be positionally located over a particular slide or region of a slide or slide carrier. A camera 1700 associated with the positioning arm acquires an image or a bar code or of the slide on stage 1050. Various lenses may be optionally included in order to obtain magnified views of a the slide. The camera 1700 is in electrical communication with a computer system that analyzes images acquired by the camera to determine an appropriate staining procedure as well as to determine the size and amount of reagent to be dispensed. The image can be processed to identify a border of a tissue sample on the slide thereby determining a staining area. Once the border of the tissue is identified, this information can then be used to draw a hydrophobic outline around the tissue sample, or plurality of tissue samples. The tracer 1450 is also capable of movement in the X- and/or Y-axis allowing for positioning the tracer 1450 near a biological sample on a slide and step-wise moving the tracer in an X- and/or Y-direction to trace a line of hydrophobic medium around the sample. Once the image is acquired and the staining method identified as well as the location or the sample, at least one reagent reservoir 1500 containing reagents used in staining a biological sample, pumps the reagent through tubing 1550 and to dispenser 1400 using a pump 1600. The slide comprising the sample and the reagent are then incubated and heated according to the type of stain used. Once the slide is stained the slide or slide carrier 60 can be manually or automatedly placed into input hopper 16. Alternatively, an automated system may be used to move the slide or slide carrier 60 to input hopper 16. Examples of such automated systems include robotic arms, conveyor type belt systems and the like.

Figure 9A:
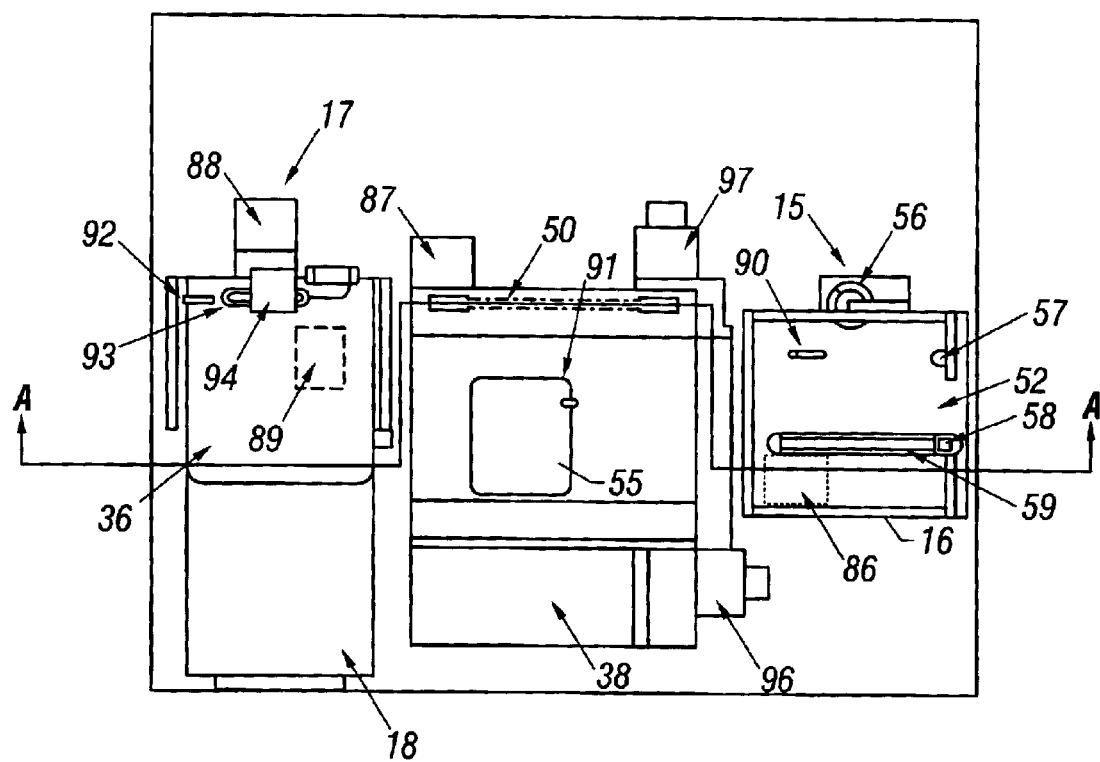
FIG. 9a is a top view of an automated slide handling subsystem of the apparatus of FIG. 3.
Figure 9B:
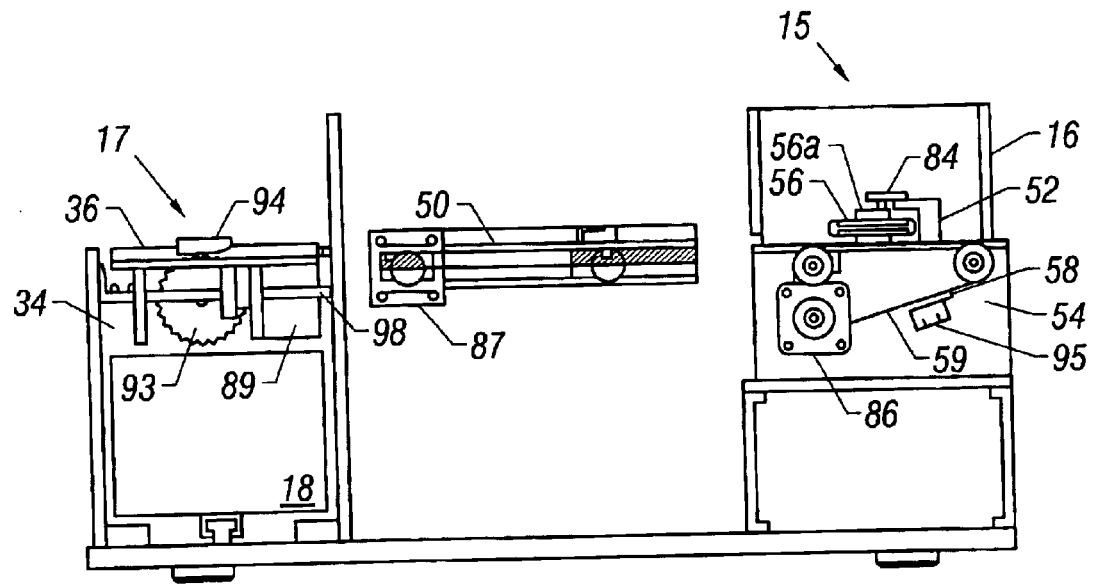
FIG. 9b is a partial cross-sectional view of the automated slide handling subsystem of FIG. 9a taken on line A—A.

FIG. 9*a* provides a top view of the slide handling subsystem, which comprises a slide, input module 15, a slide output module 17 and X-Y stage drive belt 50. FIG. 9*b* provides a partial cross-sectional view taken along line A—A of FIG. 9*a* The slide input module 15 comprises a slide carrier input hopper 16, loading platform 52 and slide carrier loading subassembly 54. The input hopper 16 receives a series of slide carriers 60 (FIGS. 8*a* and 8*b*) in a stack on loading platform 52. A guide key 57 (see FIG. 9*a*) protrudes from a side of the input hopper 16 to which the keyway cutout 65 (FIG. 8*a*) of the carrier is fit to achieve proper alignment. The input module 15 further includes a revolving indexing cam 56 and a switch 90 (FIG. 9*a*) mounted in the loading platform 52, the operation of which is described further below. The carrier loading subassembly 54 comprises an infeed drive belt 59 driven by a motor 86. The infeed drive belt 59 includes a pusher tab 58 for pushing the slide carrier horizontally toward the X-Y stage 38 when the belt is driven. A homing switch 95 senses the pusher tab 58 during a revolution of the belt 59. Referring specifically to FIG. 9*a*, the X-Y stage 38 is shown with x position and y position motors 96 and 97, respectively, which are controlled by the system processor 23 (FIG. 5) and are not considered part of the slide handling subsystem. The X-Y stage 38 further includes an aperture 55 for allowing illumination to reach the slide carrier. A switch 91 is mounted adjacent the aperture 55 for sensing contact with the carrier and thereupon activating a motor 87 to drive stage drive belt 50 (FIG. 9*b*). The drive belt 50 is a double-sided timing belt having teeth for engaging pitch rack 68 of the carrier 60 (FIG. 8*b*).

The slide output module 17 includes slide carrier output hopper 18, unloading platform 36 and slide carrier unloading subassembly 34. The unloading subassembly 34 comprises a motor 89 for rotating the unloading platform 36 about shaft 98 during an unloading operation described further below. An outfeed gear 93 driven by motor 88 (FIG. 9*a*) rotatably engages the pitch rack 68 of the carrier 60 (FIG. 8*b*) to transport the carrier to a rest position against switch 92 (FIG. 9*a*). A springloaded hold-down mechanism 94 holds the carrier in place on the unloading platform 36.

The slide handling operation will now be described. Referring to FIG. 10, a series of slide carriers 60 are shown stacked in input hopper 16 with the top edges 60*a* aligned. As the slide handling operation begins, the indexing cam 56 driven by motor 85 advances one revolution to allow only one slide carrier to drop to the bottom of the hopper 16 and onto the loading platform 52.

Figure 10C:
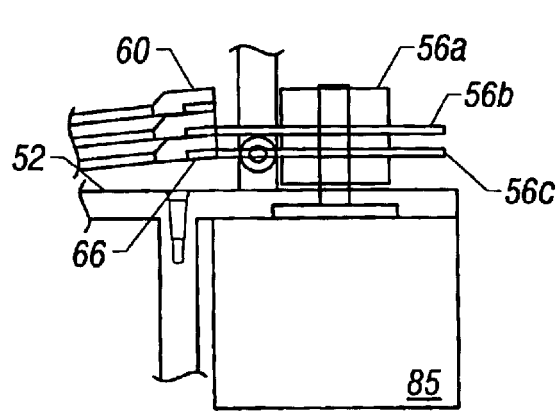
Figure 10D:
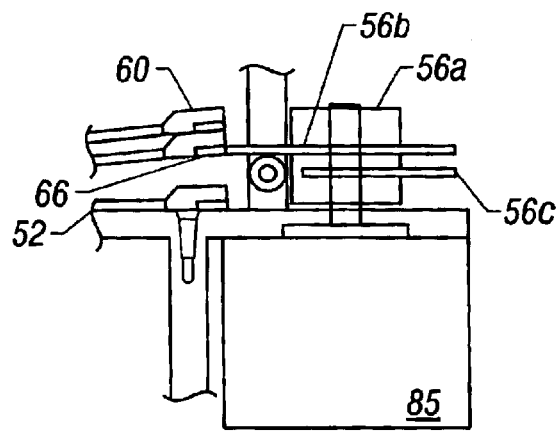

FIGS. 10*a*–10*d* show the cam action in more detail. The cam 56 includes a hub 56*a* to which are mounted upper and lower leaves 56*b* and 56*c*, respectively. The leaves 56*b* and 56*c* are semicircular projections oppositely positioned and spaced apart vertically. In a first position shown in FIG. 10*a*, the upper leaf 56*b* supports the bottom carrier at the undercut portion 66. At a position of the cam 56 rotated 180°, shown in FIG. 10*b*, the upper leaf 56*b* no longer supports the carrier and instead the carrier has dropped slightly and is supported by the lower leaf 56*c*. FIG. 10*c* shows the position of the cam 56 rotated 270° wherein the upper leaf 56*b* has rotated sufficiently to begin to engage the undercut 66 of the next slide carrier while the opposite facing lower leaf 56*c* still supports the bottom carrier. After a full rotation of 360° as shown in FIG. 10*d*, the lower leaf 56*c* has rotated opposite the carrier stack and no longer supports the bottom carrier which now rests on the loading platform 52. At the same position, the upper leaf 56*b* supports the next carrier for repeating the cycle.

Referring again to FIGS. 9a and 9b, when the carrier drops to the loading platform 52, the contact closes switch 90, which activates motors 86 and 87. Motor 86 drives the infeed drive belt 59 until the pusher tab 58 makes contact with the carrier and pushes the carrier onto the X-Y stage drive belt 50. The stage drive belt 50 advances the carrier until contact is made with switch 91, the closing of which begins the slide scanning process described further herein.

Upon completion of the scanning process, the X-Y stage 38 moves to an unload position and motors 87 and 88 are activated to transport the carrier to the unloading platform 36 using stage drive belt 50. As noted, motor 88 drives outfeed gear 93 to engage the pitch rack 68 of the carrier 60 (FIG. 8b) until switch 92 is contacted. Closing switch 92 activates motor 89 to rotate the unloading platform 36.

Figure 11A:
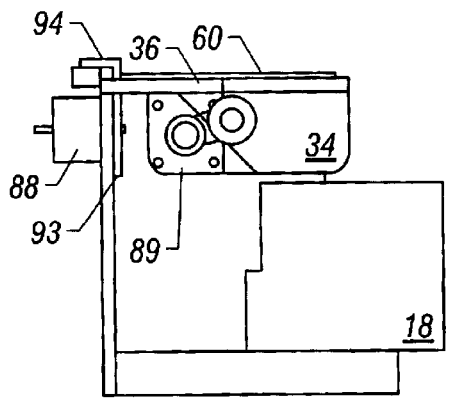
FIGS. 11a–11d illustrate the output operation of the automated slide handling subsystem.
Figure 11B:
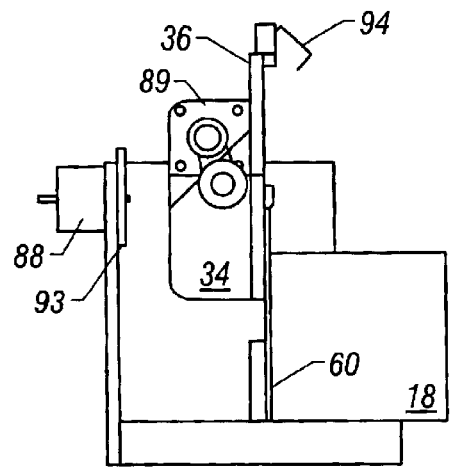
Figure 11C:
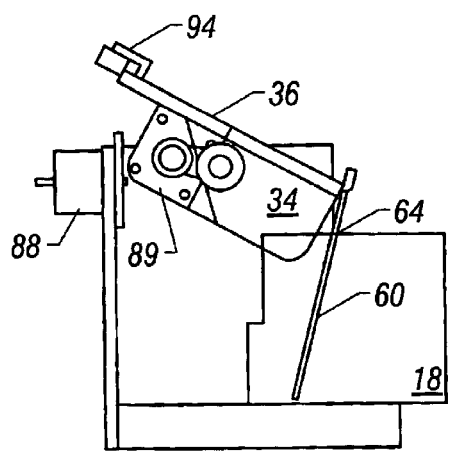
Figure 11D:
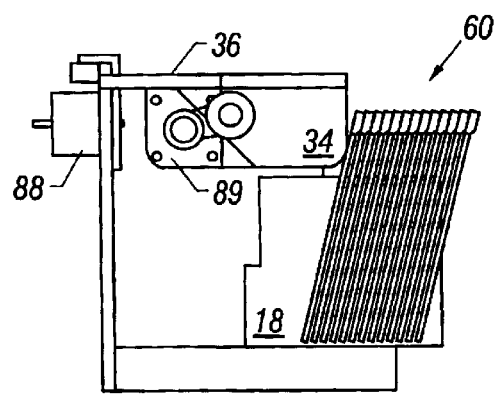

The unloading operation is shown in more detail in end views of the output module 17 (FIGS. 11a–11d). In FIG. 11a, the unloading platform 36 is shown in a horizontal position supporting a slide carrier 60. The hold-down mechanism 94 secures the carrier 60 at one end. FIG. 11b shows the output module 17 after motor 89 has rotated the unloading platform 36 to a vertical position, at which point the spring loaded hold-down mechanism 94 releases the slide carrier 60 into the output hopper 18. The carrier 60 is supported in the output hopper 18 by means of ears 64 (FIGS. 8a and 8b). FIG. 11c shows the unloading platform 36 being rotated back towards the 20 horizontal position. As the platform 36 rotates upward, it contacts the deposited carrier 60 and the upward movement pushes the carrier toward the front of the output hopper 18. FIG. 11d shows the unloading platform 36 at its original horizontal position after having output a series of slide carriers 60 to the output hopper 18.

Input and output mechanisms as described above are applicable to the autostainer 1000. For example, using a similar mechanical handling system an autostainer input and output hopper can accompany the autostainer 1000. Having described the overall system and the automated slide handling feature, the aspects of the apparatus 10 relating to scanning, focusing and image processing will now be described in further detail.

Figure 12:
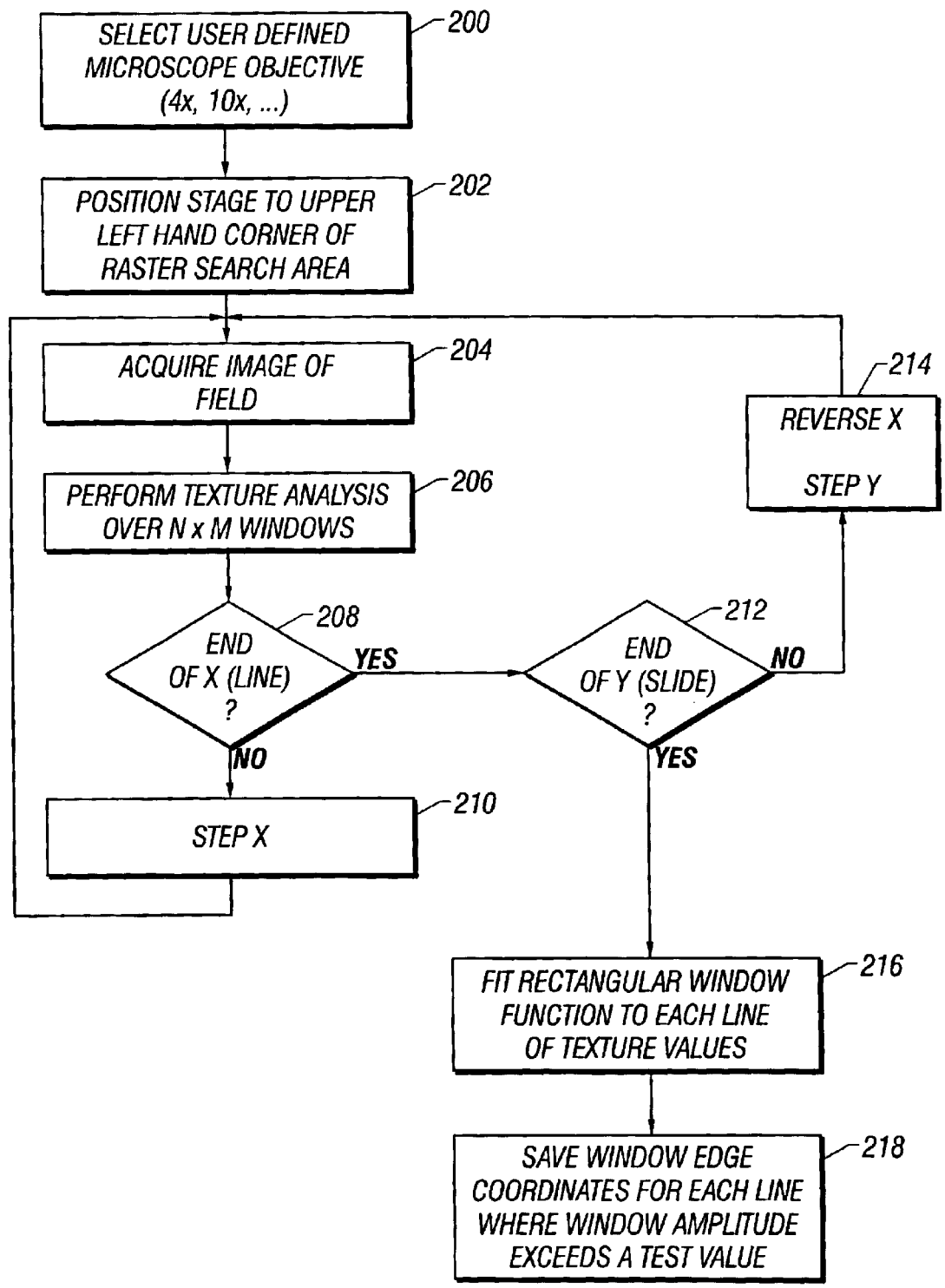
FIG. 12 is a flow diagram of the procedure for automatically determining a scan area.
Figure 14:
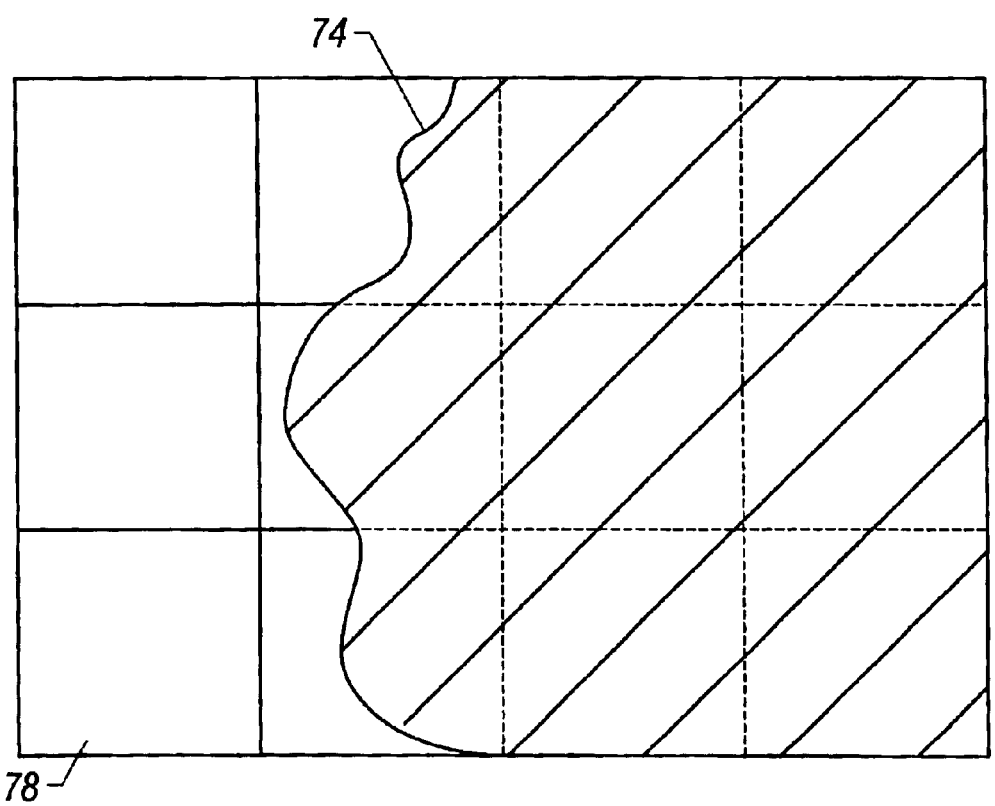
FIG. 14 illustrates an image of a field acquired in the procedure of FIG. 12.

In some cases, an operator will know ahead of time where the scan area of interest is on a slide comprising a sample. Conventional preparation of slides for examination provides repeatable and known placement of the sample on the slide. The operator can therefore instruct the system to always apply a staining reagent or instruct the system to scan the same area at the same location of every slide, which is prepared in this fashion. But there are other times in which the area of interest is not known, for example, where slides are prepared manually with a smear technique. One feature of the invention automatically determines the scan area using a texture or density analysis process. FIG. 12 is a flow diagram that describes the processing associated with the automatic location of a scan area. As shown in this flow diagram, a basic method is to pre-scan the entire slide area under incident or transmitted light to determine texture features that indicate the presence of a smear or tissue and to discriminate these areas from dirt and other artifacts. In addition, one or more distinctive features may be identified and the coordinates determined in order to make corrections to identify objects of interest in a serial subsample as described herein and using techniques known in the art.

Where an image is being acquired by the autostainer, the autostainer sets the stage comprising the slide or slide carrier to a predetermined position. The predetermined position may be located such that the camera is aimed at the middle of a slide or it may be located such that camera is aimed at the bar code on the slide. The camera then obtains an image of the slide. In one aspect of the invention, a predetermined focus length is used. In another aspect of the invention a zoom feature may be used to focus the camera and/or magnify the sample image to a desired amount. A texture analysis process can then be carried out, as described more fully below.

Where an image is acquired by an imaging apparatus, the system determines whether a user defined microscope objective has been identified 200. The system then sets the stage comprising the sample to be scanned at a predetermined position, such as the upper left hand corner of a raster search area 202. At each location of a raster scan, an image such as in FIG. 14 is acquired 204 and analyzed for texture/border information 206. Since it is desired to locate the edges of the smear or tissue sample within a given image, texture analyses are conducted over areas called windows 78 (FIG. 14), which are smaller than the entire image as shown in FIG. 14. The process iterates the scan across the slide at steps 208, 210, 212, and 214.

Figure 13:
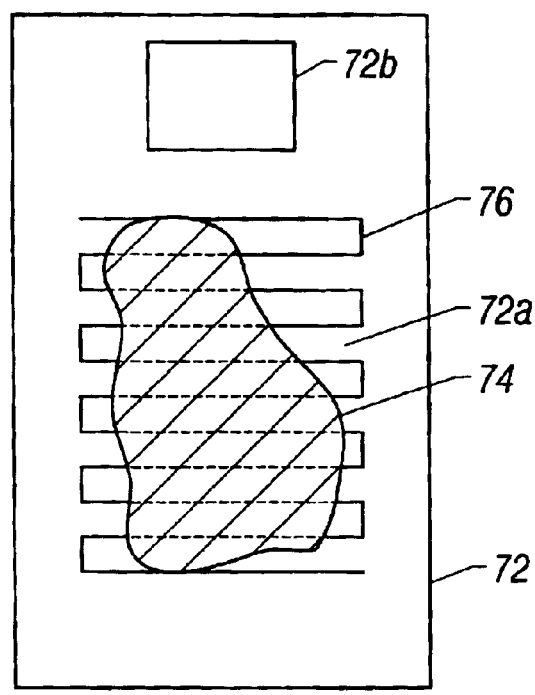
FIG. 13 shows the scan path on a prepared slide in the procedure of FIG. 12.

The texture analysis process can be performed at a low magnification, such as an image acquired by a camera without any magnification lenses, or at a 4× objective. One reason to operate at low magnification is to image the largest slide area at any one time. Since cells do not yet need to be resolved at this stage of the overall image analysis a low magnification works well. Alternatively, a higher magnification scan can be performed, which may take additional time due to the field of view being smaller and requiring additional images to be processed. On a typical slide, as shown in FIG. 13, a portion 72b of the end of the slide 72 is reserved for labeling with identification information. Excepting this label area, the entire slide is imaged by the camera on the autostainer or scanned in a raster scan fashion by the imaging apparatus to yield a number of adjacent images. Texture values include the pixel variance over the image or window, the difference between the largest and smallest pixel value within an image or window, and other indicators. The presence of a smear or tissue raises the texture values compared with a blank area.

One problem with a smear or tissue, from the standpoint of determining its location, is its non-uniform thickness and texture. For example, the smear or tissue is likely to be relatively thin at the edges and thicker towards the middle due to the nature of the smearing process. To accommodate this non-uniformity, texture analysis provides a texture value for each analyzed area. The texture value tends to gradually rise across a smear tissue from a thin area to a thick area, reaches a peak, and then falls off again to a lower value as a thin area at the edge is reached. The problem is then to decide from the series of texture values the beginning and ending, or the edges, of the smear or tissue. The texture values are fit to a square wave waveform since the texture data does not have sharp beginnings and endings.

After conducting a texture evaluation operation, one must determine which areas of elevated texture values represent the desired smear or tissue 74 (see FIG. 13), and which represent undesired artifacts. This is accomplished by fitting a step function, on a line-by-line basis, to the texture values in step 216 (see FIG. 12). This function, which resembles a single square wave beginning at one edge and ending at the other edge and having an amplitude, provides the means for discrimination. The amplitude of the best-fit step function is utilized to determine whether smear (tissue) or dirt is present since relatively high values indicate smear (tissue). If it is decided that smear (tissue) is present, the beginning and ending coordinates of this pattern are noted until all lines have been processed, and the smear (tissue) sample area defined at 218.

The first past scan above can be used to determine a particular orientation of a sample. For example, digital images are comprised of a series of pixels arranged in a matrix, a grayscale value can be attributed to each pixel to indicate the appearance of the image. "Orientation matching" between two samples (e.g., two serial sections stained with different agents) is then performed by comparing these grayscale values relative to their positions in both a first sample image (i.e., the template) and a second sample image. A match is found when the same or similar pattern is found in the second image when compared to the first image. Such systems are typically implemented in a computer for use in various manufacturing and robotic applications and are applicable to the methods and systems of the invention. For example, such systems have been utilized to automate tasks such as semiconductor wafer handling operations, fiducial recognition for pick-and-place printed circuit board (PCB) assembly, machine vision for quantification or system control to assist in location of objects on conveyor belts, pallets, and trays, and automated recognition of printed matter to be inspected, such as alignment marks. The matrix of pixels used to represent such digital images are typically arranged in a Cartesian coordinate system or other arrangement of non-rectangular pixels, such as hexagonal or diamond shaped pixels. Recognition methods usually require scanning the search image pixel by pixel in comparison with the template. Furthermore, known search techniques allow for transformations such as rotation and scaling of the template image within the second sample image, therefore requiring the recognition method to accommodate for such transformations.

Normalized grayscale correlation (NGC) has been used to match digital images reliably and accurately, as is disclosed in U.S. Pat. No. 5,602,937, entitled "Methods and Apparatus for Machine Vision High Accuracy Searching," assigned to Cognex Corporation. In addition, such software is available commercially through the Matrox Imaging Library version 7.5 (Matrox Electronic Systems Ltd., Canada).

In one aspect, a bar code or computer readable label placed at 72b (see FIG. 13) comprises instructions regarding the processing parameters (e.g., staining and imaging parameters) of a particular slide as well as additional information such as a subject's name/initials or other identification. Depending upon the type of stain to be used (e.g., precipitate stains, fluorescent stains, and the like), an image can be acquired by camera 1700 before, or before and after a stain has been dispensed on to a sample on the slide. The image(s) acquired can then be processed using the image analysis algorithms provided herein.

An imaging apparatus, depending upon the type of scan to be performed (e.g., fluorescence or transmitted light), performs a complete scan of the slide at low magnification to identify and locate candidate objects of interest, followed by further image analysis of the candidate objects of interest at high magnification in order to confirm the candidate cells or objects of interest. Where a low magnification image has been acquired by the autostainer, the imaging system can utilize this image and thus a low magnification scan is not needed. An alternate method of operation is to perform high magnification image analysis of each candidate object of interest immediately after the object has been identified at low magnification. The low magnification scanning then resumes, searching for additional candidate objects of interest.

To identify structure in tissue that cannot be captured in a single field of view image or a single staining/labeling technique, a method for histological reconstruction to analyze many fields of view on potentially many slides simultaneously is provided. The method couples composite images in an automated manner for processing and analysis. A slide on which is mounted a cellular specimen stained or unstained can be imaged and the image stored. In some instances the image will be smaller than the full area of the sample(s) on the slide. In such instances, multiple images can be aligned to generate a composite image of a full slide or multiple slides. An image of the cellular specimen is generated, digitized, and stored in memory. For example, as the viewing field of the objective lens is smaller than the entire cellular specimen, a histological reconstruction is made. The stored images of the entire tissue section or slide may then be placed together in an order such that the tissue sample is reconstructed or such that various stained samples can be matched (e.g., either side-by-side or overlapping). For example, and H/E stained slide can be matched with a fluorescently labeled slide so that analysis of the images may be performed simultaneously.

An overall detection process for a candidate cell or object of interest includes a combination of decisions made at both a low (e.g., 4× or 10×) and a high magnification (40×) level. Decision-making at the low magnification level is broader in scope, e.g., objects that loosely fit the relevant texture, color, size, and shape characteristics are identified.

Analysis at the 40× magnification level then proceeds to refine the decision-making and confirm objects as likely cells or candidate objects of interest. The higher magnification imaging process utilizes an imaging apparatus as described herein, whereas the lower magnification images can be obtained by the autostainer of the invention and/or by the imaging apparatus. For example, at the 40× level it is not uncommon to find that some objects that were identified at 10× are artifacts, which the analysis process will then reject. In addition, closely packed objects of interest appearing at 10× are separated at the 40× level. In a situation where a cell straddles or overlaps adjacent image fields, image analysis of the individual adjacent image fields could result in the cell being rejected or undetected. To avoid missing such cells, the scanning operation compensates by overlapping adjacent image fields in both the x and y directions. An overlap amount greater than half the diameter of an average cell is desirable. In one embodiment, the overlap is specified as a percentage of the image field in the x and y directions. Alternatively, a reconstruction method as described above may be used to reconstruct the image from multiple fields of view. The reconstructed image is then analyzed and processed to find objects of interest.

The time to complete an image analysis can vary depending upon the size of the scan area and the number of candidate cells or objects of interest identified. For example, in one embodiment, a complete image analysis of a scan area of two square centimeters in which 50 objects of interest are confirmed can be performed in about 12 to 15 minutes. This example includes not only focusing, scanning and image analysis but also the saving of 40× images as a mosaic on hard drive 21 (FIG. 4).

In some aspects of the invention, an initial focusing operation is performed on each slide prior to scanning. This is process may be used since slides differ, in general, in their placement in a carrier. These differences include slight variations of tilt of the slide in its carrier. Since each slide must remain in focus during scanning, the degree of tilt of each slide must be determined. This is accomplished with an initial focusing operation that determines the exact degree of tilt, so that focus can be maintained automatically during scanning. The focusing operation can be performed by the camera associated with the autostainer as well as on the imaging system.

Figure 15A:
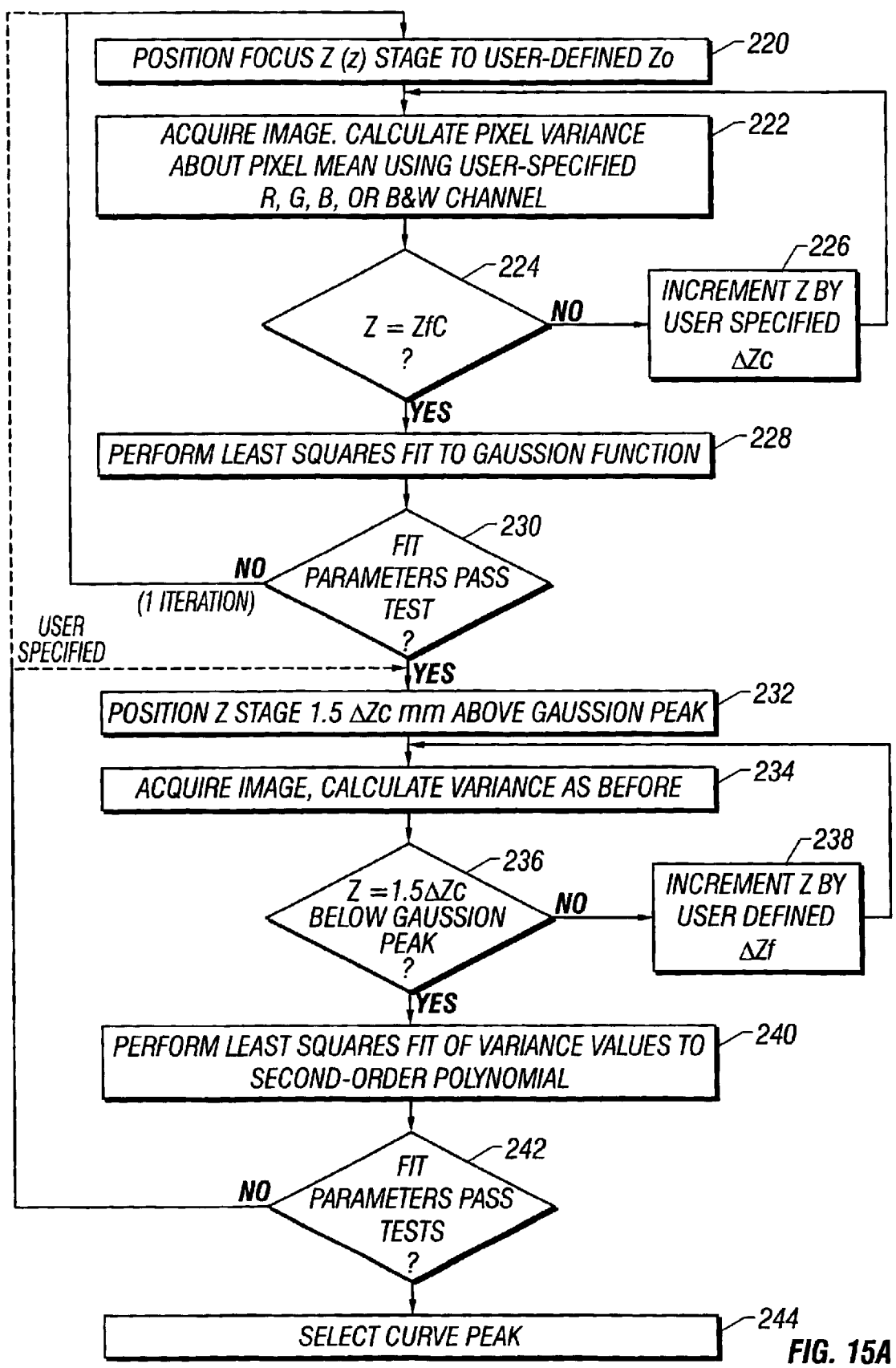
FIG. 15A is a flow diagram of a preferred procedure for determining a focal position.

The methods may vary from simple to more complex methods involving IR beam reflection and mechanical gauges. The initial focusing operation and other focusing operations to be described later utilize a focusing method based on processing of images acquired by the autostainer and the imaging apparatus. This method results in lower system cost and improved reliability since no additional parts need be included to perform focusing. FIG. 15A provides a flow diagram describing the "focus point" procedure. The basic method relies on the fact that the pixel value variance (or standard deviation) taken about the pixel value mean is maximum at best focus. A "brute-force" method could simply step through focus, using a computer controlled Z, or focus stage, calculate the pixel variance at each step, and return to the focus position providing the maximum variance. Such a method is time consuming. One method includes the determination of pixel variance at a relatively coarse number of focal positions, and then the fitting a curve to the data to provide a faster means of determining optimal focus. This basic process is applied in two steps, coarse and fine.

With reference to FIG. 15A, during the coarse step at 220–230, the Z stage is stepped over a user-specified range of focus positions, with step sizes that are also user-specified. It has been found that for coarse focusing, these data are a close fit to a Gaussian function. Therefore, this initial set of variance versus focus position data are least-squares fit to a Gaussian function at 228. The location of the peak of this Gaussian curve determines the initial or coarse estimate of focus position for input to step 232.

Following this, a second stepping operation 232–242 is performed utilizing smaller steps over a smaller focus range centered on the coarse focus position. Experience indicates that data taken over this smaller range are generally best fit by a second order polynomial. Once this least squares fit is performed at 240, the peak of the second order curve provides the fine focus position at 244.

Figure 16:
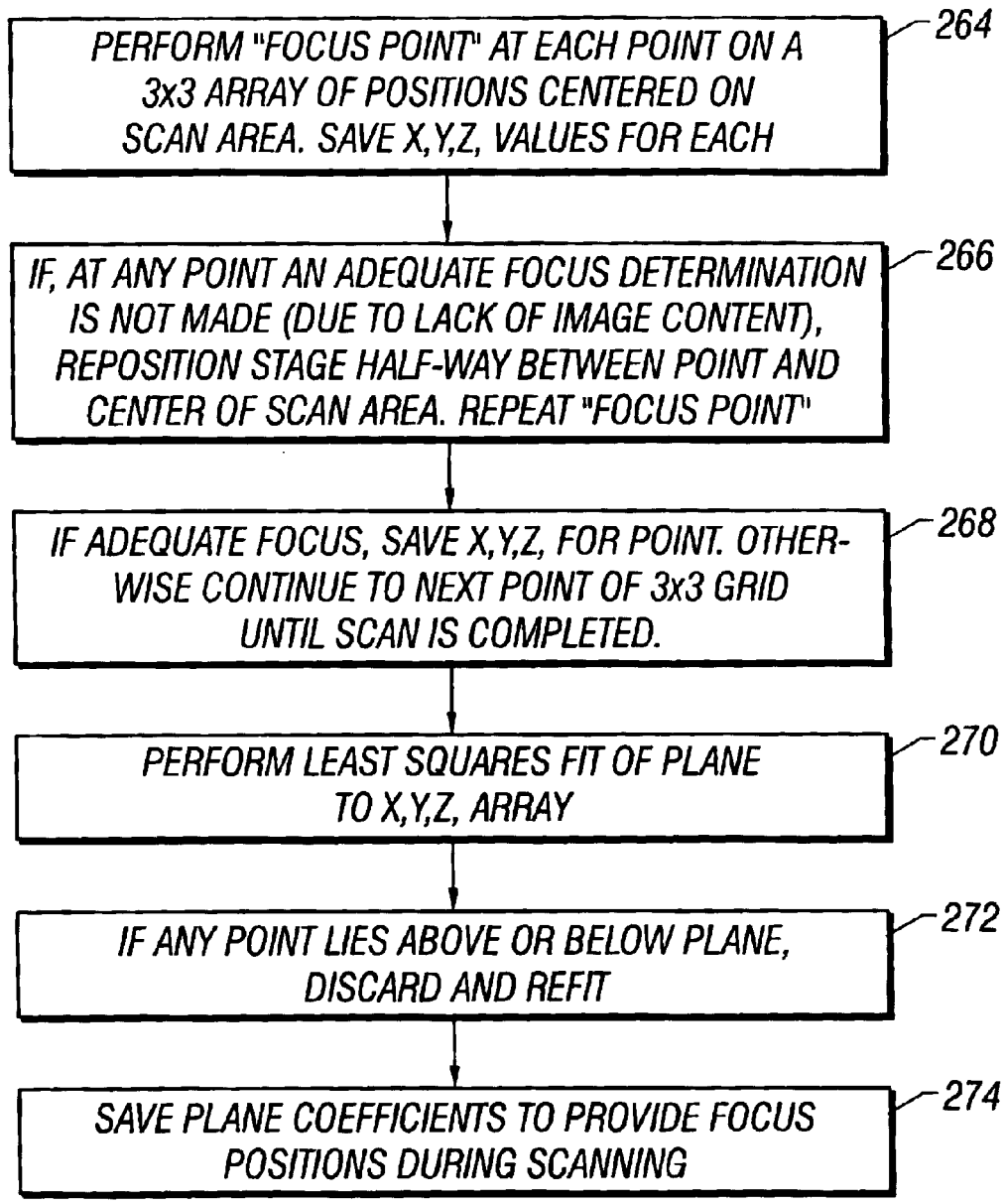
FIG. 16 is a flow diagram of a procedure for automatically determining initial focus.
Figure 17:
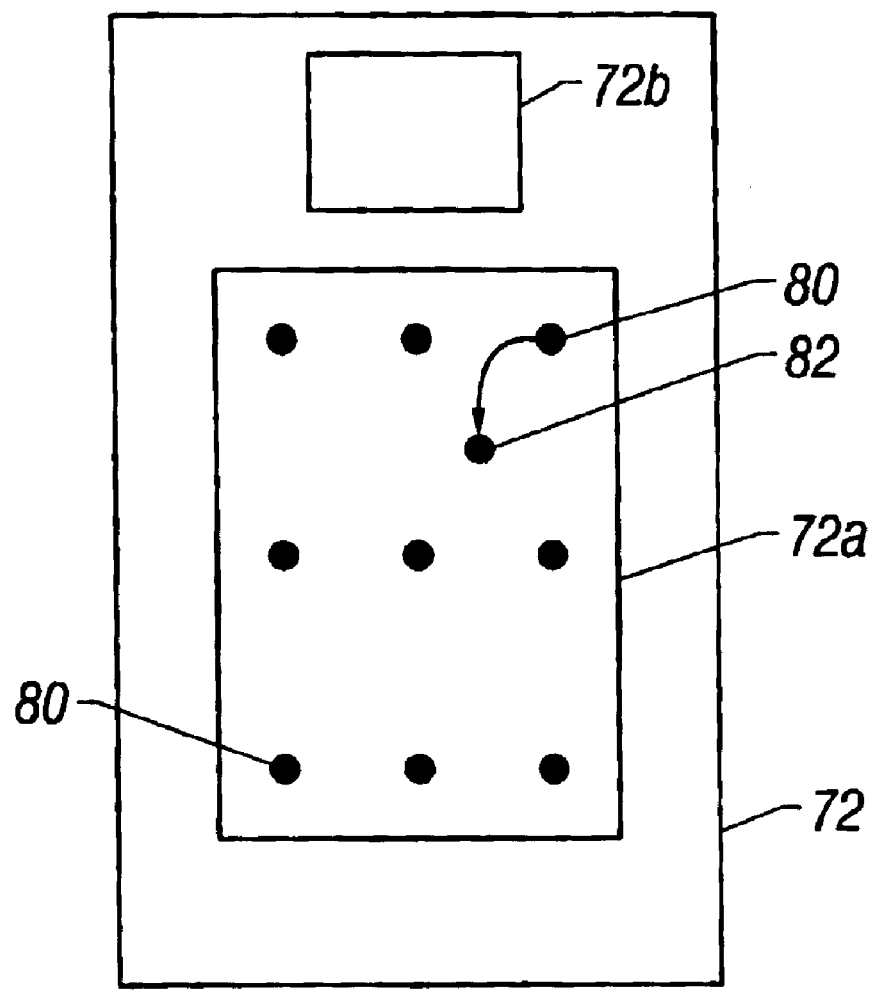
FIG. 17 shows an array of slide positions for use in the procedure of FIG. 16.

FIG. 16 illustrates a procedure for how this focusing method is utilized to determine the orientation of a slide in its carrier. As shown, focus positions are determined, as described above, for a 3×3 grid of points centered on the scan area at 264. Should one or more of these points lie outside the scan area, the method senses this at 266 by virtue of low values of pixel variance. In this case, additional points are selected closer to the center of the scan area. FIG. 17 shows the initial array of points 80 and new point 82 selected closer to the center. Once this array of focus positions is determined at 268, a least squares plane is fit to this data at 270. Focus points lying too far above or below this best-fit plane are discarded at 272 (such as can occur from a dirty cover glass over the scan area), and the data is then refit. This plane at 274 then provides the desired Z position information for maintaining focus during scanning.

Figure 18:
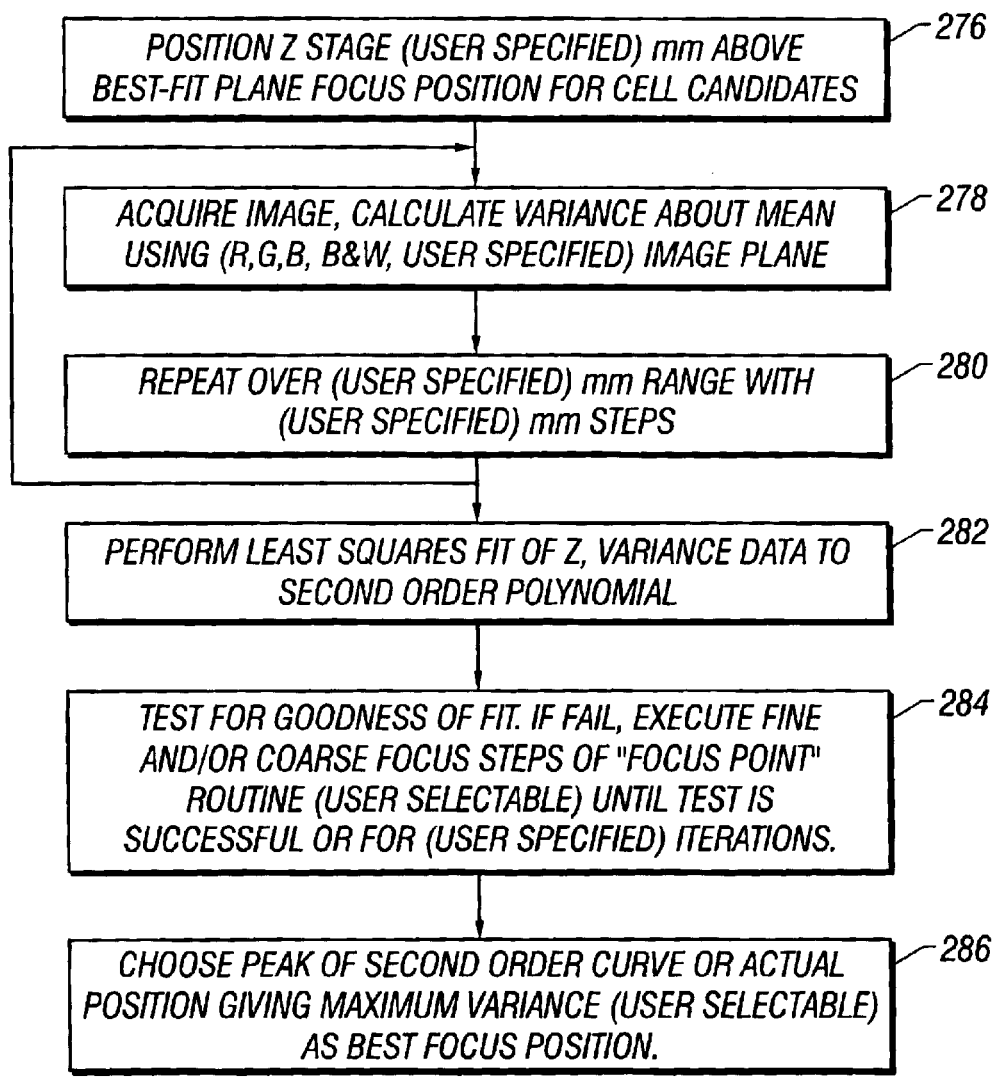
FIG. 18 is a flow diagram of a procedure for automatic focusing at a high magnification.

After determination of the best-fit focus plane, the scan area is scanned, for example, in an X raster scan over the scan area as described earlier. During scanning, the X stage is positioned to the starting point of the scan area, the focus (Z) stage is positioned to the best fit focus plane, an image is acquired and processed as described herein, and this process is repeated for all points over the scan area. In this way, focus is maintained automatically without the need for time-consuming refocusing at points during scanning. Prior to confirmation of candidate cells or objects of interest at a 40× or 60× level, a refocusing operation is conducted since the use of this higher magnification requires more precise focus than the best-fit plane provides. FIG. 18 provides the flow diagram for this process. As may be seen, this process is similar to the fine focus method described earlier in that the object is to maximize the image pixel variance. This is accomplished by stepping through a range of focus positions with the Z stage at 276 and 278, calculating the image variance at each position at 278, fitting a second order polynomial to these data at 282, and calculating the peak of this curve to yield an estimate of the best focus position at 284 and 286. This final focusing step differs from previous ones in that the focus range and focus step sizes are smaller since this magnification requires focus settings to within 0.5 micron or better. It should be noted that for some combinations of cell staining characteristics, improved focus can be obtained by numerically selecting the focus position that provides the largest variance, as opposed to selecting the peak of the polynomial. In such cases, the polynomial is used to provide an estimate of best focus, and a final step selects the actual Z position giving highest pixel variance. It should also be noted that if at any time during the focusing process at 40× or 60× the parameters indicate that the focus position is inadequate, the system automatically reverts to a coarse focusing process as described above with reference to FIG. 15A. This ensures that variations in specimen thickness can be accommodated in an expeditious manner. For some biological samples and stains, the focusing methods discussed above do not provide optimal focused results. For example, certain white blood cells known as neutrophils may be stained with Fast Red, a commonly known stain, to identify alkaline phosphatase in the cytoplasm of the cells. To further identify these cells and the material within them, the specimen may be counterstained with hematoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple. These color combinations may preclude the finding of a focused Z position using the focus processes discussed above. Where a sample has been labeled with a fluorescent agent the focus plane may be based upon the intensity of a fluorescent signal. For example, as the image scans through a Z-plane of the sample, the intensity of fluorescence will change as the focus plane passes closer to the fluorescence indicator.

Figure 15B:
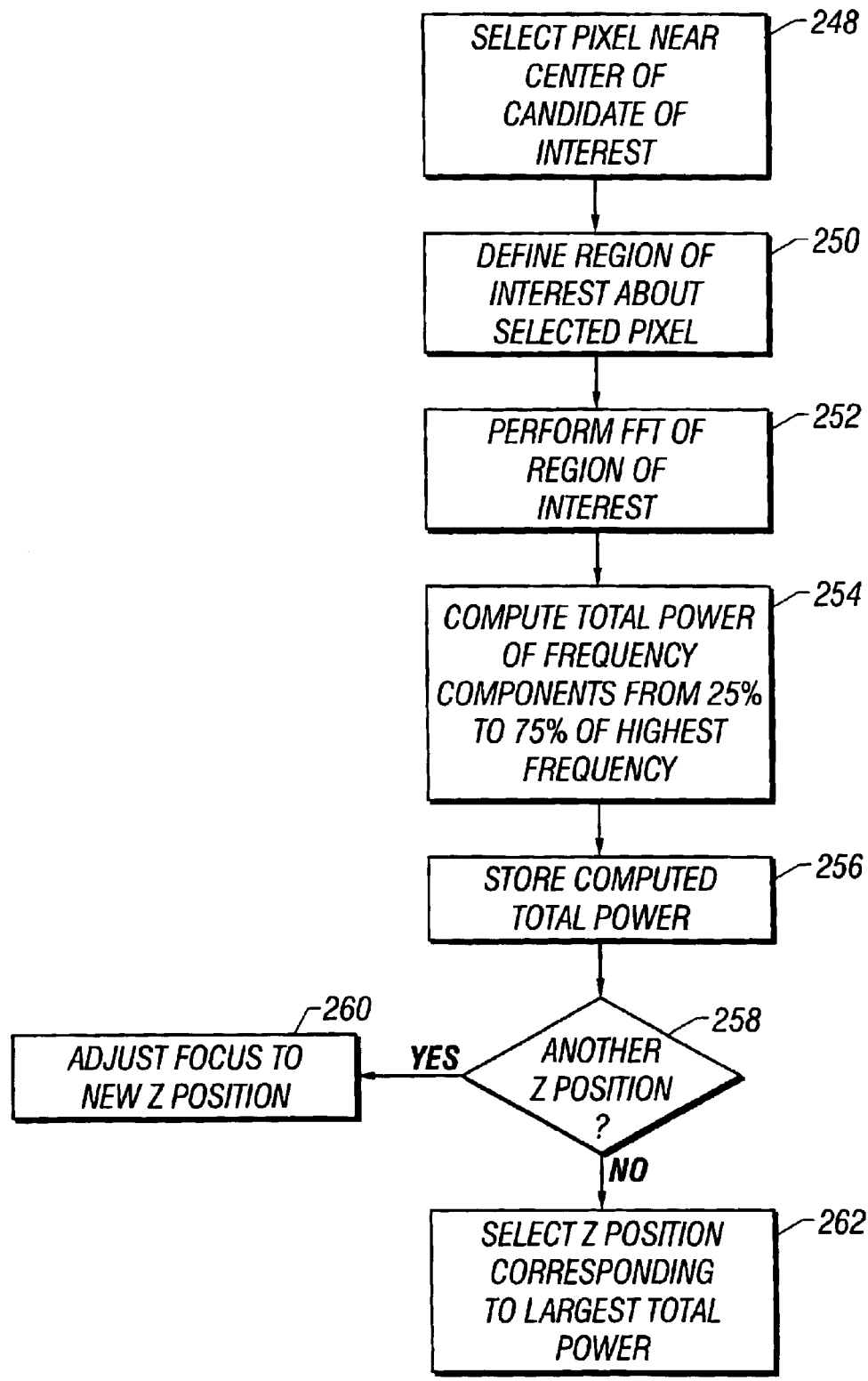
FIG. 15B is a flow diagram of a preferred procedure for determining a focal position for neutrophils stained with Fast Red and counterstained with hematoxylin.

In an effort to find a best focal position at high magnification, a focus method, such as the one shown in FIG. 15B, may be used. That method begins by selecting a pixel near the center of a candidate object of interest 248 and defining a region of interest centered about the selected pixel 250. Typically, the width of the region of interest is a number of columns, which is a power of 2. This width determination arises from subsequent processing of the region of interest using a one dimensional Fast Fourier Transform (FFT) technique. As is known in the art, processing columns of pixel values using the FFT technique is facilitated by making the number of columns to be processed a power of two. While the height of the region of interest is also a power of two, it need not be unless a two dimensional FFT technique is used to process the region of interest.

After the region of interest is selected, the columns of pixel values are processed using a one dimensional FFT to determine a spectra of frequency components for the region of interest 252. The frequency spectra ranges from DC to some highest frequency component. For each frequency component, a complex magnitude is computed. The complex magnitudes for the frequency components, which range from approximately 25% of the highest component to approximately 75% of the highest component, are squared and summed to determine the total power for the region of interest 254. Alternatively, the region of interest may be processed with a smoothing window, such as a Hanning window, to reduce the spurious high frequency components generated by the FFT processing of the pixel values in the region of interest. Such preprocessing of the region of interest permits complex magnitudes over the complete frequency range to be squared and summed. After the power for a region has been computed and stored 256, a new focal position is selected, focus adjusted 258 and 260, and the process repeated. After each focal position has been evaluated, the one having the greatest power factor is selected as the one best in focus 262.

The following describes the image processing methods which are utilized to decide whether a candidate object of interest such as, for example, a stained tumor cell is present in a given image, or field, during the scanning process. Candidate objects of interest, which are detected during scanning, are reimaged at higher (40× or 60×) magnification, the decision confirmed, and an image of the object of interest as well as its coordinates saved for later review. In one aspect of the invention, objects of interest are first acquired and identified under transmitted and/or incident light. The image processing includes color space conversion, low pass filtering, background suppression, artifact suppression, morphological processing, and blob analysis. One or more of these steps can optionally be eliminated. The operator may optionally configure the system to perform any or all of these steps and whether to perform certain steps more than once or several times in a row. It should also be noted that the sequence of steps may be varied and thereby optimized for specific reagents or reagent combinations; however, a typical sequence is described herein.

Figure 19A:
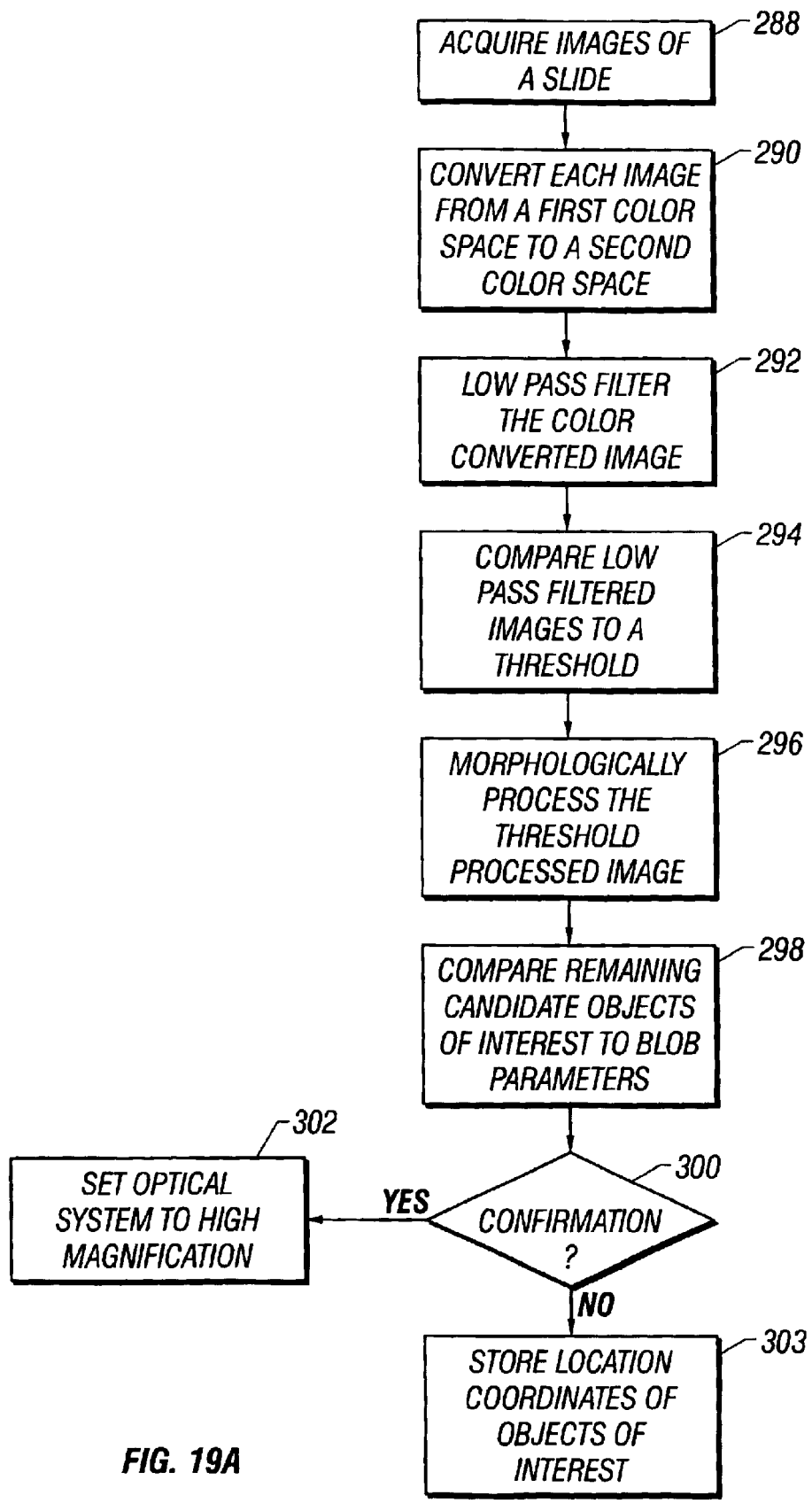
FIG. 19A is a flow diagram of an overview of the preferred process to locate and identify objects of interest in a stained biological sample on a slide.

An overview of the identification process is shown in FIG. 19A. The process for identifying and locating candidate objects of interest in a stained biological sample under transmitted light on a slide begins with an acquisition of images obtained by scanning the slide at low magnification 288. The low magnification image includes images acquired by an autostainer of the invention. Each image is then converted from a first color space to a second color space 290 and the color converted image is low pass filtered 292. The pixels of the low pass filtered image are then compared to a threshold 294 and those pixels having a value equal to or greater than the threshold are identified as candidate object of interest pixels and those less than the threshold are determined to be artifact or background pixels. The candidate object of interest pixels are then morphologically processed to identify groups of candidate object of interest pixels as candidate objects of interest 296. These candidate objects of interest are then compared to blob analysis parameters 298 to further differentiate candidate objects of interest from objects, which do not conform to the blob analysis parameters and do not warrant further processing. The location of the candidate objects of interest may be stored prior to confirmation at high magnification. The process continues by determining whether the candidate objects of interest have been confirmed 300. If they have not been confirmed, the optical system is set to high magnification 302 and images of the slide at the locations corresponding to the candidate objects of interest identified in the low magnification images are acquired 288 under higher magnification. These images are then color converted 290, low pass filtered 292, compared to a threshold 294, morphologically processed 296, and compared to blob analysis parameters 298 to confirm which candidate objects of interest located from the low magnification images are objects of interest. The coordinates of the objects of interest are then stored for future reference.

In general, the candidate objects of interest, such as tumor cells, are detected based on a combination of characteristics, including size, shape, and color. The chain of decision making based on these characteristics begins with a color space conversion process. The optical sensing array coupled to the autostainer and/or microscope subsystem outputs a color image comprising a matrix of pixels. Each pixel comprises red, green, and blue (RGB) signal values.

It is desirable to transform the matrix of RGB values to a different color space because the difference between candidate objects of interest and their background, such as tumor and normal cells, may be determined from their respective colors. Samples are generally stained with one or more standard stains (e.g., DAB, New Fuchsin, AEC), which are "reddish" in color. Candidate objects of interest retain more of the stain and thus appear red while normal cells remain unstained. The specimens may also be counterstained with hematoxylin so the nuclei of normal cells or cells not containing an object of interest appear blue. In addition to these objects, dirt and debris can appear as black, gray, or can also be lightly stained red or blue depending on the staining procedures utilized. The residual plasma or other fluids also present on a smear (tissue) may also possess some color.

In one aspect of a color conversion operation, a ratio of two of the RGB signal values is formed to provide a means for discriminating color information. With three signal values for each pixel, nine different ratios can be formed: R/R, R/G, R/B, G/G, G/B, G/R, B/B, B/G, B/R. The optimal ratio to select depends upon the range of color information expected in the slide sample. As noted above, typical stains used in light microscopy for detecting candidate objects of interest such as tumor cells are predominantly red, as opposed to predominantly green or blue. Thus, the pixels of an object of interest that has been stained would contain a red component, which is larger than either the green or blue components. A ratio of red divided by blue (R/B) provides a value which is greater than one for, e.g. tumor cells, but is approximately one for any clear or white areas on the slide. Since other components of the sample, for example, normal cells, typically are stained blue, the R/B ratio for pixels of these other components (e.g., normal cells) yields values of less than one. The R/B ratio is used for separating the color information typical in these applications.

Figure 19B:
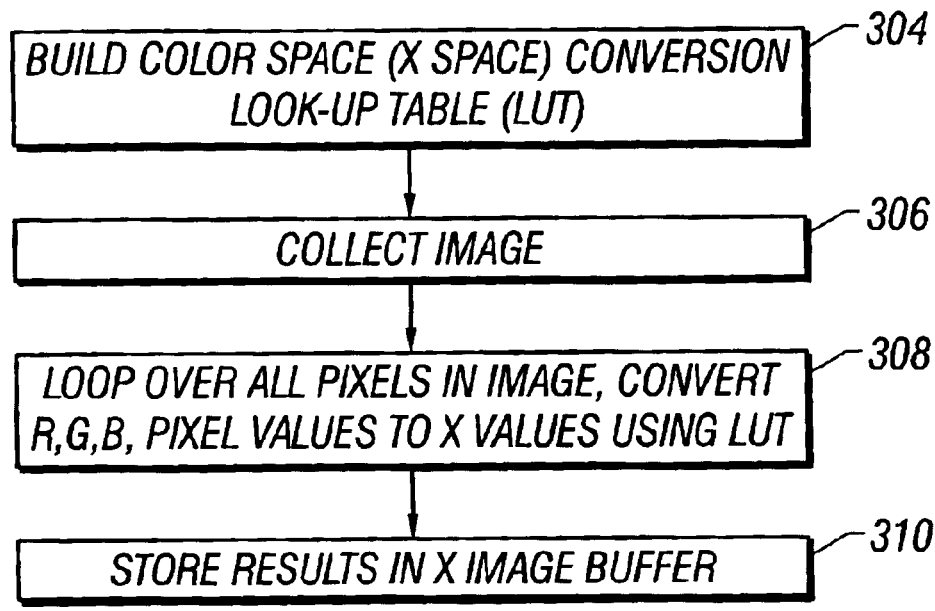
FIG. 19B is a flow diagram of a procedure for color space conversion.

FIG. 19B illustrates the flow diagram by which this conversion is performed. In the interest of processing speed, a conversion can be implemented with a look up table. The use of a look up table for color conversion accomplishes three functions: 1) performing a division operation; 2) scaling the result for processing as an image having pixel values ranging from 0 to 255; and 3) defining objects which have low pixel values in each color band (R,G,B) as "black" to avoid infinite ratios (e.g., dividing by zero). These "black" objects are typically staining artifacts or can be edges of bubbles caused by pasting a coverglass over the specimen. Once the look up table is built at 304 for the specific color ratio (e.g., choices of tumor and nucleated cell stains), each pixel in the original RGB image is converted at 308 to produce the output. Since it is of interest to separate the red stained tumor cells from blue stained normal ones, the ratio of color values is then scaled by a user specified factor. As an example, for a factor of 128 and the ratio of (red pixel value)/(blue pixel value), clear areas on the slide would have a ratio of 1 scaled by 128 for a final X value of 128. Pixels that lie in red stained tumor cells would have X value greater than 128, while blue stained nuclei of normal cells would have value less than 128. In this way, the desired objects of interest can be numerically discriminated. The resulting pixel matrix, referred to as the X-image, is a gray scale image having values ranging from 0 to 255.

Other methods exist for discriminating color information. Another method of image analysis includes converting the RGB color information into another color space, such as HSI (hue, saturation, intensity) space. In such a space, distinctly different hues such as red, blue, green, yellow, may be readily separated. In addition, relatively lightly stained objects may be distinguished from more intensely stained ones by virtue of differing saturations. Methods of converting from RGB space to HSI space are described in U.S. Pat. No. 6,404,916, the entire contents of which are incorporated by reference. In brief, color signal inputs are received by a converter that converts the representation of a pixel's color from red, green, and blue (RGB) signals to hue, saturation, and intensity signals (HSI). The conversion of RGB signals to HSI signals is equivalent to a transformation from the rectilinear RGB coordinate system used in color space to a cylindrical coordinate system in which hue is the polar coordinate, saturation is the radial coordinate, and intensity is the axial coordinate, whose axis lies on a line between black and white in coordinate space. A number of algorithms to perform this conversion are known, and computer chips are available to perform the algorithms.

Exemplary methods include a process whereby a signal representative of a pixel color value is converted to a plurality of signals, each signal representative of a component color value including a hue value, a saturation value, and an intensity value. For each component color value, an associated range of values is set. The ranges together define a non-rectangular subvolume in HSI color space. A determination is made whether each of the component values falls within the associated range of values. The signal is then outputting, indicating whether the pixel color value falls within the color range in response to each of the component values falling within the associated range of values. The range of values associated with the hue value comprises a range of values between a high hue value and a low hue value, the range of values associated with the saturation value comprises a range of values above a low saturation value, and the range of values associated with the intensity value comprises a range of values between a high intensity value and a low intensity value.

Such methods can be executed on an apparatus that may include a converter to convert a signal representative of a pixel color value to a plurality of signals representative of component color values including a hue value, a saturation value, and an intensity value. The hue comparator determines if the hue value falls within a first range of values. The apparatus may further include a saturation comparator to determine if the saturation value falls within a second range of values, as well as an intensity comparator to determine if the intensity value falls within a third range of values. In addition, a color identifier connected to each of the hue comparator, the saturation comparator, and the intensity comparator, is adapted to output a signal representative of a selected color range in response to the hue value falling within the first range of values, the saturation value falling within the second range of values, and the intensity value falling within the third range of values. The first range of values, the second range of values, and the third range of values define a non-rectangular subvolume in HSI color space, wherein the first range of values comprises a plurality of values between a low hue reference value and a high hue reference value, the second range of values comprises a plurality of values above a low saturation value, and the third range of values comprises a plurality of values between a low intensity value and a high intensity value.

In yet another approach, one could obtain color information by taking a single color channel from the optical sensing array. As an example, consider a blue channel, in which objects that are red are relatively dark. Objects that are blue, or white, are relatively light in the blue channel. In principle, one could take a single color channel, and simply set a threshold wherein everything darker than some threshold is categorized as a candidate object of interest, for example, a tumor cell, because it is red and hence dark in the channel being reviewed. However, one problem with the single channel approach occurs where illumination is not uniform. Non-uniformity of illumination results in non-uniformity across the pixel values in any color channel, for example, tending to peak in the middle of the image and dropping off at the edges where the illumination falls off. Performing thresholding on this non-uniform color information runs into problems, as the edges sometimes fall below the threshold, and therefore it becomes more difficult to pick the appropriate threshold level. However, with the ratio technique, if the values of the red channel fall off from center to edge, then the values of the blue channel also fall off center to edge, resulting in a uniform ratio at non-uniform lighting. Thus, the ratio technique is more immune to illumination.

As described, the color conversion scheme is relatively insensitive to changes in color balance, e.g., the relative outputs of the red, green, and blue channels. However, some control is necessary to avoid camera saturation, or inadequate exposures in any one of the color bands. This color balancing is performed automatically by utilizing a calibration slide consisting of a clear area, and a "dark" area having a known optical transmission or density. The system obtains images from the clear and "dark" areas, calculates "white" and "black" adjustments for the image-frame grabber or image processor 25, and thereby provides correct color balance.

In addition to the color balance control, certain mechanical alignments are automated in this process. The center point in the field of view as measured on the slide can vary by several (or several tens of) microns. This is the result of slight variations in position of the camera 1700 associated with the autostainer or the microscope objectives 44a as determined by the turret 44 (FIG. 4 and 6), small variations in alignment of the objectives with respect to the system optical axis, and other factors. Since it is desired that the camera and each microscope objective be centered at the same point, these mechanical offsets must be measured and automatically compensated.

This is accomplished by imaging a test slide that contains a recognizable feature or mark. An image of this pattern is obtained by the system with a given objective, and the position of the mark determined. The system then rotates the turret to the next lens objective, obtains an image of the test object, and its position is redetermined. Apparent changes in position of the test mark are recorded for the objective. This process is continued for all objectives. Once these spatial offsets have been determined, they are automatically compensated for by moving the camera 1700 or the XY stage 38 (depending upon the device, e.g., the autostainer or imaging apparatus) by an equal (but opposite) amount of offset. In this way, as different lens objectives are selected, there is no apparent shift in center point or area viewed. A low pass filtering process precedes thresholding. An objective of thresholding is to obtain a pixel image matrix having only candidate cells or objects of interest, such as tumor cells above a threshold level and everything else below it. However, an actual acquired image will contain noise. The noise can take several forms, including white noise and artifacts. The microscope slide can have small fragments of debris that pick up color in the staining process and these are known as artifacts. These artifacts are generally small and scattered areas, on the order of a few pixels, which are above the threshold. The purpose of low pass filtering is to essentially blur or smear the entire color converted image. The low pass filtering process will smear artifacts more than larger objects of interest, such as tumor cells and thereby eliminate or reduce the number of artifacts that pass the thresholding process. The result is a cleaner thresholded image downstream. In the low pass filter process, a 3×3 matrix of coefficients is applied to each pixel in the X-image. A typical coefficient matrix is as follows:

1/9 1/9 1/9
1/9 1/9 1/9
1/9 1/9 1/9

At each pixel location, a 3×3 matrix comprising the pixel of interest and its neighbors is multiplied by the coefficient matrix and summed to yield a single value for the pixel of interest. The output of this spatial convolution process is again a pixel matrix. As an example, consider a case where the center pixel and only the center pixel, has a value of 255 and each of its other neighbors, top left, top, top right and so forth, have values of 0.

This singular white pixel case corresponds to a small object. The result of the matrix multiplication and addition using the coefficient matrix is a value of (1/9)*255 or 28.3 for the center pixel, a value which is below the nominal threshold of 128. Now consider another case in which all the pixels have a value of 255 corresponding to a large object. Performing the low pass filtering operation on a 3×3 matrix for this case yields a value of 255 for the center pixel. Thus, large objects retain their values while small objects are reduced in amplitude or eliminated. In the preferred method of operation, the low pass filtering process is performed on the X image twice in succession.

Figure 20:
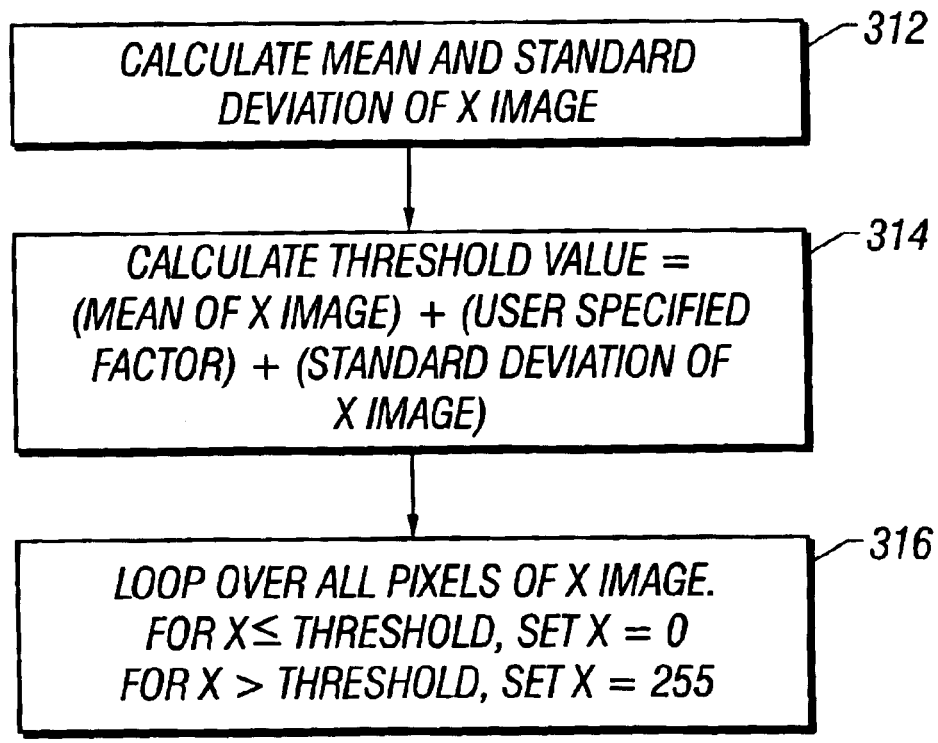
FIG. 20 is a flow diagram of a procedure for background suppression via dynamic thresholding.

In order to separate objects of interest such as, for example, a tumor cell in the image from other objects and background, a thresholding operation is performed designed to set pixels within candidate cells or objects of interest to a value of 255, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, a dynamic thresholding process is used whereby the threshold is adjusted dynamically for each acquired image. Thus, for each image, a single threshold value is derived specific to that image. As shown in FIG. 20, the basic method is to calculate, for each field, the mean X value, and the standard deviation about this mean 312. The threshold is then set at 314 to the mean plus an amount defined by the product of a factor (e.g., a user specified factor) and the standard deviation of the color converted pixel values. The standard deviation correlates to the structure and number of objects in the image. Typically, a user specified factor is in the range of approximately 1.5 to 2.5. The factor is selected to be in the lower end of the range for slides in which the stain has primarily remained within cell boundaries and the factor is selected to be in the upper end of the range for slides in which the stain is pervasively present throughout the slide. In this way, as areas are encountered on the slide with greater or lower background intensities, the threshold may be raised or lowered to help reduce background objects. With this method, the threshold changes in step with the aging of the light source such that the effects of the aging are canceled out. The image matrix resulting at 316 from the thresholding step is a binary image of black (0) and white (255) pixels. As is often the case with thresholding operations such as that described above, some undesired areas will lie above the threshold value due to noise, small stained cell fragments, and other artifacts. It is desired and possible to eliminate these artifacts by virtue of their small size compared with legitimate cells of interest. In one aspect, morphological processes are utilized to perform this function.

Morphological processing is similar to the low pass filter convolution process described earlier except that it is applied to a binary image. Similar to spatial convolution, the morphological process traverses an input image matrix, pixel by pixel, and places the processed pixels in an output matrix. Rather than calculating a weighted sum of the neighboring pixels as in the low pass convolution process, the morphological process uses set theory operations to combine neighboring pixels in a nonlinear fashion.

Erosion is a process whereby a single pixel layer is taken away from the edge of an object. Dilation is the opposite process, which adds a single pixel layer to the edges of an object. The power of morphological processing is that it provides for further discrimination to eliminate small objects that have survived the thresholding process and yet are not likely objects of interest (e.g., tumor cells). The erosion and dilation processes that make up a morphological "open" operation make small objects disappear yet allow large objects to remain. Morphological processing of binary images is described in detail in "Digital Image Processing", pages 127–137, G. A. Baxes, John Wiley & Sons, (1994).

Figure 21:
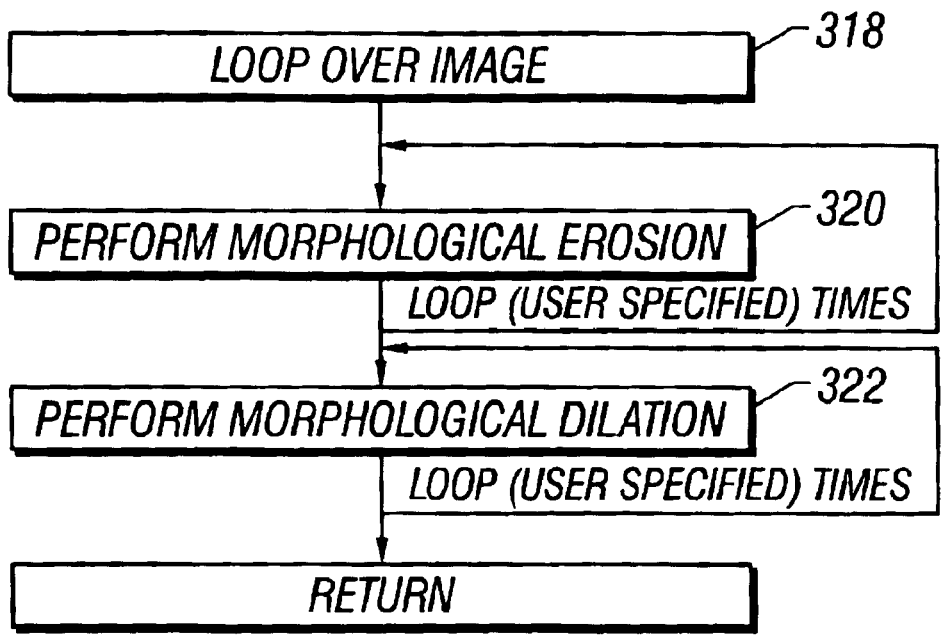
FIG. 21 is a flow diagram of a procedure for morphological processing.

FIG. 21 illustrates the flow diagram for this process. A single morphological open consists of a single morphological erosion 320 followed by a single morphological dilation 322. Multiple "opens" consist of multiple erosions followed by multiple dilations. In one embodiment, one or two morphological opens are found to be suitable. At this point in the processing chain, the processed image contains thresholded objects of interest, such as, for example, tumor cells (if any were present in the original image), and possibly some residual artifacts that were too large to be eliminated by the processes above.

Figure 22:
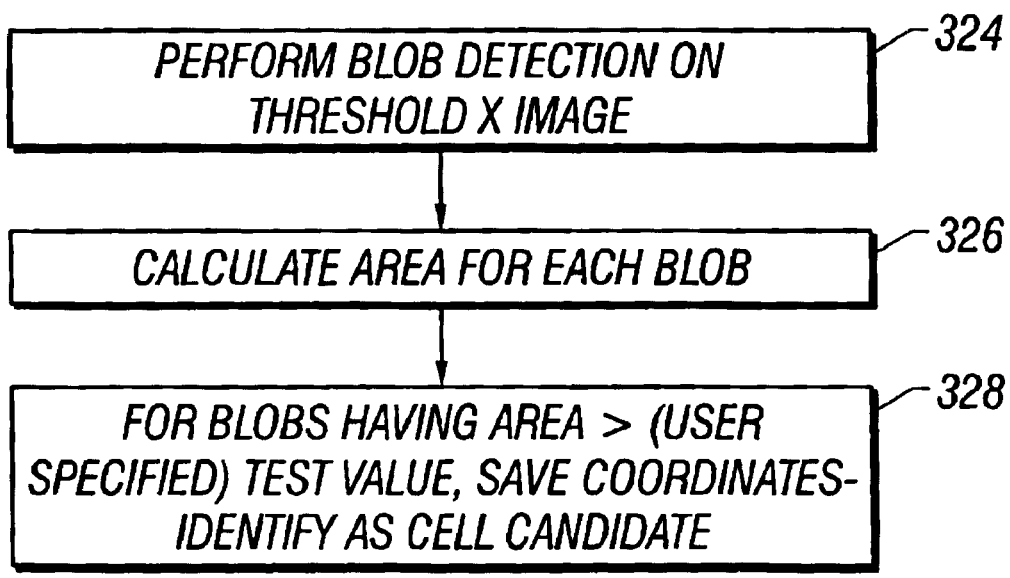
FIG. 22 is a flow diagram of a procedure for blob analysis.

FIG. 22 provides a flow diagram illustrating a blob analysis performed to determine the number, size, and location of objects in the thresholded image. A blob is defined as a region of connected pixels having the same "color", in this case, a value of 255. Processing is performed over the entire image to determine the number of such regions at 324 and to determine the area and coordinates for each detected blob at 326. Comparison of the size of each blob to a known minimum area at 328 for a tumor cell allows a refinement in decisions about which objects are objects of interest, such as tumor cells, and which are artifacts. The location of candidate cells or objects of interest identified in this process are saved for a higher magnification reimaging step described herein. Objects not passing the size test are disregarded as artifacts.

Figure 23:
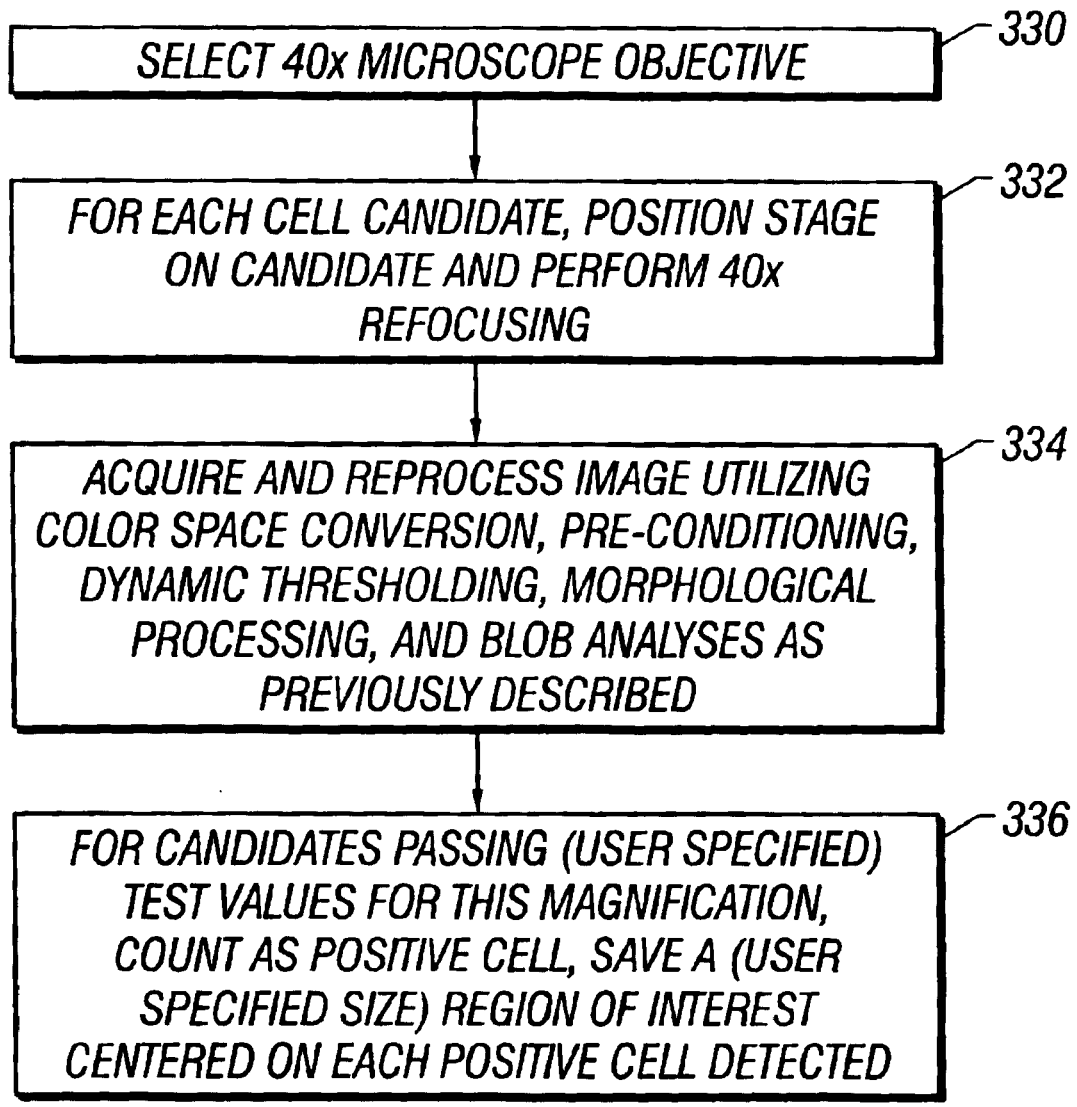
FIG. 23 is a flow diagram of a procedure for image processing at a high magnification.

The processing chain described herein identifies candidate cells or objects of interest at a scanning magnification. As illustrated in FIG. 23, at the completion of scanning, the system switches to a higher magnification objective (e.g., 40×) at 330, and each candidate cell or object of interest is reimaged to confirm the identification 332. Each 40× image is reprocessed at 334 using the same steps as described above but with test parameters suitably modified for the higher magnification. At 336, a region of interest centered on each confirmed cell is saved to the hard drive for review by the pathologist.

Similarly, once imaging has been performed in transmitted light imaging in fluorescent light may be performed using a process described above. The autostainer can obtain a first image under incident or transmitted light to determine a region in which to dispense a reagent (e.g., a fluorescently labeled agent or stain). The autostainer can then obtain a second image under fluorescent excitation light in order to obtain a fluorescent low-magnification image. Similarly, the imaging apparatus can obtain images under different light sources. For example, as illustrated in FIG. 23, at the completion of scanning and imaging at a higher magnification under transmitted light, the system switches from transmitted light to fluorescent excitation light and obtains images at a desired magnification objective (e.g., 40×) at 330, and each candidate cell or object of interest identified under transmitted light is reimaged under fluorescent light 332. Each fluorescent image is then processed at 334 but with test parameters suitably modified for the fluorescent imaging. At 336, fluorescent image comprising a fluorescently labeled object of interest is saved to storage device for review by a pathologist.

Figure 24:
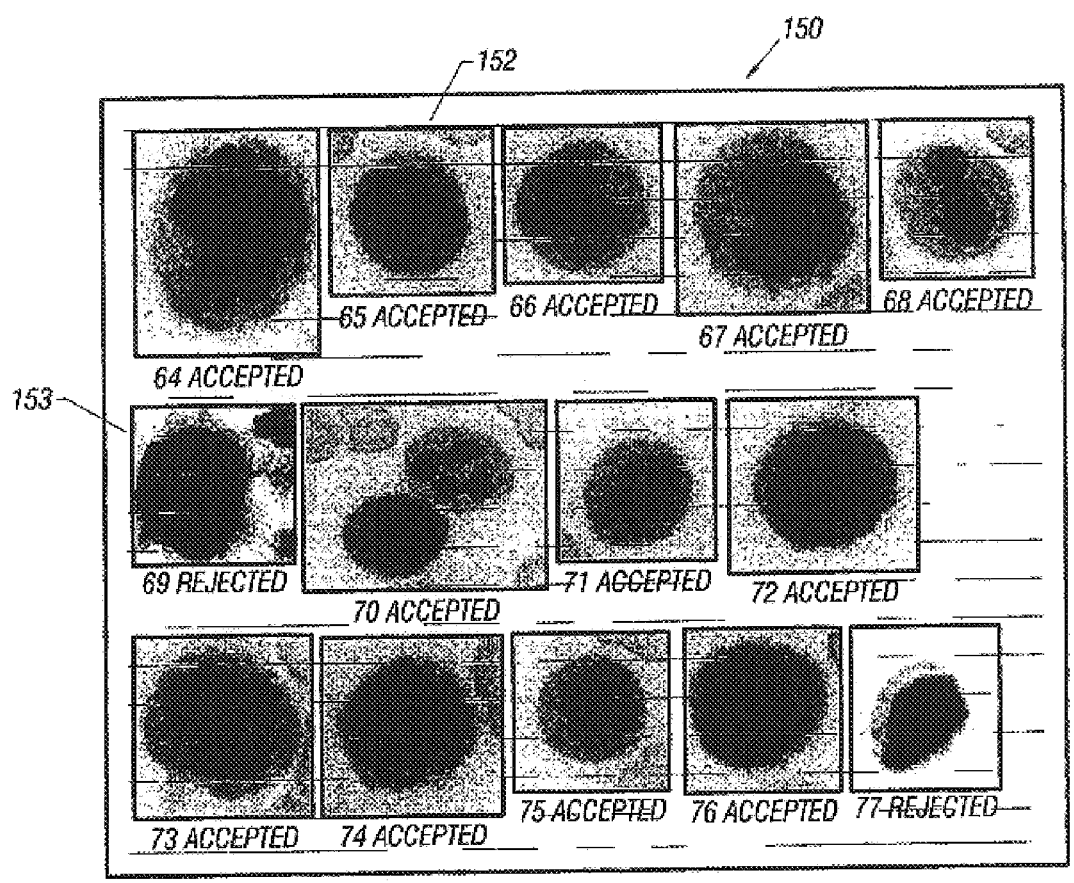
FIG. 24 illustrates a mosaic of cell images produced by the apparatus.

As noted earlier, a mosaic of saved images is made available for review by a pathologist. As shown in FIG. 24, a series of images of cells that have been confirmed by the image analysis is presented in the mosaic 150. The pathologist can then visually inspect the images to make a determination whether to accept 152 or reject 153 each cell image. Such a determination can be noted and saved with the mosaic of images for generating a printed report.

In addition to saving an image of a candidate cell or object of interest, the coordinates are saved should the pathologist wish to directly view the cell through the oculars or on the image monitor. In this case, the pathologist reloads the slide carrier, selects the slide and cell for review from a mosaic of cell images, and the system automatically positions the cell under the microscope for viewing.

Figure 25:
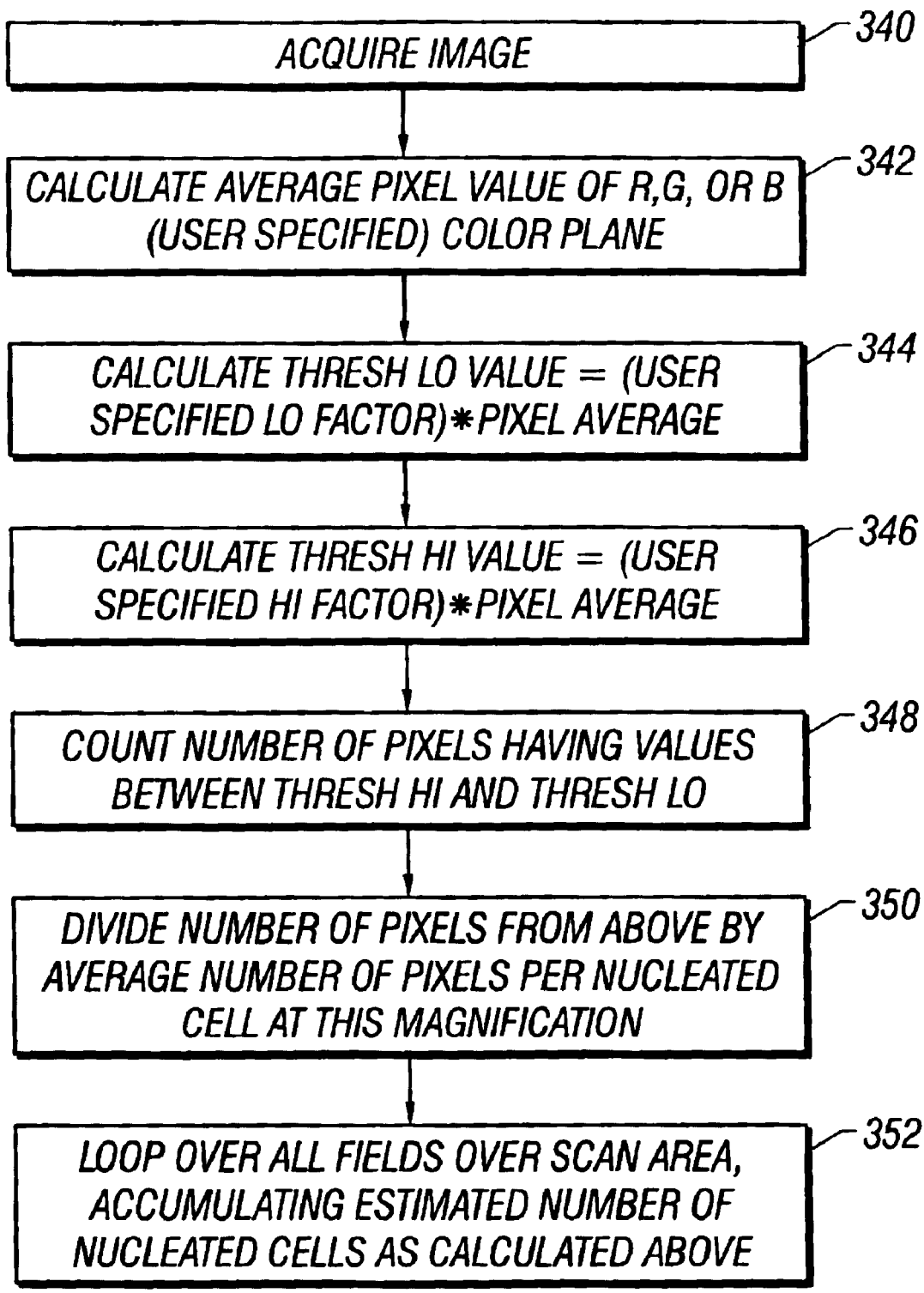
FIG. 25 is a flow diagram of a procedure for estimating the number of nucleated cells in a field.

It has been found that normal cells whose nuclei have been stained with hematoxylin are often quite numerous, numbering in the thousands per 10× image. Since these cells are so numerous, and since they tend to clump, counting each individual nucleated cell would add an excessive processing burden, at the expense of speed, and would not necessarily provide an accurate count due to clumping. The apparatus performs an estimation process in which the total area of each field that is stained hematoxylin blue is measured and this area is divided by the average size of a nucleated cell. FIG. 25 outlines this process. In this process, an image is acquired 340, and a single color band (e.g., the red channel provides the best contrast for blue stained nucleated cells) is processed by calculating the average pixel value for each field at 342, thereby establishing two threshold values (high and low) as indicated at 344, 346, and counting the number of pixels between these two values at 348. In the absence of dirt, or other opaque debris, this provides a count of the number of predominantly blue pixels. By dividing this value by the average area for a nucleated cell at 350, and looping over all fields at 352, an approximate cell count is obtained. This process yields an accuracy of +/−15%. It should be noted that for some slide preparation techniques, the size of nucleated cells can be significantly larger than the typical size. The operator can select the appropriate nucleated cell size to compensate for these characteristics.

As with any imaging system, there is some loss of modulation transfer (e.g., contrast) due to the modulation transfer function (MTF) characteristics of the imaging optics, camera, electronics, and other components. Since it is desired to save "high quality" images of cells of interest both for pathologist review and for archival purposes, it is desired to compensate for these MTF losses. An MTF compensation (MTFC) is performed as a digital process applied to the acquired digital images. A digital filter is utilized to restore the high spatial frequency content of the images upon storage, while maintaining low noise levels. With this MTFC technology, image quality is enhanced, or restored, through the use of digital processing methods as opposed to conventional oil-immersion or other hardware based methods. MTFC is described further in "The Image Processing Handbook," pages 225 and 337, J. C. Rues, CRC Press (1995).

Figure 26A:
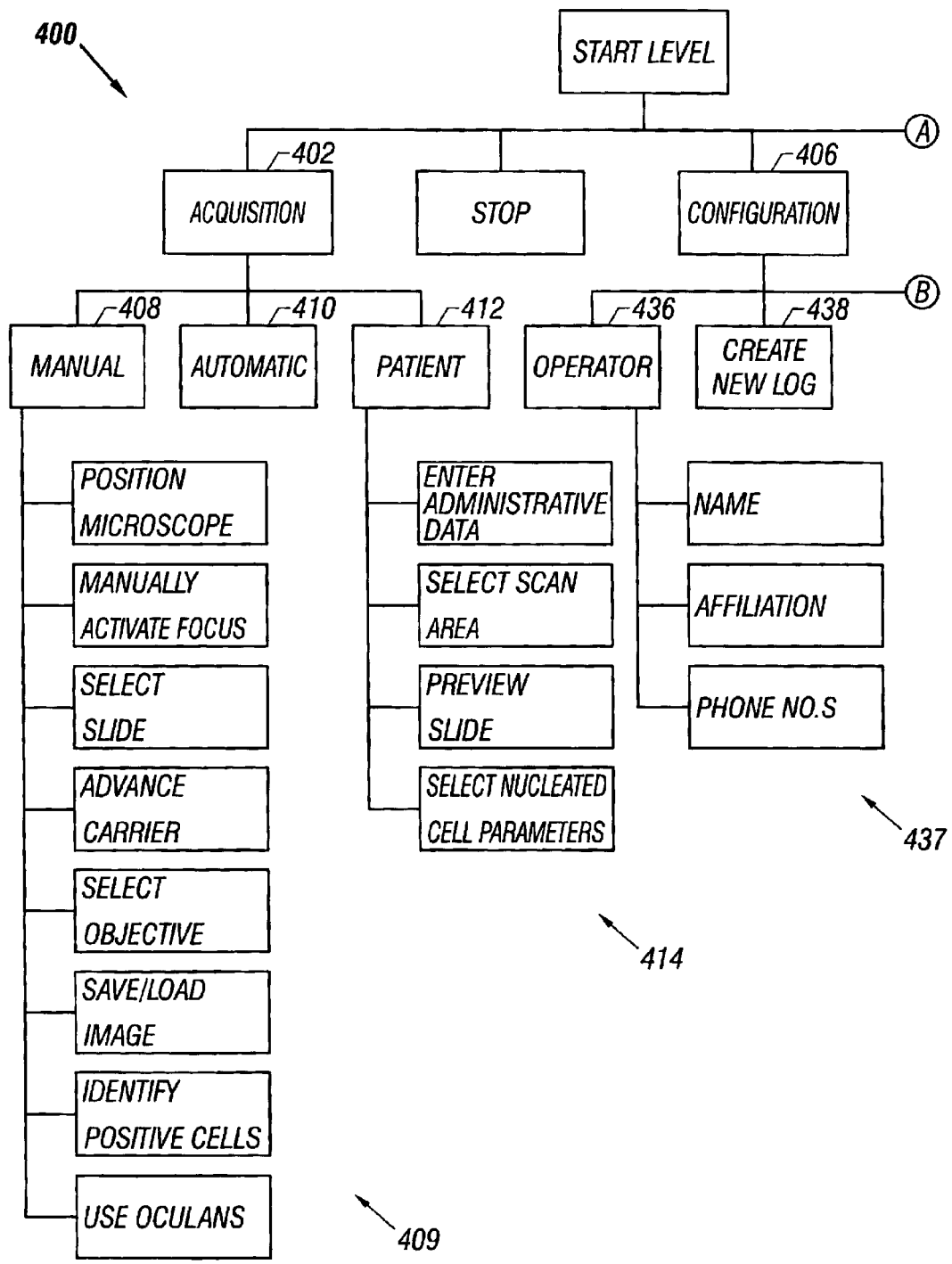
FIGS. 26a and 26b illustrate the apparatus functions available in a user interface of the apparatus.
Figure 26B:
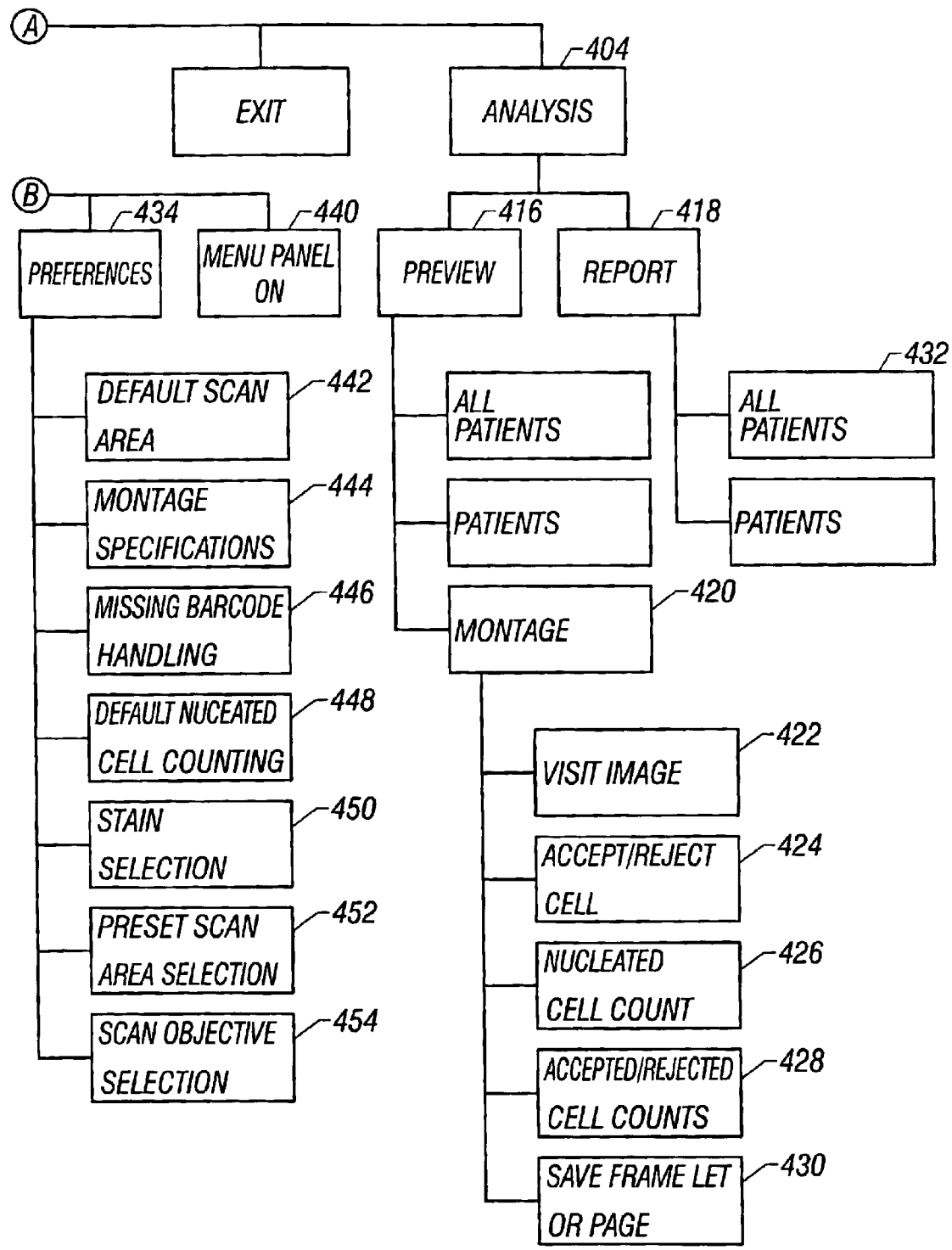

Referring to FIG. 26, the functions available in a user interface of the autostainer 1000 and/or imaging apparatus 10 are shown. From the user interface, which is presented graphically on computer monitor 26, an operator can select among apparatus functions that include acquisition 402, analysis 404, and configuration 406. At the acquisition level 402, the operator can select between manual 408 and automatic 410 modes of operation. In the manual mode, the operator is presented with manual operations 409. Patient information 414 regarding an assay can be entered at 412. In the analysis level 404, preview 416 and report 418 functions are made available. At the preview level 416, the operator can select a montage function 420. At this montage level, a pathologist can perform diagnostic review functions including visiting an image 422 (including images acquired by the autostainer), accept/reject a cell 424, nucleated cell counting 426, accept/reject cell counts 428, and saving of pages 430. The report level 418 allows an operator to generate patient reports 432. In the configuration level 406, the operator can select to configure preferences 434, input operator information 436 including Name, affiliation and phone number 437, create a system log 438, and toggle a menu panel 440. The configuration preferences include scan area selection functions 442 and 452; montage specifications 444, bar code handling 446, default cell counting 448, stain selection 450, and scan objective selection 454.

Figure 27:
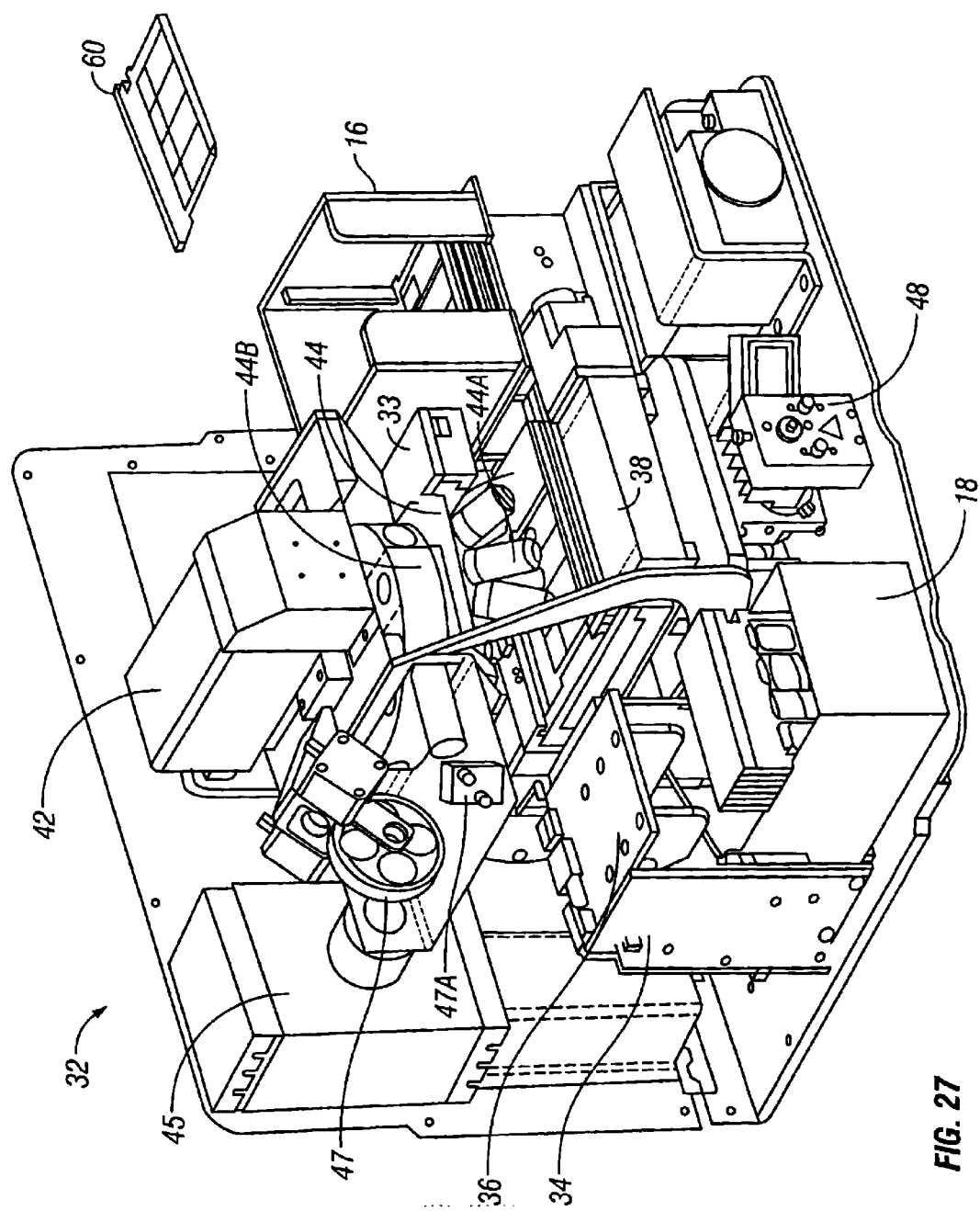
FIG. 27 is a perspective view of another embodiment of the invention.

An exemplary microscope subsystem 32 for processing fluorescently labeled samples is shown in FIG. 27. A carrier 60 having four slides thereon is shown. The number of slide in different embodiments can be greater than or less than four. An input hopper 16 for carriers with mechanisms to load a carrier 60 onto the stage at the bottom. Precision XY stage 38 with mechanism to hold carriers is shown. A turret 44 with microscope objective lenses 44a mounted on z axis stage is shown. Carrier outfeed tray 36 with mechanism 34 to drop carriers into slide carrier output hopper 18. The slide carrier output hopper 18 is a receptacle for those slides that have already been scanned. Bright field (transmission) light source 48 and fluorescent excitation light source 45 are also shown. Filter wheels 47 for fluorescent light path are shown, as well as a fold mirror 47*a* in the fluorescent light path. A bar code/OCR reader 33 is shown. Also shown are a computer controlled wheel 44*b* carrying fluorescent beam splitters (one position is empty for bright field mode) and a camera 42 capable of collecting both bright field (video rate) images and fluorescent (integrated) images.

An exemplary operating sequence is provided; however, it should be noted that other operating sequences may eliminate one or more steps and/or include one or more additional steps.

1) The operator enters each slide into a database entering the slide's unique identifying mark (a barcode or OCR string), the type of stain or reagent to be used, and the test that should be performed on the slide.
2) The slides are placed in carriers 60 and loaded into the input hopper associated with the autostainer.
3) The input hopper advances a carrier 60 onto the stage 1050.
4) A barcode/OCR reader reads the mark and the required test is looked up in a database.
5) A bright field light source is switched on.
6) Each slide is imaged to determine a region(s) on the slide containing a sample to be stained.
7) The image is processed as described above to detect changes in texture by analyzing pixel variance. Image analysis routines are used to determine which regions of the slide should be recorded in, for example, fluorescent images (the methods used to make this determination are described herein, the exact parameters will depend on the test being performed on the slide). Images and distinctive features may be identified and their coordinates stored and shared with the imaging apparatus.
8) The images can be saved and stitched together to form an image of the slide.
9) After staining under the appropriate conditions, the slide carrier is then unloaded from the autostainer stage 1050 and transferred to input hopper 16 of the imaging apparatus.
10) The imaging apparatus may perform a low magnification scan under a low power objective. Alternatively, the imaging apparatus can utilize an image acquired by the autostainer. Regardless of how the image is derived the imaging apparatus can perform an analysis of the image to identify objects of interest as well as various texture features that assist in defining a scan area. The location(s) of any objects of interest are stored so that the imaging apparatus can relocate the object of interest under the same or a higher power objective.
11) The turret 44 is switched to high power and further bright field transmission analysis and images are obtained. Alternatively, the turret 44 is switched to a higher power and the bright field transmission light source turned off and the fluorescent excitation light source is turned on.
12) High magnification fluorescent images of the candidate cells or objects of interest identified in step 10 would be collected. Because the critical regions would be a small fraction of the slide this would take much less time than imaging the entire slide. Alternatively, a serial subsample slide is advanced and processed to identify the coordinates of the distinctive features identified in the sample. The coordinates of any object of interest are then corrected in the subsample and the X-Y stage moves to the corrected coordinates to obtain fluorescent images.
13) Optionally (depending on the test) multiple images at a series of focus planes would be collected at each critical location. These would be used in tests that require a volumetric reconstruction of the nuclei of a cell.
14) All the images collected from the slide are written to a database (e.g., in an uncompressed or compressed mode).
15) Once all images have been collected on a slide, the stage would advance the next slide under the objective and the process would repeat.
16) Once all slides in a carrier are read, the process would repeat from step 3.
17) Anytime after the slides have been read and the images recorded into the database, a pathologist could review the images at a review station (a computer and monitor attached to the database but without a microscope).
18) The user could manually count fluorescent signals in the cells of interest or invoke image analysis software to score the fluorescent images by indicating regions of interest with a pointing device such as a mouse. If multiple focus planes have been collected the user could simulate focusing up and down in a live image by sweeping through a range of images at different focus levels.
19) Based on the calculated score, a diagnostic report can be generated.

Alternatively, the image analysis could be performed on the entirety of all regions for which fluorescent images were collected. In this case, the analysis could be performed off line between the time the image was collected and the time the user reviewed the image. When reviewing the images, the user could indicate regions whose scores should be included or excluded in creating the final report.

The automated detection of fluorescently labeled samples may be performed using a single slide or multiple slides. In using a single slide, the initial scan, under lower power and transmitted light, can be performed on the same slide as the one from which the fluorescent images will be found. In this case, the coordinates of any identified candidate objects of interest do not need to be corrected. Alternatively, the initial scan can be performed on a slide, and the data collected therefrom, and the fluorescent images can be collected from another slide having an adjacent serial section to the one that was initially scanned. In this case, the coordinates of any identified candidate objects of interest need to be corrected based upon the coordinates of any distinctive features in the serial samples. Fluorescent images may also be collected from multiple serial sections. For example, in situations where more than one fluorescent study is desired for a particular tissue, different studies can be carried out on adjacent sections placed on different slides. The slides of the different studies can be analyzed at high resolution and/or fluorescence from data collected from the initial scan of the first slide. In using adjacent tissue sections on multiple slides, however, it is desirable to orient the sections so that the specimens will correlate from one section to the other(s). This can be done by using landmarks, such as at least two unique identifiers or distinctive features, or outlining the tissue. Algorithms are known that can be used to calculate a location on the second or additional slides that can be mapped to any given location of the first slide. Examples of such algorithms are provided herein and include techniques as disclosed in U.S. Pat. Nos. 5,602,937 and 6,272,247, the disclosures of which are incorporated herein by reference in their entirety. In addition, such computer algorithms are commercially available from Matrox Electronic Systems Ltd. (Matrox Imagining Library (MIL) release 7.5).

Regardless of whether a single slide or multiple slides are used in the analysis, methods of selecting relevant regions of the slide for analysis are needed. It is desirable that the method be sufficiently selective so that time will not be wasted collecting images that the user never scores or includes in the report. However, it is also desirable that the method not be too selective, as the user may see a region that seems important in the bright field image and find that there is no high power fluorescent image in that region. Examples of methods for selecting the regions of the slide for fluorescing and/or high power magnification are provided.

In some methods, there will be criteria known a priori, that can be evaluated by image analysis. For instance, in testing for Her2 gene amplification, the IHC stain for the gene product can be used. This will mark any region of the tissue overexpressing the gene product (the protein Her2) a brown color. The image processing functions of densitometry or color thresholding can be used to convert the image to a map of the concentration of the protein. Once a map of relevant regions is available, the system could collect high magnification fluorescent images of either all regions that meet a criteria or a random sample of the relevant regions. Another example would be the use of the blue stain, H&E, to find regions of containing tumor cells. In this case, color thresholding for regions of darker blue will tend to find regions of containing tumor cells.

In other methods of selecting regions, one could use statistical methods that do not require a-priori knowledge to map the tissue sample into some number of zones that share some measurable characteristic. The system could then collect fluorescent images of samples of each zone. When the user reviews the bright field image of the entire tissue and selected regions in which to examine the fluorescent high magnification images, the system could offer an image of another region in the same zone with similar characteristics. There are a number of known algorithms that could be used for dividing the tissue into zones. For instance, if the tissue were divided into a grid and the average color of each grid element were measured, these could be plotted in color space and cluster analysis used to group them into a limited number of zones with similar color. There are also texture analysis algorithms that will partition an image into a number of zones each with similar texture.

In still other methods, it may occur that on review of the bright field image, the user may find a region in which she may want to see a fluorescent image and, for whatever reason, the algorithm did not make a fluorescent image that is usable. In this case, the system could be programmed to write the location of the region the user wanted back into the database so that, if the slide is reloaded into the microscope, the system can collect a fluorescent high magnification image at the exact location desired. This mode of operation could either be a fallback for the methods of selecting regions described above or a separate mode of operation in tests in which only the observer's judgment is suitable for deciding which regions are important to examine as fluorescent images.

The HER2/neu marker, for example, may be detected though the use of an anti-HER2/neu staining system, such as a commercially available kit, like that provided by DAKO (Carpinteria, Calif). A typical immunohistochemistry protocol includes: (1) prepare wash buffer solution; (2) deparaffinize and rehydrate sample or subsample; (3) perform epitope retrieval. Incubate 40 min in a 95° C. water bath. Cool slides for 20 min at room temperature; (4) apply peroxidase blocking reagent. Incubate 5 min; (5) apply primary antibody or negative control reagent. Incubate 30 min +/−1 min at room temperature. Rinse in wash solution. Place in wash solution bath; (6) apply peroxidase labeled polymer. Incubate 30 min +/−1 min at room temperature. Rinse in wash solution. Place in wash solution bath; (7) prepare DAB substrate chromagen solution; (8) apply substrate chromogen solution (DAB). Incubate 5–10 min. Rinse with distilled water; (9) counterstain; (10) mount coverslips. The slide includes a cover-slip medium to protect the sample and to introduce optical correction consistent with microscope objective requirements. A coverslip typically covers the entire prepared specimen. Mounting the coverslip does not introduce air bubbles obscuring the stained specimen. This coverslip could potentially be a mounted 1½ thickness coverslip with DAKO Ultramount medium; (11) a set of staining control slides are run with every worklist. The set includes a positive and negative control. The positive control is stained with the anti-HER2 antibody and the negative is stained with another antibody. Both slides are identified with a unique barcode. Upon reading the barcode, the instrument recognizes the slide as part of a control set, and runs the appropriate application. There may be one or two applications for the stain controls; (12) a set of instrument calibration slides includes the slides used for focus and color balance calibration; (13) a dedicated carrier is used for one-touch calibration. Upon successful completion of this calibration procedure, the instrument reports itself to be calibrated. Upon successful completion of running the standard slides, the user is able to determine whether the instrument is within standards and whether the inter-instrument and intra-instrunent repeatability of test results.

A hematoxylin/eosin (H/E) slide is prepared with a standard H/E protocol. Standard solutions include the following: (1) Gills hematoxylin (hematoxylin 6.0 g; aluminum sulphate 4.2 g; citric acid 1.4 g; sodium iodate 0.6 g; ethylene glycol 269 ml; distilled water 680 ml); (2) eosin (eosin yellowish 1.0 g; distilled water 100 ml); (3) lithium carbonate 1% (lithium carbonate 1 g; distilled water 100 g); (4) acid alcohol 1% 70% (alcohol 99 ml conc.; hydrochloric acid 1 ml); and (5) Scott's tap water. In a beaker containing 1 L distilled water, add 20 g sodium bicarbonate and 3.5 g magnesium sulphate. Add a magnetic stirrer and mix thoroughly to dissolve the salts. Using a filter funnel, pour the solution into a labeled bottle.

The staining procedure is as follows: (1) bring the sections to water; (2) place sections in hematoxylin for 5 min; (3) wash in tap water; (4) 'blue' the sections in lithium carbonate or Scott's tap water; (5) wash in tap water; (6) place sections in 1% acid alcohol for a few seconds; (7) wash in tap water; (8) place sections in eosin for 5 min; (9) wash in tap water; and (10) dehydrate, clear. Mount sections. The results of the H/E staining provide cells with nuclei stained blue-black, cytoplasm stained varying shades of pink; muscle fibers stained deep pinky red; fibrin stained deep pink; and red blood cells stained orange-red.

In another aspect, the invention provides automated methods for analysis of estrogen receptor and progesterone receptor. The estrogen and progesterone receptors, like other steroid hormone receptors, play a role in developmental processes and maintenance of hormone responsiveness in cells. Estrogen and progesterone receptor interaction with target genes is of importance in maintenance of normal cell function and is also involved in regulation of mammary tumor cell function. The expression of progesterone receptor and estrogen receptor in breast tumors is a useful indicator for subsequent hormone therapy. An anti-estrogen receptor antibody labels epithelial cells of breast carcinomas which express estrogen receptor. An immunohistochemical assay of the estrogen receptor is performed using an anti-estrogen receptor antibody, for example the well-characterized 1D5 clone, and the methods of Pertchuk, et al. (Cancer 77: 2514–2519, 1996) or a commercially available immunohistochemistry system such as that provided by DAKO (Carpenteria Calif.; DAKO LSAB2 Immunostaining System). Accordingly, the invention provides a method whereby tumor cells are identified using a first agent and normal light microscopy and then further characterized using antibodies to a progesterone and/or estrogen receptor, wherein the antibodies are tagged with a fluorescent agent.

For example, the labeling of progesterone receptor has been demonstrated in the nuclei of cells from various histologic subtypes. An anti-progesterone receptor antibody labels epithelial cells of breast carcinomas which express progesterone receptor. An immunohistochemical assay of the progesterone receptor is performed using an anti-estrogen receptor antibody, for example the well-characterized 1A6 clone and methods similar to those of Pertchuk, et al. (Cancer 77: 2514–2519, 1996).

Micrometastases/metastatic recurring disease (MM/MRD). Metastasis is the biological process whereby a cancer spreads to a distant part of the body from its original site. A micrometastases is the presence of a small number of tumor cells, particularly in the lymph nodes and bone marrow. A metastatic recurring disease is similar to micrometastasis, but is detected after cancer therapy rather than before therapy. An immunohistochemical assay for MM/MRD is performed using a monoclonal antibody that reacts with an antigen (a metastatic-specific mucin) found in bladder, prostate and breast cancers. An MM/MRD can be identified by first staining cells to identify nucleic and cellular organelles or alternatively by staining cells to differentiate between bladder and other prostate cells. Subsamples corresponding to the original first subsample can then be stained with and antibody to a mucin protein, wherein the antibody is detectably labeled with a fluorescent molecule. In this way, a first subsample is prescreened to identify objects of interest including a particular cell type and then screened with a specific antibody to a molecule of interest associated with the object of interest. The first screening step allows for an automated system to identify the coordinates in a first subsample having the object of interest whereby the coordinates are then used to focus and obtaining fluorescent images in a second subsample at the same coordinates.

Another example of the application of the invention includes the use of MIB-1. MIB-1 is an antibody that detects the antigen Ki-67. The clinical stage at first presentation is related to the proliferative index measured with Ki-67. High index values of Ki-67 are positively correlated with metastasis, death from neoplasia, low disease-free survival rates, and low overall survival rates. For example, a first agent (e.g., a staining agent) is used to identify an object of interest such as a marker for cancer cells. A diagnosis or prognosis of a subject may then be performed by further analyzing any object of interest for the presence of Ki-67 using an antibody that is detectably labeled with a fluorescent agent. The coordinates of any such object of interest (e.g., a suspected cancer cell) are then used to focus and obtain a fluorescent image of a sample or subsample contacted with a fluorescently labeled MIB-1. The presence of a fluorescent signal at such coordinates is indicative of a correlation of the cancer cell with metastasis and/or survival rates.

In another aspect, microvessel density analysis can be performed and a determination of any cytokines, angiogenic agents, and the like, which are suspected of playing a role in the angiogenic activity identified. Angiogenesis is a characteristic of growing tumors. By identifying an angiogenic agent that is expressed or produced aberrantly compared to normal tissue, a therapeutic regimen can be identified that targets and modulates (e.g., increases or decreases) the angiogenic molecule or combination of molecules. For example, endothelial cell proliferation and migration are characteristic of angiogenesis and vasculogenesis. Endothelial cells can be identified by markers on the surface of such endothelial cells using a first agent that labels endothelial cells. An automated microscope system (such as that produced by Chroma Vision Medical Systems, Inc., California) scans the sample for objects of interest (e.g., endothelial cells) stained with the first agent. The automated system then determines the coordinates of an object of interest and uses these coordinates to focus in on the sample or a subsample that has been contacted with a second fluorescently labeled agent. In one aspect, a second agent (e.g., an antibody, polypeptide, and/or oligonucleotide) that is labeled with a fluorescent indicator is then used to detect the specific expression or presence of any number of angiogenic agents.

Overexpression of the p53 oncogene has been implicated as the most common genetic alteration in the development of human malignancies. Investigations of a variety of malignancies, including neoplasms of breast, colon, ovary, lung, liver, mesenchyme, bladder and myeloid, have suggested a contributing role of p53 mutation in the development of malignancy. The highest frequency of expression has been demonstrated in tumors of the breast, colon, and ovary. A wide variety of normal cells do express a wildtype form of p53 but generally in restricted amounts. Overexpression and mutation of p53 have not been recognized in benign tumors or in normal tissue. In addition, p53 has also be implicated as a cocontributor to tumors. For example, BRCA-1 has been used as marker for ovarian cancer, however p53 has also been implicated as playing a role in BRCA-1 ovarian cancers (Rose and Buller, Minerva Ginecol. 54(3):201–9, 2002). Using the methods of the invention a sample is stained for BRCA-1 with a first agent and objects of interest are identified using light microscopy. The same sample or a subsample, having substantially identical coordinates with respect to an object of interest, is then contacted with a second agent comprising a fluorescent label that interacts with a p53 nucleic acid or polypeptide. The sample or subsample is then analyzed via fluorescent microscopy to identify any fluorescent signals at the coordinates associated with the object of interest to determine the presence or absence of p53 nucleic acids or polypeptides. An anti-p53 antibody useful in this embodiment includes, for example, the well-characterized DO-7 clone.

An example of an object of interest includes nucleoli, an organelle in a cell nucleus. Uses of nucleoli as objects of interest are apparent when determining cervical dysplasia. In cervical dysplasia normal or metaplastic epithelium is replaced with atypical epithelial cells that have cytologic features that are pre-malignant (nuclear hyperchromatism, nuclear enlargement and irregular outlines, increased nuclear-to-cytoplasmic ratio, increased prominence of nucleoli) and chromosomal abnormalities. The changes seen in dysplastic cells are of the same kind but of a lesser degree than those of frankly malignant cells. In addition, there are degrees of dysplasia (mild, moderate, severe).

In yet another aspect, and object of interest may be the p24 antigen of Human immunodeficiency virus (HIV). Anti-p24 antibodies are used to detect the p24 antigen to determine the presence of the HIV virus. Further assays can then be performed using FISH to determine the genetic composition of the HIV virus using fluorescently labeled oligonucleotide probes and the like.

One method of sample preparation is to react a sample or subsample with an agent the specifically interacts with a molecule in the sample. Examples of such agents include a monoclonal antibody, a polyclonal antiserum, or an oligonucleotide or polynucleotide. Interaction of the agent with its cognate or binding partner can be detected using an enzymatic reaction, such as alkaline phosphatase or glucose oxidase or peroxidase to convert a soluble colorless substrate linked to the agent to a colored insoluble precipitate, or by directly conjugating a dye or a fluorescent molecule to the probe. In one aspect of the invention a first agent is labeled with a non-fluorescent label (e.g., a substrate that gives rise to a precipitate) and a second agent is labeled with a fluorescent label. If the same sample is to be used for both non-fluorescent detection and fluorescent detection, the non-fluorescent label preferably does not interfere with the fluorescent emissions from the fluorescent label. Examples of non-fluorescent labels include enzymes that convert a soluble colorless substrate to a colored insoluble precipitate (e.g., alkaline phosphatase, glucose oxidase, or peroxidase). Other non-fluorescent agent include small molecule reagents that change color upon interaction with a particular chemical structure.

In one aspect of Fluorescent in Situ Hybridization (FISH), a fluorescently labeled oligonucleotide (e.g., a DNA, a RNA, and a DNA-RNA molecule) is used as an agent. The fluorescently labeled oligonucleotide is contacted with a sample (e.g., a tissue sample) on a microscope slide. If the labeled oligonucleotide is complementary to a target nucleotide sequence in the sample on the slide, a bright spot will be seen when visualized on a microscope system comprising a fluorescent excitation light source. The intensity of the fluorescence will depend on a number of factors, such as the type of label, reaction conditions, amount of target in the sample, amount of oligonucleotide agent, and amount of label on the oligonucleotide agent. There are a number of methods, known in the art that can be used to increase the amount of label attached to an agent in order to make the detection easier. FISH has an advantage that individual cells containing a target nucleotide sequences of interest can be visualized in the context of the sample or tissue sample. As mentioned above, this can be important in testing for types of diseases and disorders including cancer in which a cancer cell might penetrate normal tissues.

A given fluorescent molecule is characterized by an excitation spectrum (sometimes referred to as an absorption spectrum) and an emission spectrum. When a fluorescent molecule is irradiated with light at a wavelength within the excitation spectrum, the molecule fluoresces, emitting light at wavelengths in the emission spectrum for that particular molecule. Thus when a sample is irradiated with excitation light at a wavelength that excites a certain fluorescent molecule, the sample containing the fluorescent molecule fluoresces. In some instances the light emanating from the sample and surrounding area may be filtered to reject light outside a given fluorescent agent's emission spectrum. Thus an image acquired from a sample contacted with an agent comprising a fluorescent label shows only objects of interest in the sample that bind or interact with the fluorescently labeled agent.

What is claimed is:

1. An apparatus comprising:
   an imaging camera;
   a stage;
   at least one reagent container;
   at least one reagent dispenser device for dispensing a reagent from the at least one reagent container;
   a dispenser relocation device for moving the at least one dispenser and/or stage relative to one another; and
   a computer;
   wherein the imaging camera is in communication with the computer and is operable to image a slide on the stage and determine a processing parameter for the slide, the computer comprising an algorithm on a computer readable medium for instructing the computer to determine a location and an area comprising a biological sample on the slide from an image obtained by the imaging camera, instructing the dispenser relocation device to relocate the at least one dispenser to the area comprising the biological sample and dispensing a reagent from the at least one reagent container in accordance with the processing parameter.

2. The apparatus of claim 1, further comprising a tracer device operably linked to the dispenser relocation device, wherein the tracer device traces an outline of a staining region around the area comprising the biological sample.

3. The apparatus of claim 1, wherein the stage moves in relation to the at least one dispenser.

4. The apparatus of claim 1, wherein the at least one dispenser moves in relation to the stage.

5. The apparatus of claim 1, wherein the stage comprises slides.

6. The apparatus of claim 1, wherein the at least one dispenser dispenses a staining reagent.

7. The apparatus of claim 1, wherein the at least one dispenser dispenses more than a single type of staining reagent.

8. The apparatus of claim 1, wherein the camera scans an image of the slide, including any biological sample thereon.

9. The apparatus of claim 8, wherein the image is used to move the at least one dispenser or stage in relation to each other so that the at least one dispenser dispenses a reagent onto the samples on the slide.

10. The apparatus of claim 8, wherein the image is used to direct a tracer to outline the biological sample on the slide.

11. The apparatus of claim 10, wherein the tracer outlines the sample with a hydrophobic medium.

12. The apparatus of claim 11, wherein the at least one dispenser the dispenses a staining reagent within the outline of the sample.

13. The apparatus of claim 10, wherein the at least one dispenser is also the tracer.

14. The apparatus of claim 1, wherein the camera scans a bar code on the slide.

15. The apparatus of claim 9, wherein the bar code comprises information relating to the sample, information relating to the staining of the slide, or both of the foregoing.

* * * * *